US012590297B2

(12) United States Patent
Clevers et al.

(10) Patent No.: US 12,590,297 B2

(45) Date of Patent: Mar. 31, 2026

(54) DIFFERENTIATION METHOD

(71) Applicant: Koninklijke Nederlandse Akademie Van Wetenschappen, Utrecht (NL)

(72) Inventors: Johannes Carolus Clevers, Utrecht (NL); Helmuth Gehart, Utrecht (NL)

(73) Assignee: Koninklijke Nederlandse Akademie Van Wetenschappen, Utrecht (NL)

(*) Notice: Subject to any disclaimer, the term of this patent is extended or adjusted under 35 U.S.C. 154(b) by 7 days.

(21) Appl. No.: 18/100,195

(22) Filed: Jan. 23, 2023

(65) Prior Publication Data

US 2023/0272347 A1 Aug. 31, 2023

Related U.S. Application Data

(62) Division of application No. 16/078,354, filed as application No. PCT/EP2017/054797 on Mar. 1, 2017, now Pat. No. 11,591,572.

(30) Foreign Application Priority Data

Mar. 1, 2016 (GB) ..................................... 1603569

(51) Int. Cl.

*C12N 5/071* (2010.01)
*A61K 35/407* (2015.01)
*G01N 33/50* (2006.01)

(52) U.S. Cl.

CPC .......... *C12N 5/0672* (2013.01); *A61K 35/407* (2013.01); *C12N 5/0671* (2013.01); *G01N 33/5088* (2013.01); *C12N 2501/01* (2013.01); *C12N 2501/11* (2013.01); *C12N 2501/119* (2013.01); *C12N 2501/12* (2013.01); *C12N 2501/155* (2013.01); *C12N 2501/345* (2013.01); *C12N 2501/39* (2013.01); *C12N 2501/415* (2013.01); *C12N 2501/42* (2013.01); *C12N 2501/727* (2013.01); *C12N 2501/805* (2013.01); *C12N 2501/999* (2013.01); *C12N 2506/14* (2013.01)

(58) Field of Classification Search

CPC ... C12N 5/0671; C12N 5/0672; A61K 35/407

See application file for complete search history.

(56) References Cited

U.S. PATENT DOCUMENTS

| | | | |
|---|---|---|---|
| 5,981,483 | A | 11/1999 | Dennis et al. |
| 6,743,626 | B2 | 6/2004 | Baum et al. |
| 8,642,339 | B2 | 2/2014 | Sato et al. |
| 8,685,726 | B2 | 4/2014 | Schulz et al. |
| 10,597,633 | B2 | 3/2020 | Ortega et al. |
| 11,591,572 | B2 | 2/2023 | Clevers et al. |
| 2003/0003088 | A1 | 1/2003 | Tsao et al. |
| 2003/0129751 | A1 | 7/2003 | Grikscheit et al. |
| 2003/0138948 | A1 | 7/2003 | Fisk et al. |
| 2003/0138951 | A1 | 7/2003 | Yin |
| 2004/0175367 | A1 | 9/2004 | Herlyn et al. |
| 2004/0191902 | A1 | 9/2004 | Hambor et al. |
| 2004/0229355 | A1 | 11/2004 | Chen et al. |
| 2007/0010008 | A1 | 1/2007 | Tseng et al. |
| 2007/0036769 | A9 | 2/2007 | Li et al. |
| 2007/0122903 | A1 | 5/2007 | Rezania et al. |
| 2007/0128719 | A1 | 6/2007 | Tseng et al. |
| 2008/0112890 | A1 | 5/2008 | Lelkes et al. |
| 2008/0113433 | A1 | 5/2008 | Robins et al. |
| 2008/0166327 | A1 | 7/2008 | Asahara et al. |
| 2008/0182328 | A1 | 7/2008 | Snyder et al. |
| 2008/0233088 | A1 | 9/2008 | Guha et al. |
| 2008/0242594 | A1 | 10/2008 | McKay et al. |
| 2009/0275067 | A1 | 11/2009 | Taniguchi et al. |
| 2010/0047853 | A1 | 2/2010 | Kuo et al. |
| 2010/0100396 | A1 | 4/2010 | Daven et al. |
| 2010/0275280 | A1 | 10/2010 | Clevers et al. |
| 2011/0008893 | A1 | 1/2011 | Sugimura et al. |
| 2011/0191868 | A1 | 8/2011 | Gupta et al. |
| 2012/0021513 | A1 | 1/2012 | Schulz et al. |
| 2012/0028355 | A1 | 2/2012 | Sato et al. |
| 2012/0196312 | A1 | 8/2012 | Sato et al. |
| 2012/0207744 | A1 | 8/2012 | Mendlein et al. |
| 2013/0005737 | A1 | 1/2013 | Prabhu et al. |
| 2013/0008956 | A1 | 1/2013 | Ashfield |
| 2013/0052729 | A1 | 2/2013 | Pourquie et al. |
| 2013/0089562 | A1 | 4/2013 | French et al. |
| 2013/0189327 | A1 | 7/2013 | Ortega et al. |
| 2013/0280809 | A1 | 10/2013 | Efe et al. |
| 2014/0044713 | A1 | 2/2014 | Lau et al. |
| 2014/0243227 | A1 | 8/2014 | Clevers et al. |
| 2014/0256037 | A1 | 9/2014 | Sato et al. |

(Continued)

FOREIGN PATENT DOCUMENTS

| | | |
|---|---|---|
| CN | 101420964 A | 4/2009 |
| CN | 103180436 A | 6/2013 |

(Continued)

OTHER PUBLICATIONS

Strazzabosco et al., The Anatomical Record, 291:653-660 (2008) (Year: 2008).*

Zhao et al, Nature Reviews Methods Primers, (2022) 2:94, pp. 1-21 (Year: 2022).*

Martinez-Jimenez et al Current Drug Metabolism, vol. 8, Iss 2, Feb. 2007, pp. 185-194 (Year: 2007).*

NIH National Cancer Institute—Organoid definition, retrieved from the internet (May 6, 2025): https://www.cancer.gov/publications/dictionaries/cancer-terms/def/organoid (Year: 2025).*

Normal Liver Histology 101 (Jun. 12, 2020), retrieved from the internet: https://www.aasld.org/liver-fellow-network/core-series/pathology-pearls/normal-liver-histology-101 (Year: 2020).*

(Continued)

*Primary Examiner* — Evelyn Y Pyla

(74) *Attorney, Agent, or Firm* — McNeill PLLC

(57) ABSTRACT

The invention relates to differentiation methods for progenitor cells, e.g. mammalian epithelial stem cells, differentiation media for use in said methods, organoids and cells obtainable by said methods and uses, including therapeutic uses, thereof.

9 Claims, 11 Drawing Sheets

(56) References Cited

U.S. PATENT DOCUMENTS

| | | | |
|---|---|---|---|
| 2014/0302491 A1 | 10/2014 | Nadauld et al. |
| 2015/0140013 A1 | 5/2015 | Ramaswamy |
| 2015/0231201 A1 | 8/2015 | Clevers et al. |
| 2015/0276719 A2 | 10/2015 | Beekman et al. |
| 2016/0002595 A1 | 1/2016 | Keller et al. |
| 2017/0191030 A1 | 7/2017 | Ortega et al. |
| 2017/0275592 A1 | 9/2017 | Sachs et al. |
| 2017/0342385 A1 | 11/2017 | Sachs et al. |
| 2018/0066233 A1 | 3/2018 | Ortega et al. |
| 2018/0072995 A1 | 3/2018 | Sato et al. |
| 2018/0187191 A1 | 7/2018 | Zeng |
| 2018/0221441 A1 | 8/2018 | Clevers et al. |
| 2018/0258400 A1 | 9/2018 | Ng et al. |
| 2019/0031992 A1 | 1/2019 | Kerns et al. |
| 2019/0100728 A1 | 4/2019 | Sato et al. |
| 2019/0383799 A1 | 12/2019 | Beekman et al. |
| 2020/0172861 A1 | 6/2020 | Ortega et al. |
| 2020/0377860 A1 | 12/2020 | Freedman et al. |
| 2021/0047618 A1 | 2/2021 | Clevers et al. |
| 2021/0333266 A1 | 10/2021 | Beekman et al. |
| 2022/0340879 A1 | 10/2022 | De Lau et al. |

FOREIGN PATENT DOCUMENTS

| | | | |
|---|---|---|---|
| CN | 103237888 A | 8/2013 |
| CN | 104508121 A | 4/2015 |
| EP | 0953633 A1 | 11/1999 |
| EP | 2412800 A1 | 2/2012 |
| EP | 2420566 A1 | 2/2012 |
| EP | 2772534 A1 | 9/2014 |
| EP | 2138571 B1 | 4/2017 |
| EP | 3318627 A1 | 5/2018 |
| EP | 3441458 A1 | 2/2019 |
| EP | 3505620 B1 | 7/2023 |
| JP | 2012000097 A | 1/2012 |
| WO | 2004050827 A2 | 6/2004 |
| WO | 2004087896 A3 | 11/2004 |
| WO | 2005040391 A1 | 5/2005 |
| WO | 2005120547 A1 | 12/2005 |
| WO | 2007141657 A2 | 12/2007 |
| WO | 2007127454 A3 | 4/2008 |
| WO | 2008046649 A1 | 4/2008 |
| WO | 2008101215 A1 | 8/2008 |
| WO | 2009022907 A2 | 2/2009 |
| WO | 2009024595 A2 | 2/2009 |
| WO | 2010011352 A2 | 1/2010 |
| WO | 2010015938 A2 | 2/2010 |
| WO | 2010016766 A2 | 2/2010 |
| WO | 2010090513 A1 | 8/2010 |
| WO | 2010090513 A2 | 8/2010 |
| WO | 2010119819 A1 | 10/2010 |
| WO | 2010129294 A3 | 4/2011 |
| WO | 2011098402 A1 | 8/2011 |
| WO | 2011043591 A3 | 9/2011 |
| WO | 2012014076 A2 | 2/2012 |
| WO | 2012025725 A1 | 3/2012 |
| WO | 2012044992 A2 | 4/2012 |
| WO | 2012068251 A2 | 5/2012 |
| WO | 2012014076 A3 | 9/2012 |
| WO | 2012087965 A3 | 10/2012 |
| WO | 2012140274 A2 | 10/2012 |
| WO | 2012168930 A2 | 12/2012 |
| WO | 2012140274 A9 | 3/2013 |
| WO | 2013054112 A1 | 4/2013 |
| WO | 2013061608 A1 | 5/2013 |
| WO | 2013093812 A2 | 6/2013 |
| WO | 2013074681 A9 | 11/2013 |
| WO | 2014015777 A1 | 1/2014 |
| WO | 2014066649 A1 | 5/2014 |
| WO | 2014124527 A1 | 8/2014 |
| WO | 2014127170 A1 | 8/2014 |
| WO | 2014127219 A1 | 8/2014 |
| WO | 2014145389 | 9/2014 |
| WO | 2014159356 A1 | 10/2014 |
| WO | 2014170411 A1 | 10/2014 |
| WO | 2015040142 A1 | 3/2015 |
| WO | 2015173425 A1 | 11/2015 |
| WO | 2015179393 A1 | 11/2015 |
| WO | 2015200901 A1 | 12/2015 |
| WO | 2016016894 A1 | 2/2016 |
| WO | 2016056999 A1 | 4/2016 |
| WO | 2016083612 A1 | 6/2016 |
| WO | 2016083613 A2 | 6/2016 |
| WO | 2016094457 A1 | 6/2016 |
| WO | 2017048193 A1 | 3/2017 |
| WO | 2017120543 A1 | 7/2017 |
| WO | 2017149025 A1 | 9/2017 |
| WO | 2017205511 A1 | 11/2017 |
| WO | 2017220586 A1 | 12/2017 |
| WO | 2018035138 A1 | 2/2018 |
| WO | 2018036119 A1 | 3/2018 |
| WO | 2018052953 A1 | 3/2018 |
| WO | 2018102202 A1 | 6/2018 |
| WO | 2019122388 A1 | 6/2019 |
| WO | 2019228516 A1 | 12/2019 |
| WO | 2020205755 A1 | 10/2020 |
| WO | 2020234250 A1 | 11/2020 |

OTHER PUBLICATIONS

"CP-A31398, which restitutes mutant p53 functions, suppresses the increase of dominant negative p53 gene mutation-dependent cancer cell proliferation and metastasis," Acta Obstetrica et Gynaecologica Japonica, Published by Nihon Sanka Fujinka Gakkai Zasshi, 2006, vol. 58, No. 2, p. 1-88, p. 400 (S-252) (1 page).

Sato et al., "EGFR inhibitors prevent induction of cancer stem like cells in esophageal squamous cell carcinoma by suppressing epithelial-mesenchymal transition," Cancer Biology & Therapy, 16:6, 933-940, DOI: 10.1080/15384047.2015.1040959, May 28, 2015 (9 pages).

Tian et al., "Opposing activities of Notch and Wnt signaling regulate intestinal stem cells and gut homeostasis," Cell Rep. Apr. 7, 2015; 11(1): 33-42. doi:10.1016/j.celrep.2015.03.007 (18 pages).

You et al., "The type III TGF-b receptor signals through both Smad3 and the p38 MAP kinase pathways to contribute to inhibition of cell proliferation," Carcinogenesis vol. 28 No. 12 pp. 2491-2500, 2007 (10 pages).

Fritsch et al., "Characterization of the Novel and Specific PI3Kα Inhibitor NVP-BYL719 and Development of the Patient Stratification Strategy for Clinical Trials," Mol Cancer Ther. 2014; 13(5):1117-29 (14 pages).

Fuchs, Ota, "Inhibition of TGF-B Signaling for the Treatment of Tumor Metastasis and Fibrotic Diseases", Current Signal Transduction Therapy, 2011, 6: 29-43 (15 pages).

Fujii M et al., "A Colorectal Tumor Organoid Library Demonstrates Progressive Loss of Niche Factor Requirements during Tumorigenesis," Cell Stem Cell. Jun. 2, 2016; 18:827-838 (13 pages).

Furuyama et al., Continuous cell supply from a Sox9-expressing progenitor zone in adult liver, exocrine pancreas and Intestine 2011 Nat Genet 43: 34-41 (11 pages).

Gao et al., "3D Spheroid/Organoid Models of Lung Cancer to Study Lung Cancer Pathogenesis and Testing of New Therapeutics", Journal of Thoracic Oncology, vol. 12, S1544, 1 page (Jun. 21, 2017).

Gerbal-Chaloin et al., "The WNT/b-Catenin Pathway Is a Transcriptional Regulator of CYP2E1, CYP1A2, and Aryl Hydrocarbon Receptor GeneExpression in Primary Human Hepatocytes," (2014) Molecular Pharmacology 86:624-634.

Ghasemi et al., "High-throughput testing in head and neck squamous cell carcinoma identifies agents with preferential activity in human papillomavirus-positive or negative cell lines," Ocotarget, 2018, 9(40): 26064-26071 (8 pages).

Ghosh et al., "Activity Assay of Epidermal Growth Factor Receptor Tyrosine Kinase Inhibitors in Triple-Negative Breast Cancer Cells Using Peptide-Conjugated Magnetic Beads," ASSAY and Drug Development Technologies, 11(1):44-51; Jan./Feb. 2013.

Gillison et al., "A causual role for human papillomavirus in head and neck cancer," Lancet. 2004, 363(9420): 1488-9 (2 pages).

(56) References Cited

OTHER PUBLICATIONS

Gjorevski et al., "Designer matrices for intestinal stem cell and organoid culture," Nature, Nov. 2016, 539:560-564 (17 pages).
Gonzalez et al., "Identification of 9 Genes differentially Expressed in Head and Neck Squamous Cell Carcinoma," Arch Otolaryngol Head Neck Surg. United States; 2003; 129:754-759 (6 pages).
Gonzalez et al., "Notch Inhibition Prevents Differentiation of Human Limbal Stem/Progenitor Cells in vitro," Scientific Reports, (2019) 9 (10373): 1-11 (11 pages).
Greene et al., "Partial Hepatectomy in the Mouse: Technique and Perioperative Management," 2003 J Invest Surg 16:99-102 (4 pages).
Griffin et al., "Human Keratinocyte Cultures in the Investigation of Early Steps of Human Papillomavirus Infection," Methods Mol Biol. 2014; 219-238 (19 pages).
Grompe, M., "Liver Stem Cells, Where Art Thou?," Cell Stem Cell 15: 257-258, 2014 (2 pages).
Grompe, M. "Fah Knockout Animals as Models for Therapeutic Liver Repopulation," Hereditary Tyrosinemia, Advances in Experimental Medicine and Biology, 2017, 959: 215-230 (16 pages).
Grun et al., "Single-cell messenger RNA sequencing reveals rare intestinal cell types," Nature vol. 525, pp. 251-255 (Sep. 10, 2015).
Guan et al., "A meta-analysis comparing cisplatin-based to carboplatinbased chemotherapy in moderate to advanced squamous cell carcinoma of head and neck (SCCHN)," Oncotarget. 2016; 7(6): 7110-7119 (10 pages).
Gui et al., "Heregulin protects mesenchymal stem cells from serum deprivation and hypoxia-induced apoptosis," Mol Cell Biochem, 305:171-178 (2007).
Gunawardene et al., "Classification and functions of enteroendocrine cells of the lower gastrointestinal tract," Int. J. Exp. Path. (2011) 92: 219-231.
Haegebarth et al., "Wnt Signaling, Lgr5, and Stem Cells in the Intestine and Skin," The American Journal of Pathology, Mar. 2009, 174(3):715-721 (7 pages).
Hall et al., "The α1/β6 and α6/β1 Integrin Heterodimers Mediate Cell Attachment to Distinct Sites on Laminin," The Journal of Cell Biology, Jun. 1990, 110:2175-2184 (10 pages).
Harada et al., "Rapid formation of hepatic organoid in collagen sponge by rat small hepatocytes and hepatic honparenchymal cells," Journal of Hepatology (2003) 39: 716-723.
Aramis et al., "De novo crypt formation and juvenile polyposis on BMP inhibition in mouse intestine." Science, Mar. 12, 2004, 303(5664):1684-1686.
Hashimshony et al., "CEL-Seq: Single-Cell RNA-Seq by Multiplexed Linear Amplification," Cell Reports 2: 666-673, Sep. 27, 2012.
Hashimshony et al., "CEL-Seq2: sensitive highly-multiplexed single-cell RNA-Seq," Genome Biol 17: 77, 2016 (7 pages).
Hayashi et al., "Establishment and characterization of a parietal endoderm-like cell line derived from Engelbreth-Holm-Swarm tumor (EHSPEL), a possible resource for an engineered basement membrane matrix," Matrix Biology, (2004) 23:47-62 (6 pages).
Heuberger et al., "Shp2/MAPK signaling controls goblet/paneth cell fate decisions in the intestine, " 111(9):3472-3477 (2014).
Hirshhaeuser et al., "Efficacy of catumaxomab in tumor spheroid killing is mediated by its trifunctional mode of action," Cancer Immunol Immunother, Jul. 2010, 59:1675-1684 (10 pages).
Ho et al., "Preliminary Results From a Phase 2 Trial of Tipifarnib in HRAS-Mutant Head and Neck Squamous Cell Carcinomas," Int J Radiat Oncol Biol Phys. 2018; 100(5): 1367 (1 page).
Hofer and Drenckhahn, "Cytoskeletal markers allowing discrimination between brush cells and other epithelial cells of the gut including enteroendocrine cells," Cell Biol (1996) 105:405-412.
Homback-Klonisch et al., Adult stem cells and their trans-differentiation potential-perspectives and therapeutic applications. J Mol Med (Berl). 2008;86(12):1301-1314 (26 pages).
Hoogstraat et al., "Simultaneous Detection of Clinically Relevant Mutations and Amplifications for Routine Cancer Pathology," J Mol Diagnostics. 2015; 17(1): 10-18 (9 pages).
Hou et al., "Pluripotent Stem Cells Induced from Mouse Somatic Cells by Small-Molecule Compounds," Science Express, 10.1126/science.1239278; 8 pages (Jul. 18, 2013). http://www.sciencemag.org/content/early/recent.
Howitt et al., "Tuft cells, taste-chemosensory cells, orchestrate parasite type 2 immunity in the gut," Science. Mar. 18, 2016; 351(6279): 1329-1333.
Hsieh et al., "Truncated Mammalian Notch1 Activates CBF1/RBPJk-Repressed Genes by a Mechanism Resembling That of Esptein-Barr Virus EBNA2," Molecular and Cellular Biology, (Mar. 1996). pp. 952-959.
Hu et al., "Direct Conversion of Normal and Alzheimer's Disease Human Fibroblasts into Neuronal Cells by Small Molecules," Cell Stem Cell 17: 204-212, Aug. 6, 2015 (36 pages).
Huang et al., "Direct Reprogramming of Human Fibroblasts to Functional and Expandable Hepatocytes," Cell Stem Cell 14: 370-384, Mar. 6, 2014 (15 pages).
Huang et al., "Induction of functional hepatocyte-like cells from mouse fibroblasts by defined factors," Nature, Jul. 21, 2011, 475: 386-389 (7 pages).
Huch & Clevers, "Sox9 marks adult organ progenitors," Nature Genetics, Jan. 11, 2011, 43(1): 9-10 (3 pages).
Huch et al., In vitro expansion of single Lgr51 liver stem cells induced by Wnt-driven regeneration 2013 Nature 494:247-250 (7 pages).
Huch et al., Long-Term Culture of Genome-Stable Bipotent Stem Cells from Adult Human Liver, (2015) Cell 160:299-312 (24 pages).
Huch et al., "Urokinase-Type Plasminogen Activator Receptor Transcriptionally Controlled Adenoviruses Eradicate Pancreatic Tumors and Liver Metastasis in Mouse Models," NeoPlasia, 11(6): 518-528 (Jun. 2009).
Hughes et al., "Matrigel: A complex protein mixture required for optimal growth of cell culture," (2010) Proteomics, 10(9):1886-90 (6 pages).
Humphries et al., "Integrin Ligands," J Cell Sci., Oct. 1, 2006; 119(Pt 19): 3901-3903 (5 pages).
Humphries, "Integrin Structure," (2000) Biochemical Society Transactions vol. 28, part 4 (31 pages).
Huschtscha et al., "Normal human mammary epithelial cells proliferate rapidly in the pressure of elevated levels of the tumor suppressors p53 and p21WAF1/CIP1," Journal of Cell Science, 122: 2989-2995 (2009).
Hynds et al., "The Relevance of Human Stem Cell-Derived Organoid Models for Epithelial Translational Medicine," Europe PMC Funders Group Stem Cells (Mar. 2013); 11 pages.
Igarashi et al., "Characterization of Recombinant Human Fibroblast Growth Factor (FGF)-10 Reveals Functional Similarities with Keratinocyte Growth Factor (FGF-7)," The Journal of Biological Chemistry (May 1998), 273(21):13230-13235.
International Preliminary Report on Patentability of International Application No. PCT/EP2019/082618, dated Jun. 10, 2021 (13 pages).
Vanuytsel et al., "Major Signaling Pathways in Intestinal Stem Cells," Biochim Biophys Acta. Feb. 2013; 1830(2):2410-2426 (42 pages).
Leonard et al., "Screening of Budesonide Nanoformulations for Treatment of Inflammatory Bowel Disease in an Inflamed 3D Cell-Culture Model," Altex, 29(3):275-285, 2012 (11 pages).
Noben et al., "Human intestinal epithelium in a dish: Current models for research into gastrointestinal pathophysiology," United European Gastroenterology Journal 2017, 5(8): 1073-1081 (9 pages).
Schmohl et al., "Characterization of immunologically active drugs in a novel organotypic co-culture model of the human gut and whole blood," International Immunopharmacology (2012) 14: 722-728 (7 pages).
Vadstrup et al., "Ex Vivo Assay of Intestinal Mucosal Biopsies in Crohn's Disease: Reflects Inflammation and Drug Effects," PLoS One, May 2016 (18 pages).
U.S. Appl. No. 16/078,354, filed Aug. 21, 2018, Johannes Carolus Clevers.
U.S. Appl. No. 16/310,933, filed Dec. 18, 2018, Johannes Carolus Clevers.
U.S. Appl. No. 17/915,771, filed Sep. 29, 2022, Joep Beumer.

(56) References Cited

OTHER PUBLICATIONS

Besser et al., "Modifying interleukin—2 concentrations during culture improves function of T cells for adoptive immunotherapy," Cytotherapy (2009) 11(2):206-217 (12 pages).
Beumer et al., "High-Resolution mRNA and Secretome Atlas of Human Enteroendocrine Cells", Cell, May 13, 2020, 181(6):1291-1306 (40 pages).
Chang-Graham et al., "Human Intestinal Enteroids With Inducible Neurogenin-3 Expression as a Novel Model of Gut Hormone Secretion", Cellular and Molecular Gastroenterology, Sep. 10, 2019, 8(2): 209-229 (21 pages).
Dwyer et al., "A three-dimensional co-culture system to investigate macrophage-dependent tumor cell invasion," Journal of Biological Methods, vol. 3(3), e49, 10 pages (2016).
Gehart et al., "Identification of Enteroendocrine Regulators by Real-Time Single-Cell Differentiation Mapping," Cell 176: 1158-1173, Feb. 21, 2019 (33 pages).
International Search Report and Written Opinion of International Application No. PCT/EP2021/058527, dated Aug. 25, 2021 (23 pages).
Neal et al., "Organoid Modeling of the Tumor Immune Microenvironment," Cell. Dec. 1, 20183; 175(7):1972-1988.e16. doi: 10.1016/j.cell.2018.11.021 (34 pages).
Rulifson et al., "Wnt signaling regulates pancreatic β cell proliferation," PNAS, Apr. 10, 2007, 104(15): 6247-6252 (6 pages).
Sinagoga et al., "Deriving functional human enteroendocrine cells from pluripotent stem cells," Development (2018) 145, dev165795, doi: 10.1242/dev.165795 (11 pages).
Rogoz et al., "A 3-D enteroid-based model to study T-cell and epithelial cell interaction," J Immunol Methods, Jun. 2015; 421:89-95 (13 pages).
Sachs et al., "Intestinal epithelial organoids fuse to form self-organizing tubes in floating collagen gels", Development, Mar. 2017 144:1107-1112 (6 pages).
Sachs et al., "A Living Biobank of Breast Cancer Organoids Captures Disease Heterogenity," Cell 172: 373-386 (Jan. 11, 2018).
Sachs et al., "Long-term expanding human airway organoids for disease modeling, " The EMBO Journal (2019) 38: e100300 (20 pages).
Sadelain et al., "Therapeutic T cell engineering," Nature. 2017 545: 423-431, 9 pages, (May 25, 2017).
Saha et al., "Designing synthetic materials to control stem cell phenotype," (2007) Curr Opin Chem Biol. 11(4):381-387.
Saha et al., "Substrate Modulus Directs Neural Stem Cell Behavior," (2008) Biophysical Journal 95: 4426-4438.
Sangiorgi and Capecchi, "Bmi1 is expressed in vivo in intestinal stem cells," Nat Genet. Jul. 2008 ; 40(7): 915-920.
Santhanam et al., "Upregulated Pathways and Products of Tryptophan Metabolism is Associated with the Neoplastic Transition in the Colon Epithelium," Gastroenterology 2016, 150, 4, suppl 1, p. S492, Su1195 (1 page).
Sarkozi et al., "Oncostatin M is a novel inhibitor of TGF-B1-induced matricellular protein expression," Am J Physiol Renal Physiol, 2011, 301: F1014-F1025.
Sato et al. "Single Lgr5 stem cells build crypt villus structures in vitro without a mesenchymal niche," Nature, May 14, 2009, 459:262-265.
Sato et al., "Long-term Expansion of Epithelial Organoids From Human Colon, Adenoma, Adenocarcinoma, and Barrett's Epithelium," Gastroenterology, 14: 1762-1772 (2011).
Sato et al., "Paneth cells constitute the niche for Lgr5 stem cells in intestinal crypts," Nature. Jan. 20, 2011; 469(7330): 415-418.
Sayers and Elliott, Herpes Simplex Virus 1 Enters Human Keratinocytes by a Nectin-1-Dependent, Rapid Plasma Membrane Fusion Pathway That Functions at Low Temperature J Virol. 2016; 90(22):10379-10389 (11 pages).
Schaub et al., "Evidence against a Stem Cell Origin of New Hepatocytes in a Common Mouse Model of Chronic Liver Injury," Aug. 21, 2014, Cell Rep 8: 933-939 (8 pages).
Schrader et al., "Kallikrein-related peptidase 6 regulates epithelial-to-mesenchymal transition and serves as prognostic biomarker for head and neck squamous cell carcinoma patients," Mol Cancer. 2015; 14:107 (14 pages).
Schuler et al., "Efficient Temporally Controlled Targeted Somatic Mutagenesis in Hepatocytes of the Mouse," 2004 Genesis 39: 167-172 (6 pages).
Schumacher et al., "The use of murine-derived fundic organoids in studies of gastric physiology," J Physiol, Feb. 2015, 593(8):1809-1827 (19 pages).
Sebestyen et al., "RhoB Mediates Phosphoantigen Recognition by Vg9Vd2 T Cell Receptor," Cell Rep. May 31, 2016; 15(9):1973-85 (14 pages).
Sekiya & Suzuki, "Direct conversion of mouse fibroblasts to hepatocyte-like cells by defined factors," Jul. 21, 2011, Nature, 475: 390-395 (6 pages).
Sekiya & Suzuki, "Hepatocytes, Rather than Cholangiocytes, Can Be the Major Source of Primitive Ductules in the Chronically Injured Mouse Liver," The American Journal of Pathology, May 2014, 184(5): 1468-1478 (11 pages).
Sell et al., "Hepatocyte Proliferation and α1,-Fetoprotein in Pregnant, Neonatal, and Partially Hepatectomized Rats," Apr. 1974, Cancer Res 34: 865-871 (8 pages).
Semler et al., "Mechanochemical Manipulation of hepatocyte Aggregation Can Selectively Induce or Repress Liver-Specific Function", Biotechnology and Bioengineering, Sep. 1999, 69(4):359-369.
Shah et al., "Metabolic Imaging of Head and Neck Cancer Organoids," PLoS One, 2017, 12(1):e0170415 (17 pages).
Shaner et al., "A bright monomeric green fluorescent protein derived from Branchiostoma lanceolatum," Nat Methods. 2013, 10(5):407-414 (8 pages).
Shattil et al., "The final steps of integrin activation: the end game," (Apr. 2010) Nature reviews, 11:288-300 (13 pages).
Shi et al., "Directed differentiation of human pluripotent stem cells to cerebral cortex neurons and neural networks," Nat Protoc 7, pp. 1836-1846, 2012 (11 pages).
Shibue et al., "Fatty acid-binding protein 5 regulates diet-induced obesity via GIP secretion from enteroendocrine K cells in response to fat ingestion," Am J Physiol Endocrinol Metab 308: E583-E591, 2015.
Shiina et al., MHC Genotyping in Human and Nonhuman Species by PCR-based Next-Generation Sequencing, Intech, Next Generation Sequencing—Advances, Applications and Challenges, Chapter 3, 31 pages (2016).
Shimizu et al., "Identification of a novel therapeutic target for head and neck squamous cell carcinomas: A role for the heurotensin-neurotensin receptor 1 oncogenic signaling pathway," Int J Cancer. 2008; 123(8):1816-1823 (8 pages).
Simmini S et al., "Transformation of intestinal stem cells into gastric stem cells on loss of transcription factor Cdx2," Nat Commun. 2014; 5:5728 (10 pages).
Si-Tayeb et al., "Highly Efficient Generation of Human Hepatocyte-Like Cells from Induced Pluripotent Stem Cells," 2010, Hepatology 51(1): 297-305 (9 pages).
Smith et al., "Animal models for the study of squamous cell carcinoma of the upperaerodigestive tract: A historical perspective with review of their utility and limitations. Part A. Chemically-induced de novo cancer, syngeneic animal models of HNSCC, animal models of transplanted xenogeneic human tumors, " Int. J. Cancer. 2006, 118(9):2111-22 (12 pages).
Smith et al., "Comparison of Biosequences," Advances in Applied Mathematics 2, (1981), pp. 482-489.
Smits et al., "Immortalized N/TERT keratinocytes as an alternative cell source in 3D human epidermal models," Sci Rep. 2017; 7(1):11838 (14 pages).
Snykers et al., "Differentiation of neonatal rat epithelial cells from biliary origin into immature hepatic cells by sequential exposure to hepatogenic cytokines and growth factors reflecting liver development", Toxicology in Vitro, Apr. 4, 2007, 21: 1325-1331.
Snykers et al., "In Vitro Differentiation of Embryonic and Adult Stem Cells into Hepatocytes: State of the Art," Stem Cells 27:577-605 (2009).

(56) References Cited

OTHER PUBLICATIONS

Soulières D et al., "Buparlisib and paclitaxel in patients with platinum-pretreated recurrent or metastatic squamous cell carcinoma of the head and neck (BERIL-1): a randomised, double-blind, placebo-controlled phase 2 trial," Lancet Oncol. Mar. 2017, 18:323-35 (14 pages).
Spence et al., "Directed differentiation of human pluripotent stem cells into intestinal tissue in vitro," Nature, 470 (7332): 105-109 (Feb. 3, 2011).
Squier et al., "Biology of Oral Mucosa and Esophagus," J Natl Cancer Inst Monogr. 2001; 29:7-15 (9 pages).
Stanger, B., "Cellular Homeostasis and Repair in the Mammalian Liver," 2015, Annu Rev Physiol 77: 179-200 (25 pages).
Stepniak et al., "c-Jun/AP-1 controls liver regeneration by repressing p53/p21 and p38 MAPK activity," (2006) Genes Dev. 20(16):2306-14.
Su et al., "Relating conformation to function in integrin a5B1," (2016) PNAS 113(27): E3872-E3881 (10 pages).
Sun et al., "Integrin activation by talin, kindlin and mechanical forces," Nature Cell Biology, Jan. 2019, 21: 25-31 (7 pages).
Sun et al., "The Progress on the Differentiation of the Stem Cells into Hepatocytes," Medical Recapitulate, vol. 16, No. 9, May 2010 (3 pages).
Supek et al., "REVIGO Summarizes and Visualizes Long Lists of Gene Ontology Terms," PLoS One 6(7): e21800, 9 pages.
Swenson, E., "Direct Conversion of Mouse Fibroblasts to Hepatocyte-Like Cells Using Forced Expression of Endodermal Transcription Factors," 2012 Hepatology 55(1): 316-318 (9 pages).
Takeda et al., "Inter-conversion between intestinal stem cell populations in distinct niches," Science. Dec. 9, 2011; 334(6061): 1420-1424.
Tanaka et al., "Head and neck cancer organoids established by modification of the CTOS method can be used to predict in vivo drug sensitivity," Oral Oncology. 2018, 87: 49-57 (9 pages).
Tanimizu et al., "Notch signaling controls hepatoblast differentiation by altering the expression of liver-enriched transcription factors," Journal of Cell Science, 2014, 117(15): 3165- 3174.
Drakos et al., "Inhibition of p53-Murine Double Minute 2 Interaction by Nutlin-3A Stabilizes p53 and Induces Cell Cycle Arrest and Apoptosis in Hodgkin Lymphoma," Clin Cancer Res 2007; Jun. 1, 2007, 13(11): 3380-3387 (8 pages).
Kucab et al., "Selection of TP53-mutated human TP53 knock-in (Hupki) mouse embryo fibroblasts using the MDM2 inhibitor Nutlin-3a," Mutagenesis, 29(1): 79-96, Abstracts of the 36th Annual Meeting of the United Kingdom Environmental Mutagen Society, Jul. 15-17, 2013 at The University of the West of England, Bristol, UK (18 pages).
Miyachi et al., "Restoration of p53 Pathway by Nutlin-3 Induces Cell Cycle Arrest and Apoptosis in Human Rhabdomyosarcoma Cells," Clin Cancer Res, Jun. 15, 2009, 15(12): 4077-4084 (8 pages).
Villalonga-Planells et al., "Activation of p53 by Nutlin-3a Induces Apoptosis and Cellular Senescence in Human Glioblastoma Multiforme," PLoS One, Apr. 2011, 6(4):e18588 (12 pages).
Zhao Y, et al., Cancer Research, 101st Annual Meeting of the American Association for Cancer Research, AACR 2010, Washington, DC, United States, Apr. 17, 2010-21, (Apr. 15, 2010) 70(8): Supp. Suppl. 1. Abstract No. 4529 (3 pages).
1 Casey et al., "Theory of cell fate," WIREs Syst Biol Med, 2020; 12:e1471 (11 pages).
International Search Report and Written Opinion for International Application No. PCT/EP2015/060815, dated Jul. 28, 2015 (15 pages).
International Search Report and Written Opinion for International Application No. PCT/EP2015/077988, dated Apr. 20, 2016 (13 pages).
International Search Report and Written Opinion for International Application No. PCT/EP2015/077990, mailed Jul. 6, 2016 (17 pages).
International Search Report and Written Opinion of International Application No. PCT/EP2017/054797, dated May 31, 2017 (9 pages).
International Search Report and Written Opinion of International Application No. PCT/EP2017/065101, dated Oct. 6, 2017 (13 pages).
International Search Report and Written Opinion of International Application No. PCT/EP2019/082618, dated Feb. 11, 2020 (15 pages).
International Search Report and Written Opinion of International Application No. PCT/EP2020/057147, dated May 14, 2020 (19 pages).
Janda et al., "Surrogate Wnt agonists that phenocopy canonical Wnt and β-catenin signalling," (2017) Nature, 545 (7653):234-237 (19 pages).
Janssen, and Depoortere, "Nutrient sensing in the gut: new roads to therapeutics? Trends in endocrinology and metabolism," 24:92-100 (2013).
Jeong et al., "Neuregulin-1 induces cancer stem cell characteristics in breast cancer cell lines," Oncology Reports (2014), 32:1218-1224.
Johnson et al., "Relationships between drug activity in NCI preclinical in vitro and in vivo models and early clinical trials," Br J Cancer. 2001; 84(10):1424-31 (8 pages).
Juric et al., "Phosphatidylinositol 3-Kinase a-Selective Inhibition With Alpelisib (BYL719) in PIK3CA-Altered Solid Tumors: Results From the First-in-Human Study," J Clin Oncol. May 1, 2018; 36(13): 1291-1299 (12 pages).
Kamiya et a., "Oncostatin M and hepatocyte growth factor induce hepatic maturation via distinct signaling pathways," FEBS Letters 2001, 492: 90-94 (5 pages).
Kan et al., "MPp53-mediated growth suppression in response to Nutlin-3 in cyclin D1 transformed," Cancer Research (Nov. 2007) 9 pages.
Katsuda et al., Conversion of Terminally Committed Hepatocytes to Culturable Bipotent Progenitor Cells with Regenerative Capacity, Cell Stem Cell 20: 41-55, Jan. 5, 2017 (16 pages).
Ke et al. "Down-regulation of Wnt signaling could promote bone marrow derived mesenchymal stem cells to differentiate into hepatocytes," BBRC, Jan. 2, 2008, 36: 342-348 (7 pages).
Kemp et al., "The Roles of Wnt Signaling in Early Mouse Development and Embryonic Stem Cells", Functional Development and Embryology, 2007, pp. 1-13.
Khetani et al., "Microscale culture of human liver cells for drug development," Nat Biotechnol 26(1): 120-126 (20 pages).
Kijima et al., "Three-Dimensional Organoids Reveal Therapy Resistance of Esphagal and Oropharyngeal Squamous Cell Carinoma Cells," Cellular and Molecular Gastroenterlogy and Hepatology, 7(1): 73-91 (19 pages).
Kim et al., "Mitogenic Influence of Human R-Spondin1 on the Intestinal Epithelium" Science, Aug. 19, 2005, 309:1256-1259.
Kirikoshi et al., "WNT10A and WNT6, Clustered in Human Chromosome 2q35 Region with Head-to-Tail Manner, Are Strongly Coexpressed in SW480 Cells," Biochemical and Biophysical Research Communications (2001), 283: 798-805.
Kogata et al., Neuregulin 3 and Erbb Signalling Networks in Embryonic Mammary Gland Development, J Mammary Gland Biology Neoplasia (2013) 18: 149-154.
Kohno et al., "Effects of hyaluronidase on doxorubicin penetration into squamous carcinoma multicellular tumor spheroids and its cell lethality," J Cancer Res Clin Oncol. 1994; 120(5):293-7 (6 pages).
Koo et al., "Controlled gene expression in primary Lgr5 organoid cultures," Nat Methods. 2012, 9(1): 81-84 (4 pages).
Koo et al., "Stem Cells Marked by the R-Spondin Receptor LGR5," Gastroenterology 2014; 147:289-302.
Korinek et al., "Constitutive Transcriptional Activation by a β-Catenin-Tcf Complex in APC −/− Colon Carcinoma," (1997) Science 275:1784-1787.
Kramer et al., "Small-Molecule Inhibitors of GSK-3: Structural Insights and Their Application to Alzheimer's Disease Models," International Journal of Alzheimer's Disease, vol. 2012, Article ID 381029, 32 pages.

(56) References Cited

OTHER PUBLICATIONS

Kross et al., "Co-culture of Head and Neck Squamous Cell Carcinoma Spheroids with Autologous Monocytes Predicts Prognosis," Scand J Immunol. 2008; 67(4):392-9 (8 pages).
Kuball et al., "Facilitating matched pairing and expression of TCR chains doi:10.1182/blood introduced into human T cells," Blood, 109(6): 2331-2338, 8 pages, (2007).
Aban et al., "Sorafenib sensitizes head and neck squamous cell carcinoma cells to ionizing radiation," Radiotherpy and Oncology, 2013, 109(2);286-292 (7 pages).
Latorre et al., "Enteroendocrine Cells: A Review of Their Role In Brain-Gut Communication," Neurogastroenterol Motil. May 2016 ; 28(5): 620-630.
Lau et al., "The R-spondin protein family," Genome Biol. 2012;13(3):242, 2012 (10 pages).
Lee et al., "Lung stem cell differentiation in mice directed by endothelial cells via a BMP4-NFATc1-Thrombospondin-1 axis," Cell. Jan. 30, 2014; 156(3): 440-455.
Lee et al., "Neuregulin Autocrine Signaling Promotes Self-Renewal of Breast Tumor-Initiating Cells by Triggering HER2/HER3 Activation," Tumor and Stem Cell Biology Cancer Research 74(1):341-52 (2014).
Leemans et al., "The molecular landscape of head and neck cancer," May 2018, Nat. Rev. Cancer, 18(5): 269-282 (14 pages).
Lemaigre et al., "Mechanisms of Liver Development: Concepts for Understanding Liver Disorders and Design of Novel Therapies", Gastroenterology, Jul. 1, 2009, 137(1): 62-79.
Lengauer et al., "Genetic instability in colorectal cancers," Nature. Apr. 10, 1997; 386:623-627 (5 pages).
Levy et al., "Long-term culture and expansion of primary human hepatocytes," 2015 Nat Biotechnol 33: 1264-1271 (10 pages).
Li and Durbin, "Fast and accurate long-read alignment with Burrows-Wheeler transform," Bioinformatics, 2010, 26(5):589-595 (7 pages).
Li et al., "Adult Mouse Liver Contains Two Distinct Populations of Cholangiocytes," Stem Cell Reports, 9: 478-489, Aug. 8, 2017 (12 pages).
Li et al., "Conformational equilibria and intrinsic affinities define integrin activation, " (2017) EMBO 36:629-645 (17 pages).
Li et al., "Hepatoblast-Like Progenitor Cells Derived From Embryonic Stem Cells Can Repopulate Livers of Mice," Gastroenterology 139: 2158-2169 e2158, 2010 (20 pages).
Li et al., "Isolation and Culture of Adult Mouse Hepatocytes," Methods Mol Biol, 633: 185-196, 2010 (12 pages).
Liang et al., "Genetic and Epigenetic Variations in iPSCs: Potential Causes and Implications for Application," Cell Stem Cell 13: 149-159, Aug. 1, 2013 (11 pages).
Lin et al., "Distributed hepatocytes expressing telomerase repopulate the liver in homeostasis and injury," Nature 556: 244-248, Apr. 12, 2018 (7 pages).
Little et al., "Engineering Biomaterials for Synthetic Neural Stem Cell Microenvironments," (2008) Chem. Rev 108: 1787-1796.
Liu et al., "Osteopontin Promotes Hepatic Progenitor Cell Expansion and Tumorigenicity via Activation of β-Catenin in Mice," 2015 Stem Cells 33: 3569-3580 (12 pages).
Love et al., "Moderated estimation of fold change and dispersion for RNA-seq data with DESeq2," Genome Biology, 15: 550, 2014 (21 pages).
Lund et al., "Genetic and epigenetic stability of human pluripotent stem cells," 2012, Nat Rev Genet 13: 732-744 (14 pages).
Luque et al., "Activated Conformations of Very Late Activation Integrins Detected by a Group of Antibodies (HUTS) Specific for a Novel RegulatoryRegion (355-425) of the Common β1 Chain," (1996) J. Bio Chem. 271(19): 11067-11075 (9 pages).
Abud et al., "Growth of intestinal epithelium in organ culture is dependent on EGF signalling" Experimental Cell Research, Academic Press (2005) 303: 252-262.
Afroze et al., "The physiological roles of secretin and its receptor," Ann Transl Med (2013) 1(3):29.
Ahmed et al., "Extracellular Matrix Regulation of Stem Cell Behavior," Curr Stem Cell Rep (2016) 2:197-206 (10 pages).
Aini et al., "Accelerated telomere reduction and hepatocyte senescence in tolerated human liver allografts," Transplant Immunology (2014), 31(2): 55-59 (28 pages).
Al-Lazikani et al., "Standard Conformations for the Canonical Structures of Immunoglobulins," J. Mol. Biol. (1997) 273: 927-948 (22 pages).
Anders and Huber, "Differential expression analysis for sequence count data," Genome Biology 2010, 11:R106.
Andersson et al., "Pharmacokinetics of Cisplatin and Its Monohydated Coplex in Humans," J Pharm Sci. Aug. 1996; 85(8): 824 827 (4 pages).
Anonymous, Wikipedia Article "Secreted frizzled-related protein 1 also known as SFRP1 is a protein which in humans," Wayback Machine, 7 pages (Oct. 14, 2013).
Argiris et al., "Head and neck cancer," Lancet. May 17, 2008; 371(9625): 1695-1709 (32 pages).
Atsushi et al., A comparison of in vitro platinum-DNA adduct formation between carboplatin and cisplatin, Int J Biochem. 1994; 26(8): 1009-1016 (8 pages).
Bahar et al., "Single-cell spatial reconstruction reveals global division of labor in the mammalian liver," Nature. Feb. 16, 2017; 542(7641): 352-356. doi:10.1038/nature21065 (29 pages).
Barker et al., "Identification of stem cells in small intestine and colon by marker gene Lgr5," Nature, 449: 1003-1008 (Oct. 25, 2007).
Barker et al., "Lgr proteins in epithelial stem cell biology," 2013, Development 140: 2484-2494 (11 pages).
Barker et al., "Lgr5+ve Stem Cells Drive Self-Renewal in the Stomach and Build Long-Lived Gastric Units In Vitro," Cell Stem Cell, 6: 25-36 (Jan. 8, 2010).
Barretina et al., "The CancerCell Line Encyclopedia enables predictive modelling of anticancer drug sensitivity," Nature, 2012; 483(7391): 603-607 (8 pages).
Bartfeld et al., "In Vitro Expansion of Human Gastric Epithelial Stem Cells and Their Responses to Bacterial Infection," Gastroenterology. Jan. 2015; 148(1): 126-136.e6. doi:10.1053/j.gastro.2014.09.042 (22 pages).
Bedke et al., "A microplate co-culture assay allows individualised compound efficacy testing in patients derived 3D tumour spheroids and autologous immune cells," European Urology Supplements, Mar. 2017, 16(3): e1474 (2 pages).
Bhosale et al., "Chromosomal Alterations and Gene Expression Changes Associated with the Progression of eukoplakia to Advanced Gingivobuccal Cancer," Transl Oncol. 2017; 10(3):396-409 (14 pages).
Bigorgne et al., "TTC7A mutations disrupt intestinal epithelial apicobasal polarity," J Clin Invest. 2014;124(1):328-337 (11 pages).
Billerbeck et al., Humanized mice efficiently engrafted with fetal hepatoblasts and syngeneic immune cells develop human monocytes and NK cells, J Hepatol. Aug. 2016; 65(2): 334-343. doi:10.1016/j.jhep 2016.04.022 (20 pages).
Bjerknes et al: "Intestinal epithelial stem cells and progenitors" Methods in Enzymology, Academic Press Inc., Jan. 1, 2006, 419: 337-383.
Blanpain et al., Epithelial Stem Cells: Turning over New Leaves,: Cell., Feb. 9, 2007, 128(3): 445-458 (24 pages).
Boj et al., "Organoid Models of Human and Mouse Ductal Pancreatic Cancer," Cell. Jan. 15, 2015; 160(0): 324-338 (28 pages).
Bonner-Weir et al., "The pancreatic ductal epithelium serves as a potential pool of progenitor cells," Pediatric Diabetes, 2004; 5: 16-22 (7 pages).
Booth et al.: "Maintenance of functional stem cells in isolated and cultured adult intestinal epithelium" Experimental Cell Research, Academic Press, Jun. 15, 1999, 249:359-366.
Bossi et al., "Prognostic and predictive value of EGFR in head and neck squamous cell carcinoma," Oncotarget. 2016; vol. 7, No. 45, pp. 74362-74379 (18 pages).
Bottenstein et al., "Growth of a rat neuroblastoma cell line in serum-free supplemented medium," Proc. Natl. Acad. Sci. USA, 76(1): 514-517, (Jan. 1979).
Braakhuis et al., "The Potential of the Nude Mouse Xenograft Model for the Study of Head and Neck Cancer," Arch Otorhinolaryngol. 1984, 239(1):69-79 (11 pages).

(56) References Cited

OTHER PUBLICATIONS

Brewer et al., "Optimized Survival of Hippocampal Neurons in B27-Supplemented Neurobasal, a New Serum-Free Medium Combination", Journal of Neuroscience Research 35:567-576 (1993); 11 pages.
Brockbank et al., "Cryopreservation Guide", https://www.thermofisher.co.nz/Uploads/file/Scientific/Applications/Equipment-Furniture/Cryopreservation-Guide. PDF, 2007, pp. 1-30.
Broutier et al., "Culture and establishment of self-renewing human and mouse adult liver and pancreas 3D organoids and their genetic manipulation," Nat Protoc 2016, 11(9): 1724-1743 (20 pages).
Broutier et al., "Human Primary Liver Cancer-derived Organoid Cultures for disease modelling and drug screening," Nat Med. Dec. 23, 2017(12): 1424-1435 (35 pages).
Buczacki et al., "Intestinal label-retaining cells are secretory percursors expressing Lgr5," Nature, 495(7493): 65-69, Feb. 27, 2013.
Burke et al., "Liver Zonation Occurs Through a-Catenin-Dependent, c-Myc-Independent Mechanism," Gastroenterology, 2009; 136:2316-2324 (12 pages).
Byron et al."Anti-integrin monoclonal antibodies," J Cell Sci. Nov. 15, 2009; 122(Pt 22): 4009-4011 (6 pages).
Cai Y et al., "Dysregulations in the PI3K pathway and targeted therapies for head and neck squamous cell carcinoma," Oncotarget. 2017; 8(13): 2203-22217 (15 pages).
Calderwood et al., "Integrin activation," Journal of Cell Science 117 (5): 657-666, 2004 (10 pages).
Cambridge Dictionary, definition for "sealed", http://dictionary.cambridge.org/US/dictionary/english/sealed , Sep. 24, 2016, p. 1.
Capaccio et al., "Modern management of obstructive salivary diseases", Acta Otorhinolaryngologica Italica, 2007, 27:161-172.
Carraway et al., "Neuregulin-2, a new ligand of ErbB3/ErbB4-receptor tyrosine kinases," Nature vol. 387; (May 29, 1997); 5 pages.
Cassiman et al., "The Vagal Nerve Stimulates Activation of the Hepatic Progenitor Cell Compartment via Muscarinic Acetylcholine Receptor Type 3," American Journal of Pathology, Aug. 2002, 161(2): 521-530 (10 pages).
Castillo-González et al., "Dysregulated cholinergic network as a novel biomarker of poor prognostic in patients with head and neck squamous cell carcinoma," BMC Cancer. 2015; 15:385 (13 pages).
Cavalieri et al., "Efficacy and safety of single-agent pan-human epidermal growth factor receptor (HER) inhibitor dacomitinib in locally advanced unresectable or metastatic skin squamous cell cancer," Eur J Cancer; 97 (2018) pp. 7-15 (9 pages).
Chai et al., "Wnt signaling induces proliferation of sensory precursors in the postnatal mouse cochlea," PNAS, May 22, 2012, 109(21): 8167-8172 (6 pages).
Chakrabarti et al., "Hedgehog Signaling Regulates PDL-1 Expression in Gastric Cancer Cells to Induce Tumor Proliferation", Gastron, Apr. 22, 2017 (2 pages).
Chakrabarti et al., "Hedgehog Signaling Regulates PDL-1 Expression in Gastric Cancer Cells to Induce Tumor Proliferation," Gastroenterology, vol. 152, No. 5, Digestive Disease Week May 2017, Suppl. 1, (2 pages).
Chatterjee et al., Induced Pluripotent Stem (iPS) Cell Culture Methods and Induction of Differentiation into Endothelial Cells. Methods Mol Biol. 2016; 1357:311-327 (16 pages).
Cheng et al., "Central and Peripheral Administration of Secretin Inhibits Food Intake in Mice through the Activation of the Melanocortin System," Neuropsychopharmacology (2011) 36: 459-471.
Chong et al., "The The quest to overcome resistance to EGFR-targeted therapies in cancer," Nat Med. Nov. 2013 ; 19(11): 1389-1400. doi: 10.1038/nm.3388 (28 pages).
Choo, "The HLA System: Genetics, Immunology, Clinical Testing, and Clinical Implications," Yonsei Med J. Feb. 28, 2007; 48(1):11-23 (13 pages).
Tanimizu et al., "Sry HMG Box Protein 9-positive (Sox9+) Epithelial Cell Adhesion Molecule-negative (EpCAM−) Biphenotypic Cells Derived from Hepatocytes Are Involved in Mouse Liver Regeneration," J Biol Chem, 289(11): 7589-7598 (12 pages).
Tarlow et al., "Bipotential Adult Liver Progenitors Are Derived from Chronically Injured Mature Hepatocytes, " Nov. 6, 2014, Cell Stem Cell 15: 605-618 (15 pages).
Terry et al., "Impaired enteroendocrine development in intestinal-specific Islet1 mouse mutants causes impaired glucose homeostasis," Am J Physiol Gastrointest Liver Physiol 307: G979-G991, Sep. 11, 2014.
Tetteh et al., "Replacement of Lost Lgr5-Positive Stem Cells through Plasticity of Their Enterocyte-Lineage Daughters," Cell Stem Cell 18: 203-213, Feb. 4, 2016.
The Cancer Genome Atlas Network, "Comprehensive genomic characterization of head and neck squamous cell carcinomas," Nature. Jan. 29, 2015; 517: 576-582 (7 pages).
The Wnt Family of Secreted Proteins, R&D Systems' 2004 Catalog, 7 pages (Jan. 1, 2004).
Thenappan et al., New Therapeutics Targeting Colon Cancer Stem Cells, Curr Colorectal Cancer Rep, vol. 5, No. 4, 2009 (12 pages).
Tian et al., "Integrin-specific hydrogels as adaptable tumor organoids for malignant Band T cells", Biomaterials, Sep. 11, 2015, 73: 110-119 (21 pages).
Tisato et al., "Upregulation of SOCS-1 by Nutlin-3 in acute myeloid leukemia cells but not in primary normal cells," Clinics (2014) pp. 68-74.
Tojo et al., "The ALK-5 inhibitor A-83-01 inhibits Smad signaling and epithelial-to-mesenchymal transition bytransforming growth factor-β," Cancer Sci , 2005, 96(11): 791-800.
Trierweiler et al., "The transcription factor c-JUN/AP-1 promotes HBV-related liver tumorigenesis in mice," Cell Death and Differentiation 23: 576-582 (2016).
Tsai et al., "LGR4 and LGR5 Function Redundantly During Human Endoderm Differentiation", Cellular and Molecular Gastroenterology and Hepatology, 2016, 2: 648-662.
Tsuchida et al., "Classification of 'activation' antibodies against integrin βI chain," (1997) FEBS Letters 416: 212-21 (5 pages).
Upton et al., "De novo synthesis of T cells from mPB CD34+ cells cultured in a 3-dimensional thymic organoid," Blood 102(11): 279a, Nov. 16, Nov. 16, 2003 (2 pages).
Valyi-Nagy T et al., "Herpes Simplex Virus 1 Infection Promotes the Growth of a Subpopulation of Tumor Cells in Three-Dimensional Uveal Melanoma Cultures," J Virol. Oct. 2018; 92(19): e00700-18 (12 pages).
Van Amerongen et al., "Developmental Stage and Time Dictate the Fate of Wnt/β-Catenin-Responsive Stem Cells in the Mammary Gland," Sep. 7, 2012, Cell Stem Cell 11: 387-400 (14 pages).
Van de Wetering et al., "Prospective Derivation of a Living Organoid Biobank of Colorectal Cancer Patients," Cell, May 7, 2015, 161:933-945 (14 pages).
Van Es et al., "DII1 marks early secretory progenitors in gut crypts that can revert to stem cells upon tissue damage," Nat Cell Biol. Oct. 2012; 14(10): 1099-1104.
Van Es et al., "Notch/γ-Secretase inhibition turns proliferative cells in intestinal crypts and adenomas into goblet cells," vol. 435; 5 pages, Jun. 2005.
Van Jaarsveld RH et al., "Difference Makers: Chromosomal Instability versus Aneuploidy in Cancer," Trends in cancer. 2(10): 561-571 (11 pages).
Vassilev et al., In Vivo Activation of the p53 Pathway by Small-Molecule Antagonist of MDM2, Science. 2004; 303 (5659):844-848 (7 pages).
Vaughan et al., "Lineage-negative Progenitors Mobilize to Regenerate Lung Epithelium after Major Injury," HHS Public Access Nature (Jan. 29, 2015); 25 pages.
Verbeke et al., "Humanization of the mouse mammary gland by replacement of the luminal layer with genetically engineered preneoplastic human cells," Breast Cancer Research (2014) 20 pages.
Zaret et al., "Genetic programming of liver and pancreas progenitors: lessons for stem-cell differentiation," Nature Reviews, May 2009, 9:329-340.
Verma et al., "Sustained Telomere Length in Hepatocytes and Cholangiocytes with Increasing Age in Normal Liver," 2012, Hepatology 56:1510-1520 (11 pages).

(56) References Cited

OTHER PUBLICATIONS

Vickaryous et al., "Human cell type diversity, evolution, development, and classification with special reference to cells derived from the neural crest,": Biol Rev Camb Philos Soc., 81(3):425-55, Aug. 2006 (31 pages).
Vincan et al., "Frizzled-7 dictates three-dimensional organization of colorectal cancer cell carcinoids", Oncogene 2007, 26:2340-2352.
Machogiannis et al., "Patient-derived organoids model treatment response of metastatic gastrointestinal cancers," Science. Feb. 23, 2018; 359(6378): 920-926 (17 pages).
Voronkov et al., "Wnt/beta-Catenin Signaling and Small Molecule Inhibitors," Current Pharmaceutical Design, 19:634-664 (2013).
Voskoglou-Nomikos et al., "Clinical Predictive Value of the in Vitro Cell Line, Human Xenograft, and Mouse Allograft Preclinical," Cancer Models1Clin Cancer Res. 2003, 9(11):4227-39 (14 pages).
Wang et al., "Self-renewing diploid Axin21 cells fuel homeostatic renewal of the liver," Aug. 13, 2015, Nature, 524: 180-185 (18 pages).
Wei et al., Abstract: "Wnt Proteins in Intestinal Epithelial Progenitor Cells," R&D Systems, 2015 (1 page).
Williams et al., The Role of the Wnt Family of Secreted Proteins in Rat Oval "Stem" Cell-Based Liver Regeneration Wnt1 Drives Differentiation, American Journal of Pathology, Jun. 2010, 176(6):2732-2742.
Wouters et al., "Evolution of distinct EGF domains with specific functions," Protein Science (2005) 14: 1091-1103.
Wu et al., "FGF19 Regulates Cell Proliferation, Glucose and Bile Acid Metabolism vai FGFR4-Dependent and Independent Pathways," PLOS One, Mar. 2011, vol. 6, Issue 3, e17868, pp. 1-11.
Yan et al., "Expression profile analysis of head and neck squamous cell carcinomas using data from The Cancer Genome Atlas," Mol Med Rep. 2016; 13(5):4259-4265 (7 pages).
Yan et al., "The intestinal stem cell markers Bmi1 and Lgr5 identify two functionally distinct populations," PNAS 109:2, pp. 466-471 (Jan. 10, 2012).
Yang et al., A Small Molecule Agonist of an Integrin, αLβ2*,S, Yang et al (2006) Journal of biological chemistry, 281(49): 37904-37912 (18 pages).
Yang et al., "Differentiation of Human Induced-Pluripotent Stem Cells into Smooth-Muscle Cells: Two Novel Protocols," PLoS One, 2016; 11(1):e0147155 (11 pages).
Yang et al., "In vitro trans-differentiation of adult hepatic stem cells into pancreatic endocrine hormoneproducing cells," PNAS, Jun. 11, 2002, 99(12):8078-8083.
Yang et al.,Beta-catenin signaling in murine liver zonation and regeneration: A Wnt-Wnt situation! (2014) Hepatology 60(3):964-976.
Yanger et al., "Adult Hepatocytes Are Generated by Self-Duplication Rather than Stem Cell Differentiation," Sep. 4, 2014, Cell Stem Cell 15: 340-349 (10 pages).
Yanger et al., "Robust cellular reprogramming occurs spontaneously during liver regeneration," 2013, Genes Dev 27: 719-724 (8 pages).
Yimlamai et al., "Hippo Pathway Activity Influences Liver Cell Fate," Jun. 5, 2014, Cell, 157(6): 1324-1338 (23 pages).
Yin et al., "Niche-independent high-purity cultures of Lgr5+ intestinal stem cells and their progeny," Nat Methods. Jan. 2014; 11(1): 106-112.
Yokoyama et al., "Regeneration of Mouse Liver after Partial Hepatectomy," 1953 Cancer Res 13: 80-85 (7 pages).
Yoshimura et al., "Vascular endothelial cells and smooth muscle cells mediate carbachol-induced hepatocyte proliferation via muscarinic receptors and IP3/PKC signaling cascades," Cell Biol Int. Apr. 2009; 33(4):516-23.
Yu et al., "Ex vivo culture of circulating breast tumor cells for individualized testing of drug susceptibility, " HHS Public Access Science (Jul. 11, 2014); 345(6193):216-220.
Yu et al., β1-Integrin Orients Epithelial Polarity via Rac1 and Laminin, (Feb. 2005) Molecular Biology of the cell, 16:433-445 (13 pages).
Huch et al., In vitro expansion of single Lgr51 liver stem cells induced by Wnt-driven regeneration 2013 Nature 494: 247-250 and Methods (6 pages).
Seikagaku et al., "Intestinal Epithelial Stem Cells," The Journal of Japanese Biochemical Society, 2013, vol. 85, No. 9, pp. 743-748, (6 pages).
Caporale et al., "Locoregional IL-2 Therapy in the Treatment of Colon Cancer. Cell-induced Lesions of a Murine Model," Anticancer Research 27: 985-990 (2007).
Zauli et al., "MDM2 Antagonist Nutlin-3 Suppresses the Proliferation and Differentiation of Human Pre-Osteoclasts Through a p53-Dependent Pathway," Journal of Bone and Mineral Research vol. 22, No. 10; (2007) 10 pages.
Zhu and Ding, "Study on a 3D Hydrogel-Based Culture Model for Characterizing Growth of Fibroblasts under Viral Infection and Drug Treatment," SLAS Discovery 2017, 22(5): 626-634 (9 pages).
Zhu et al., "Chemical Strategies for Stem Cell Biology and Regenerative Medicine", The Annual Review of Biomedical Engineering, Apr. 20, 2011, 13(1): 73-90.
Zhu et al., "Mouse liver repopulation with hepatocytes generated from human fibroblasts," Apr. 3, 2014, Nature 508 (7494): 93-97 (34 pages).
Zilberberg et al., "A Rapid and Sensitive Bioassay to Measure Bone Morphogenetic Protein Activity," BMC Cell Biology BioMed Central, 8:41 (Sep. 19, 2007), 10 pages.
Zimmerman, "Lung organoid culture," Differentiation; Research in Biological Diversity, 36(1): 86-109 (1987).
Zolk et al., "Transporter Gene Expression in Human Head and Neck Squamous Cell Carcinoma and Associated Epigenetic Regulatory Mechanisms," Am J Pathol. Jan. 2013; 182(1):234-43 (10 pages).
Zong et al., "Notch signaling controls liver development by regulating biliary differentiation," Development 136: 1727-1739 (2009).
Zuo et al., "P63 + Krt5 + distal airway stem cells are essential for lung regeneration, " Nature (2014) 17 pages.
Robinton et al., "The promise of induced pluripotent stem cells in research and therapy," NIH Public Access Nature 481, (May 13, 2013); 24 pages.
Macchiarini et al., "Clinical Transplantation of a Tissue-Engineered Airway," The Lancet (Nov. 19, 2008) 8 pages.
Machiels et al., "Activity and safety of afatinib in a window preoperative EORTC study in patients with squamous cell carcinoma of the head and neck (SCCHN)," Annals of Oncology 29: 985-991, 2018 (7 pages).
Machiels et al., "Afatinib versus methotrexate as second-line treatment in patients with recurrent or metastatic squamous-cell carcinoma of the head and neck progressing on or after platinum-based therapy (LUX-Head & Neck 1): an open-label, randomised phase 3 trial," Lancet Oncol. 2015;16:583-594 (13 pages).
Malato et al., "Fate tracing of mature hepatocytes in mouse liver homeostasis and regeneration," Dec. 2011, J Clin Invest, 121(12): 4850-4860 (11 pages).
Malorni et al., "The antioxidant N-acetyl cysteine protects cultured epithelial cells from menadione-induced cytopathology", Chemico-Biological Interactions, 1995, 96:113-123.
Manandhar et al., "Glucagon-like Peptide-1 (GLP-1) Analogs: Recent Advances, New Possibilities, and Therapeutic Implications," J. Med. Chem. 2015, 58: 1020-1037.
Marquardt et al., "Functional and genetic deconstruction of the cellular origin in liver cancer," Nov. 2015, J Nat Rev Cancer 15: 653-667 (15 pages).
Martin et al., "Modeling antibody hypervariable loops: A combined algorithm," Proc. Natl. Acad. Sci. USA, 86: 9268-9272, Dec. 1989 (5 pages).
Martin-Belmonte et al., "Cell-Polarity Dynamics Controls the Mechanism of Lumen Formation in Epithelial Morphogenesis", Current Biology, 2008, 18:507-513.
Maushagen et al.,"Effects of paclitaxel on permanent head and neck squamous cell carcinoma cell lines and Identification of anti-apoptotic caspase 9b," J Cancer Res Clin Oncol. 2016; 142(6):1261-71.

(56) References Cited

OTHER PUBLICATIONS

Mayer et al., "A Phase Ib Study of Alpelisib (BYL719),a PI3Kα-Specific Inhibitor, with Letrozole in ER+/HER2-Metastatic Breast Cancer," Metastatic Breast Cancer, Clin Cancer Res. Jan. 1, 2017, 23(1): 26-34 (10 pages).
McEwen et al., "Regulation of the Fibroblast Growth Factor Receptor 3 Promoter and Introm I Enhancer by Sp1 Family Transcription Factors," The Journal of Biological Chemistry, 273(9):5349-5357 (Feb. 27, 1998).
MediLexicon Dictionary, http://www.medilexicon.com/medicaldictionary.php?t=63274 , "Organoid", 2006, p. 1.
Meng et al., "Characterization of integrin engagement during defined human embryonic stem cell culture," (2010) The FASEB Journal, 24(4):1056-1065 (17 pages).
Méry et al., "Preclinical models in HNSCC: A comprehensive review," Oral Oncol. 2017, 65:51-56 (6 pages).
Michalopoulos, G., "Liver Regeneration after Partial Hepatectomy," Jan. 2010, Am J Pathol 176(1): 2-13 (13 pages).
Mitaka, Toshihiro, "Reconstruction of hepatic organoid by hepatic stem cells", J. Hepatobiliary Pancreat Sug, Jan. 1, 2002, 9(6):697-703.
Miyajima et al., "Stem/Progenitor Cells in Liver Development, Homeostasis, Regeneration, and Reprogramming," May 1, 2014, Cell Stem Cell 14: 561-574 (14 pages).
Monnet et al., "Selection of IgG variants with increased FcRn binding using random and directed mutagenesis: impact on effector functions," Frontiers in Immunology, vol. 6, Article 39, Feb. 2015 (15 pages).
Morin et al., "Activation of β-Catenin-Tcf-Signaling in Colon Cancer by Mutations in β-Catenin or APC," Science, 275: 1787-1790, Mar. 21, 1997.
Munoz et al., "The Lgr5 intestinal stem cell signature: robust expression of proposed quiescent '+4' cell markers," The EMBO Journal (2012) 31: 3079-3091.
Munster et al., "Abstract A46: Inhibition of PIK3CA with BYL719 canovercome resistance to cetuximab in squamous cellcarcinoma of the head and neck (SCCHN)," Mol Cancer Ther. Jul. 2015; vol. 14, Issue 7 Supplement (4 pages).
Murry et al. "Differentiation of embryonic stem cells to clinically relevant populations: lessons from embryonic development," Cell, 22;132(4):661-80, Feb. 2008 (20 pages).
Naftalin et al., "Progesterone stimulation of fluid absorption by the rat uterine gland", Reproduction 2002, 123:633-638.
Nakamura et al., "Anti-patched-1 Antibodies Suppress Hedgehog Signaling Pathway and Pancreatic Cancer Proliferation," Anticancer Research 27: 3743-3748 (2007).
Nakamura et al., "Molecular cloning and expression of human hepatocyte growth factor," Nov. 23, 1989, Nature 342: 440-443 (4 pages).
Nakamura et al., "Crosstalk between Wnt and Notch signaling in intestinal epithelial cell fate decision," Journal of Gastroenterology, 2007, 42(9):705.
Nakanishi et al., "Dclk1 distinguishes between tumor and normal stem cells in the intestine," 45(1):98-105 (Jan. 2013).
Namkung et al., "Small-molecule activators of TMEM16A, a calcium-activated chloride channel, stimulate epithelial chloride secretion and instestinal constraction," The FASEB Journal (Nov. 25, 2011) 18 pages.
Nault et al., "High frequency of telomerase reverse-transcriptase promoter somatic mutations in hepatocellular carcinoma and preneoplastic lesions," Jul. 26, 2013, Nature Communications, 4: 221 (7 pages).
Nozaki et al. "Co-culture with intestinal epithelial organoids allows efficient expansion and motility analysis of intraepithelial lymphocytes", J Gastroenterol, 51: 206-216 (8 pages) (2016).
Oda et al., "A comprehensive pathway map of epidermal growth factor receptor signaling," Mol Syst Biol. 2005.0010; 2005 (17 pages).
Oeztuerk-Winder et al., "Regulation of Human Lung Alveolar Multipotent Cells by a Novel p38a MAPK/miR-17-92 axis," The EMBO Journal (2012) 31: 3431-3441.
Ornitz et al., "Regulation of the Fibroblast Growth Factor Receptor 3 Promoter and Intron I Enhancer by Sp1 Family Transcription Factors," The Journal of Biological Chemistry (Feb. 27, 1998) 273(9): 5349-5357.
Pasic et al., "Sustained activation of the HER1-ERK1/2-RSK signaling pathway controls myoepithelial cell fate in human mammary tissue," Genes & Development (2011) 25:1641-1653.
Pasic et al., "Sustained activation of the HER1-ERK1/2-RSK signaling pathway controls myoepithelial cell fate in human mammary tissue," Supplementary Material, 18 pages, Genes & Development 25 (2011).
Perez et al., "Comparative cytotoxicity of CI-973, cisplatin, carboplatin and tetraplatin in human ovarian carcinoma cell lines," Int J Cancer. 1991; 48:265-269 (5 pages).
Peterson et al., "Interaction with basement membrane serves to rapidly distinguish growth and differentiation pattern of normal and malignant human breast epithelial cells," Proc. Natl. Acad. Sci., Oct. 1992, 89: 9064-9068.
Pin et al., "Modelling the Spatio-Temporal Cell Dynamics Reveals Novel Insights on Cell Differentiation and Proliferation in the Small Intestinal Crypt," PLoS One, PLoS One 7(5): e37115, 14 pages (May 2012).
Planas-Paz et al., "The RSPO-LGR4/5-ZNRF3/RNF43 module controls liver zonation and size," 2016, Nat Cell Biol 18: 467-479 (22 pages).
Pokharel et al., "Integrin activation by the lipid molecule 25-hydroxycholesterol induces a proinflammatory response," Nature Communications, (2019)10:1482 (17 pages).
Polychronopoulos et al., Structural Basis for the Synthesis of Indirubins as Potent and Selective Inhibitors of Glycogen Synthase Kinase-3 and Cyclin-Dependent Kinases, (2004) J Med Chem 47: pp. 935-946 (12 pages).
Purwada et al., "Modular Immune Organoids with Integrin Ligand Specificity Differentially Regulate Ex Vivo B Cell Activation" ACS Biomater. Sci. Eng., Jan. 2017, 3:214-225 (12 pages).
Pyeon et al., "Production of infectious human papillomavirus independently of viral replication and epithelial cell differentiation," Proc Natl Acad Sci. 2005; 102(26):9311-9316 (6 pages).
Rabinowitz et al., Transforming Growth Factor β Signaling Controls Activities of Human Intestinal CD8+T Suppressor Cells Gastroenterology, Mar. 2013; 144(3):601-612 (13 pages).
Raven et al., "Cholangiocytes act as Facultative Liver Stem Cells during Impaired Hepatocyte Regeneration," Nature. Jul. 20, 2017; 547(7663): 350-354 (35 pages).
Reed, "Plantinum-DNA adduct, nucleotide excision repair and platinum based anti-cancer chemotherapy," Cancer Treat. Rev. 1998. p. 331-44 (14 pages).
Rennert, et al., "A microfluidically perfused three dimensional human liver model", Biomaterials, Aug. 25, 2015 (Aug. 25, 2015), 71: 119-131 (14 pages).
Kim et al., "Engraftment Potential of Spheroid-Forming Hepatic Endoderm Derived from Human Embryonic Stem Cells," Stem Cells and Development, vol. 22, No. 12, 2013, 12 pages.
Tostões et al., "Human Liver Cell Spheroids in Extended Perfusion Bioreactor Culture for Repeated-Dose Drug Testing," Hepatology, 2012, 55(4):1227-1236 (10 pages).
Clarkson et al., "Oral Viral Infections—Diagnosis and Managementg," Dent. Clin. North Am. 2017, 61(2):351-363 (13 pages).
Clevers et al., "Modeling Development and Disease with Organoids," Cell. Jun. 16, 2016;165(7):1586-1597 (12 pages).
Clotman et al., Control of liver cell fate decision by a gradient of TGFβ signaling modulated by Onecut transcription factors (2005) Genes Dev. 19(16): 1849-54.
Co et al., "Controlling Epithelial Polarity: A Human Enteroid Model for Host-Pathogen Interactions," Cell Reports 26: 2509-2520, Feb. 26, 2019 (17 pages).
Cole et al., "Measuring GSK3 Expression and Activity in Cells," (2008) Methods Mol Biol. 468:45-65.
Combined Search and Examination Report issued in GB Application No. GB1819224.5, dated May 29, 2019 (9 pages).

(56) References Cited

OTHER PUBLICATIONS

Crawford et al., "The Notch Response Inhibitor DAPT Enhances Neuronal Differentiation in Embryonic Stem Cell-Derived Embryoid Bodies Independently of Sonic Hedgehog Signaling," Developmental Dynamics, 2007, pp. 236:886-892.
Crosnier et al., "Organizing cell renewal in the intestine: stem cells, signals and combinatorial control", Nature reviews-Genetics, May 2006, 7:349-359.
Cruz-Acuña et al., "Synthetic hydrogels for human intestinal organoid generation and colonic wound repair," Nature Cell Biology, Nov. 2017, 19(11): 1326-1348 (23 pages).
Cuny et al., "Structure-activity relationship study of bone morphogenetic protein (BMP) signaling inhibitors," Bioorg Med Chem Lett. Aug. 1, 2008; 18(15): 4388-4392.
D'Souza et al., "Case-Control Study of Human Papillomavirus and Oropharyngeal Cancer," N Engl J Med. 2007; 356:1944-56 (13 pages).
Daszkiewicz et al., "A 3D image-based quantification of immune cell-tumor spheroid interactions in the presence of checkpoint inhibition," Journal of Clinical Oncology, vol. 35, No. 7_Suppl, Mar. 1, 2017, (6 pages).
Daszkiewicz et al., Abstract 4611: "A 3D in vitro culture-based method to visualize and quantify effects of immuno-modulatory drugs", Proceedings of the American Association for Cancer Research Annual Meeting 2017; Apr. 1-5, 2017; Washington, DC, Apr. 1, 2017 (4 pages).
De Gouville et al., "Inhibition of TGF-b signaling by an ALK5 inhibitor protects rats from dimethylnitrosamine-induced liver fibrosis," British Journal of Pharmacology (2005) 145: 166-177 (12 pages).
De La Coste et al., "Somatic mutations of the β-catenin gene are frequent in mouse and human hepatocellular carcinomas," Proc. Natl. Acad. Sci. USA, 95:8847-8851, Jul. 1998 (5 pages).
De Lau et al., "Lgr5 homologues associate with Wnt receptors and mediate R-spondin signalling," Nature vol. 476 (Aug. 18, 2011); 6 pages.
De Lau et al., "The R-spondin/Lgr5/Rnf43 module: regulator of Wnt signal strength," Genes and Development, 28:305-316 (2014).
Dekkers et al., "A functional CFTR assay using primary cystic fibrosis intestinal organoids," Nature Medicine vol. 19, No. 7 (Jul. 2013); 10 pages.
Dijkstra et al., "Generation of Tumor-Reactive T Cells by Co-culture of Peripheral Blood Lymphocytes and Tumor Organoids," 2018, Cell 174: 1586-1598 (26 pages).
Dollé et al., EpCAM and the biology of hepatic stem/progenitor cells, 2015 Am J Physiol Gastrointest Liver Physiol 308: G233-250 (18 pages).
Dong et al., "The Epithelial-Mesenchymal Transition Promotes Transdifferentiation of Subcutaneously Implanted Hepatic Oval Cells Into Mesenchymal Tumor Tissue," Stem Cells and Development, 2009, 18(9):1293-1298.
Dontu et al., "Role of Notch signaling in cell-fate determination of human mammary stem/progenitor cells," Breast Cancer Research, vol. 6, No. 6 (2004); 11 pages.
Dorrell et al., "Surface Markers for the Murine Oval Cell Response" NIH Public Access Hepatology (Oct. 2008) 17 pages.
Dou et al., "Expanding SCA-1+ mammary stem cell in the presence of oestrogen and growth hormone," Clin Transl Oncol (2012) 14:444-451 (8 pages).
Driehuis & Clevers, "WNT signalling events near the cell membrane and their pharmacological targeting for the treatment of cancer," British Journal of Pharmacology, (2017) 174: 4547-4563 (17 pages).
Driehuis et al., "Oral Mucosal Organoids as a Potential Platform for Personalized Cancer Therapy," Cancer Discov., 2019, 9(7):852-871 (21 pages).
Drost and Clevers, "Organoids in cancer research," Nat Rev Cancer. Jul. 2018; 18: 407-18 (12 pages).
Drost et al., "Organoid culture systems for prostate epithelial and cancer tissue", Nat. Protoc, Jan. 2016 (Jan. 21, 2016), 11(2): 347-358 (25 pages).
Drost et al., "Sequential cancer mutations in cultured human intestinal stem cells," Nature, May 7, 2015, 521: 43-47 (23 pages).
Duncan et al., "The ploidy-conveyor of mature hepatocytes as a source of genetic variation," Nature. Oct. 7, 2010; 467(7316): 707-710 (14 pages).
Dutta et al., "A Key Tyrosine (Y1494) in the β4 Integrin Regulates Multiple Signaling Pathways Important for Tumor Development and Progression," Cancer Res., Nov. 1, 2008, 68(21):8779-8787 (10 pages).
Eccles, "The epidermal growth factor receptor/Erb-B/HER family in normal and malignant breast biology," International Journal of Developmental Biology, University of the Basque Country Pres., 55(7-9): 685-696 (Jan. 1, 2011).
Economopoulou et al., "The emerging role of immunotherapy in head and neck squamous cell carcinoma (HNSCC): anti-tumor immunity and clinical applications," Ann Transl Med. 2016; 4(9): 173 (13 pages).
Eden et al., "Gorilla: a tool for discovery and visualization of enriched GO terms in ranked gene lists," BMC Bioinformatics 2009, 10:48.
Egerod et al., A Major Lineage of Enteroendocrine Cells Coexpress CCK, Secretin, GIP, GLP-1, PYY, and Neurotensin but Not Somatostatin Endocrinology, Dec. 2012, 153(12):5782-5795.
Egles et al., "Integrin-Blocking Antibodies Delay Keratinocyte Re-Epithelialization in a Human Three-Dimensional Wound Healing Model," PlosOne, 5(5): e10528, May 2010, 8 pages.
Engelhardt et al., "Detection of α-foetoprotein in mouse liver differentiated hepatocytes before their progression through S phase," 1976 Nature 263: 146-148.
Freed-Pastor et al., "Mutant p53: one name, many proteins," Genes Dev. 2012, 26(12):1268-1286 (20 pages).
Font-Burgada et al., "Hybrid Periportal Hepatocytes Regenerate the Injured Liver without Giving Rise to Cancer," 2015 Cell 162: 766-779 (15 pages).
Etienne et al., "Visualization of herpes simplex virus type 1 virions using fluorescent colors," J Virol Methods. J Virol Methods. Mar. 2017 ; 241: 46-51 (14 pages).
Evarts et al., "A precursor—product relationship exists between oval cells and hepatocytes in rat liver," Carcinogenesis 8(11): 1737-1740, 1987 (4 pages).
Faas et al., "Virtual nanoscopy: Generation of ultra-large high resolution electron microscopy maps," J Cell Biol. 198 (3): 457-469 (13 pages).
Fan et al. "Cholangiocarcinomas can originate from hepatocytes in mice," J Clin Invest, Aug. 2012, 122(8): 2911-2915 (5 pages).
Farin et al., "Basic and Translational-Alimentary Tract," (2012) Gastroenterology 143:1518-1529.
Farin et al., "Visualization of a short-range Wnt gradient in the intestinal stem-cell niche," Nature, 340 Feb. 18, 2016 (15 pages).
Finnberg et al., "Application of 3D tumoroid systems to define immune and cytotoxic therapeutic responses based on tumoroid and tissue slice culture molecular signatures", Oncotarget, Sep. 15, 2017, 8(40): 66747-66757 (11 pages).
Finnberg et al., Abstract 3990: "Use of 3D tumoroid systems to define immune and cytotoxic therapeutic responses based on tumoroid and tissue slice culture molecular signatures : Cancer Research", Proceedings of the American Association for Cancer Research Annual Meeting 2017; Apr. 1-5, 2017; Washington, DC., Apr. 1, 2017 (4 pages).
Fitzmaurice et al., "Global, Regional, and National Cancer Incidence, Mortality, Years of Life Lost, Years Lived With Disability, and Disability-Adjusted Life-years for 32 Cancer Groups, 1990 to 2015:A Systematic Analysis for the Global Burden of Disease Study," JAMA Oncol. United States; Apr. 1, 2017; 3(4): 524-548 (56 pages).
Basak et al., "Induced quiescence of Lgr5+ stem cells in intestinal organoids enables differentiation of hormone-producing enteroendocrine cells," Cell Stem Cell.; 20 (2), 177-190.e4 (2017).

(56) References Cited

OTHER PUBLICATIONS

Beumer et al., "Enteroendocrine cells switch hormone expression along the crypt-to-villus BMP signalling gradient," Nature Cell Biology. 20 (8), pp. 909-916 (2018).
Blume et al., "Temperature corrected transepithelial electrical resistance (TEER) measurement to quantify rapid changes in paracellular permeability," Die Pharmazie; 65 (1), pp. 19-24 (2010).
Boj et al., "Forskolin-induced swelling in intestinal organoids: An in vitro assay for assessing drug response in cystic fibrosis patients," Journal of Visualized Experiments, 2017 (120), pp. 1-12 (2017).
De Lau et al., "The R-spondin protein family," Genome Biology. 13:242, 10 pages (2012).
Dinter et al., "Pharmacologic strategies for assaying BMP signaling function," Methods Mol Biol; 1891:221-233 (2019).
Grimaldi et al., A Cell Model Suitable for a High-Throughput Screening of Inhibitors of the Wnt/β-catenin pathway, Frontiers in Pharmacology, vol. 9, Article 1160, Oct. 2018 (3 pages).
Gupta et al., "Scaffolding kidney organoids on silk," Tissue Eng Regen Med., May 2019; 13(5): 812-822 (20 pages).
Hosic et al., "Cholinergic Activation of Primary Human Derived Intestinal Epithelium Does Not Ameliorate TNF-a Induced Injury," Cellular and Molecular Bioengineering, vol. 13, No. 5, Oct. 2020 (2020) pp. 487-505 (19 pages).
International Search Report and Written Opinion of International Application No. PCT/EP2022/069354, dated Nov. 1, 2022, (14 pages).
Lian et al., "Directed cardiomyocyte differentiation from human pluripotent stem cells by modulating Wnt/b-catenin signaling under fully defined conditions," Nature Protocols, vol. 8, No. 1, pp. 162-175 (2013).
Martínez-Maqueda, et al., "HT29 Cell Line. in The Impact of Food Bio-Actives on Gut Health: In Vitro and Ex Vivo Models," Verhoeckx, K. et al. (eds), Cham 20 (CH): Springer, 113-124 (2015).
Miao, Y. et al. (Next-generation surrogate Wnts support organoid growth and deconvolute Frizzled pleiotropy in vivo. Cell Stem Cell. 27 (5), 840-851 (2020).
Nantasanti et al., "Disease Modeling and Gene Therapy of Copper Storage Disease in Canine Hepatic Organoids," Stem Cell Reports, vol. 5, pp. 895-907, Nov. 10, 2015 (13 pages).
Nusse et al., Wnt/B-Catenin Signaling, Disease, and Emerging Therapeutic Modalities, Jun. 1, 2017, Cell 169 (6):985-999.
Park et al., "Differential activities and mechanisms of the four R-spondins in potentiating WNT/β-catenin signaling," J. Biol. Chem. 293(25) 9759-9769 (11 pages) (2018).
Romier et al., "New cell-based HTRF® assays for the exploration of Wnt signalling pathway" Cisbio Bioassays, 2015 (1 page).
Sanchez-Duffhues, "Bone morphogenetic protein receptors: Structure, function and targeting by selective small molecule kinase inhibitors," (2020) Bone 138:115472 (13 pages).
Schutgens et al.,"Tubuloids derived from human adult kidney and urine for personalized disease modeling," Nature Biotechnology 37: 303-313, (2019).
Singh et al., "Review on EGFR Inhibitors: Critical Updates," (2016) Mini-Reviews in Medicinal Chemistry 16:1134-1166.
Snyder et al., "Materials and Microenvironments for Engineering the Intestinal Epithelium," Ann Biomed Eng., vol. 48, No. 7, Feb. 4, 2020, pp. 1916-1940.
Srinivasan et al., TEER measurement techniques for in vitro barrier model systems. Journal of Laboratory 5 Automation. 20 (2), 107-126 (2015).
Tran and Zheng, "Modulating the wnt signaling pathway with small molecules," (2017) Protein Science 26:650-661 (12 pages).
Trenker and Jura, "Receptor tyrosine kinase activation: From the ligand perspective," Current Opinion in Cell Biology, 2020, 63:174-185 (12 pages).
Van der Vaart et al., "Modelling of primary ciliary dyskinesia using patient-derived airway organoids," EMBO reports; 2021; 22: e52058 (16 pages).
Van Es et al., "Wnt signalling induces maturation of Paneth cells in intestinal crypts," Nature Cell Biology. 7(4), 381-386 (2005).
Huch et al., Long-Term Culture of Genome-Stable Bipotent Stem Cells from Adult Human Liver, (2015) Cell 160: 299-312 plus Supplemental Information pages S1-S10 and Supplemental tables S1-S5 (29 pages).
Hisha et al., "Establishment of a Novel Lingual Organoid Culture System: Generation of Organoids Having Mature Keratinized Epithelium from Adult Epithelial Stem Cells," Scientific Reports, 3:3224 Nov. 15, 2013 (10 pages).
Jeong et al., "Generating inner ear organoids containing putative cochlear hair cells from human pluripotent stem cells," Cell Death and Disease, (2018) 9(9):922, 2018 (13 pages).
Kaushik et al., "Concise Review: Current Status of Three-Dimensional Organoids as Preclinical Models," Stem Cells 2018; 36: 1329-1340 (12 Pages).
Nie et al., "Directed Differentiation of Mouse Embryonic Stem Cells into Inner Ear Sensory Epithelia in 3D Culture," Ed. Tsuji, T, Organ Reg: 3D Stem Cell Culture Manipulation, Meth Mol Biol 1597: 67-83, 2017.
Velho et al., "Novel Targeted Agents in Head and Neck Squamous Cell Carcinoma," Hematol Oncol Clin N. Am 29 (2015) 993-1009 (17 pages).
Wikipedia, "Head and Neck Anatomy" downloaded from the internet on Jul. 11, 2025 at https://en.wikipedia.org/wiki/Head_and_neck_anatomy, (11 pages).
Yee et al., "Lgr5-EGFP marks taste bud stem/progenitor cells in posterior tongue," Stem Cells, 31(5): 992-1000, May 2013 (15 pages).

* cited by examiner

DM

| Gibco Advanced DMEM/F12 | |
|---|---|
| + | |
| 10 mM | HEPES |
| 1 x | B27 - VitA |
| 1 x | N2 |
| 1.25 mM | n-Acetylcysteine |
| 50 ng/ml | hEGF |
| 10 nM | Gastrin |
| 25 ng/ml | HGF |
| 0.5 uM | A83.01 |
| 25 ng/ml | BMP7 |
| 100 ng/ml | FGF19 |
| 10 uM | DAPT |
| 3 uM | Dexamethasone |

DM+

| Gibco Advanced DMEM/F12 | |
|---|---|
| + | |
| 10 mM | HEPES |
| 1 x | B27-VitA |
| 1 x | N2 |
| 1.25 mM | n-Acetylcysteine |
| 50 ng/ml | hEGF |
| 10 nM | Gastrin |
| 25 ng/ml | HGF |
| 0.5 uM | A83.01 |
| 25 ng/ml | BMP7 |
| 100 ng/ml | FGF19 |
| 10 uM | DAPT |
| 3 uM | Dexamethasone |
| 3 uM | IWP2 |
| 3 uM | Chir |
| 50 uM | iCRT3 |
| 100 uM | Carbachol |

| No positive effect on difference | | |
|---|---|---|
| BMP4 | IL-6 | SQ 22536 |
| Carbamazepin | OSM | Thrombin |
| FH1 | PGE2 | TNF4a |
| FPH1 | Rapamycin | Triiodothyronine |
| GW4064 | Ruxolitinib | Valproic acid |
| H-89 | S-(5'-Adenosyl)-L-methionine | Verteporfin |

DIFFERENTIATION METHOD

CROSS-REFERENCE TO RELATED APPLICATIONS

This application is a divisional of U.S. application Ser. No. 16/078,354, filed Aug. 21, 2018, which is a national phase entry pursuant to 35 U.S.C. § 371 of International Application No. PCT/EP2017/054797, filed Mar. 1, 2017, which claims the benefit of priority of Great Britain Application No. 1603569.3, filed Mar. 1, 2016, each of which is incorporated by reference herein in its entirety for any purpose.

All documents cited herein are incorporated by reference in their entirety.

TECHNICAL FIELD

The invention is in the field of cell culture media and methods, in particular culture media and methods for differentiating progenitor cells, e.g. human epithelial stem cells.

BACKGROUND

There is great interest in culture media and methods for differentiating progenitor cells. Progenitor cells and their differentiated progeny can be used in cellular assays, drug screening, and toxicity assays. Progenitor cells and their differentiated progeny also show promise for cell-based therapies, such as in regenerative medicine for the treatment of damaged tissue. Furthermore, efficient cell culture media are important for providing and maintaining populations of cells for research purposes.

Methods for the long-term culture of progenitor cells or tissue fragments derived from several tissues (e.g. pancreas, colon, intestinal crypts, stomach, liver and prostate) have been described (see WO 2010/090513, WO 2012/014076, WO 2012/168930 and WO 2015/173425). There is a need for improved culture media and methods that result in a higher efficiency of differentiation of progenitor cells and the generation of differentiated cells that more closely reflect corresponding cell types in vivo.

SUMMARY OF THE INVENTION

The invention provides a method for differentiating progenitor cells, wherein said method comprises:

- culturing the cells in a differentiation medium comprising a basal medium and one or more receptor tyrosine kinase ligands, a Notch inhibitor, a glucocorticoid, a TGF-beta inhibitor and one or more Wnt inhibitors.

The invention further provides a method for differentiating progenitor cells, wherein said method comprises:

- culturing the cells in a differentiation medium comprising a basal medium and one or more receptor tyrosine kinase ligands, a Notch inhibitor, a glucocorticoid, a TGF-beta inhibitor and a GSK-3 inhibitor.

The invention further provides a method for differentiating progenitor cells, wherein said method comprises:

- culturing the cells in a differentiation medium comprising a basal medium and one or more receptor tyrosine kinase ligands, a Notch inhibitor, a glucocorticoid, a TGF-beta inhibitor and an AP-1 stimulant.

The invention further provides a method for culturing epithelial stem cells, preferably to obtain an organoid, wherein said method comprises:

- culturing one or more epithelial stem cells in contact with an extracellular matrix in the presence of an expansion medium; preferably wherein the expansion medium comprises a basal medium, and further comprises: one or more receptor tyrosine kinase ligands, one or more Wnt agonist, a TGF-beta inhibitor and a cAMP pathway activator; and
- culturing the one or more expanded epithelial stem cells in a differentiation medium of the invention.

The invention further provides a method for culturing liver epithelial stem cells, preferably to obtain a differentiated liver organoid, and wherein said method comprises:

- culturing one or more liver epithelial stem cells in contact with an extracellular matrix in the presence of an expansion medium; preferably wherein the expansion medium comprises a basal medium, and further comprises: EGF, FGF10, HGF, a Wnt agonist (e.g. Rspondin), Nicotinamide, a TGF-beta inhibitor, forskolin and gastrin; and subsequently
- culturing the one or more expanded liver epithelial stem cells in contact with an extracellular matrix in the presence of a differentiation medium of the invention.

The invention further provides an organoid obtainable or obtained by a method of the invention.

The invention further provides an organoid in which at least 40%, at least 50%, at least 60%, at least 70%, at least 80%, at least 90% or at least 99% of the cells express hepatocyte markers.

The invention further provides an organoid of the invention, or a cell derived from said organoid, for use in medicine.

The invention further provides the use of an organoid of the invention, or a cell derived from said organoid, in a drug discovery screen; toxicity assay; diagnostics; research of tissue embryology, cell lineages, and differentiation pathways; gene expression studies including recombinant gene expression; research of mechanisms involved in tissue injury and repair; research of inflammatory and infectious diseases; studies of pathogenetic mechanisms; or studies of mechanisms of cell transformation and aetiology of cancer.

The invention further provides a pharmaceutical formulation comprising one or more receptor tyrosine kinase ligands, a Notch inhibitor, a glucocorticoid, a TGF-beta inhibitor, a Wnt pathway inhibitor, a GSK3beta inhibitor and an AP-1 stimulant.

A method for screening for a therapeutic or prophylactic pharmaceutical drug or cosmetic, wherein the method comprises:

- contacting a differentiated organoid of the invention with a candidate molecule (or a library of candidate molecules),
- evaluating said organoid for any effects (e.g. any change in the cell, such as a reduction in or loss of proliferation, a morphological change and/or cell death) or a change in organoid (e.g. the organoid size or motility);
- identifying the candidate molecule that causes said effects as a potential drug or cosmetic; and optionally
- preparing said candidate molecule as pharmaceutical or cosmetic.

DETAILED DESCRIPTION

Methods for differentiating progenitor cells from a variety of tissues have previously been described in WO 2010/090513, WO 2012/014076, WO 2012/168930 and WO 2015/173425. The present inventors have surprisingly found that adding a Wnt inhibitor to the culture medium improves the differentiation of progenitor cells, e.g. as exemplified using liver cells (see Example 1). For instance, addition of a Wnt inhibitor to the culture medium can result in the differentiation of a higher proportion of a cell population in an organoid. Furthermore, addition of a Wnt inhibitor can result in the cells in the differentiated organoids more closely resembling differentiated cells (e.g. hepatocytes) in vivo. For example, a greater level of Cyp3A4 expression in the context of liver cells. This is surprising because paneth cell differentiation requires Wnt and mature hepatocytes have active Wnt signalling (see, e.g., Farin et al. (2012) Gastroenterology 143:1518-1529; Yang et al. (2014) Hepatology 60 (3): 964-976 and Gerbal-Chaloin et al. (2014) Molecular Pharmacology 86:624-634). Therefore, it is surprising that it is possible to improve differentiation by blocking this pathway. The inventors have shown that blocking this pathway at any level is useful, such as blocking Wnt secretion or inhibiting β-catenin target gene expression (see further comments under "Wnt inhibitors"). Accordingly, the invention provides the use of a Wnt inhibitor for differentiating progenitor cells, e.g. liver epithelial stem cells.

The present inventors have also unexpectedly found that the addition of a GSK-3 inhibitor to a differentiation medium has advantageous effects. For example, it promotes the differentiation of progenitor cells. For instance, addition of a GSK-3 inhibitor to a culture medium can result in the differentiation of a higher proportion of a cell population in an organoid. Furthermore, addition of a GSK-3 inhibitor can result in the cells in the differentiated organoids more closely resembling differentiated cells (e.g. hepatocytes) in vivo. Accordingly, the invention provides the use of a GSK-3 inhibitor for differentiating progenitor cells, e.g. liver epithelial stem cells. The advantageous effects associated with the addition of a GSK-3 inhibitor to a differentiation medium are enhanced by the inclusion of a Wnt inhibitor that acts downstream of the β-catenin destruction complex. This is surprising because a GSK-3 inhibitor is known to be a Wnt agonist, which has previously been used in media for expanding, instead of differentiating, progenitor cells (e.g. see WO 2010/090513). Moreover, the use of a Wnt inhibitor and a Wnt agonist in combination was not obvious. Accordingly, the invention provides the use of a GSK-3 inhibitor in combination with a Wnt inhibitor that acts downstream of the β-catenin destruction complex for differentiating progenitor cells, e.g. liver epithelial stem cells.

AP-1 is a dimeric transcription factor composed of the products of the Jun and Fos families of genes. The present inventors have surprisingly found that the addition of an AP-1 stimulant (such as a muscarinic acetylcholine receptor agonist) to a differentiation medium has advantageous effects. For example, it promotes the differentiation of progenitor cells. For instance, addition of an AP-1 stimulant (such as a muscarinic acetylcholine receptor agonist) to a culture medium can result in the differentiation of a higher proportion of a cell population in an organoid. Furthermore, addition of an AP-1 stimulant can result in the cells in the differentiated organoids more closely resembling differentiated cells (e.g. hepatocytes) in vivo. This is surprising because AP-1 was previously thought to be linked with proliferation, such as hepatocyte proliferation during liver regeneration (see, e.g., Stepniak et al. 2006). Indeed, AP-1 was previously reported to acts an oncogene during liver carcinogenesis (see, e.g., Trierweiler et al. (2015) Cell Death and Differentiation 1-7). Therefore, the inventors' observation that an AP-1 stimulant can promote differentiation was highly unexpected. Accordingly, the invention provides the use of an AP-1 stimulant for differentiating progenitor cells, e.g. liver epithelial stem cells. The invention also provides the use of a muscarinic acetylcholine receptor agonist for differentiating progenitor cells, e.g. liver epithelial stem cells.

The present inventors have also unexpectedly found that splitting a culture of progenitor cells before culturing the progenitor cells in a differentiation medium has advantageous effects. For example, it promotes the differentiation of progenitor cells. For instance, splitting progenitor cells before culturing them in a differentiation medium can result in the differentiation of a higher proportion of a cell population in an organoid. Furthermore, splitting the culture of progenitor cells before culturing the progenitor cells in a differentiation medium can result in the cells in the differentiated organoids more closely resembling differentiated cells (e.g. hepatocytes) in vivo.

The inventors showed that these improvements to the differentiation method are additive and thus a differentiation method is most improved when the medium comprises a combination of two or more of a Wnt inhibitor, a GSK-3 inhibitor and an AP-1 stimulant, and/or when the culture of progenitor cells is split before differentiation.

Accordingly, there is provided a method for differentiating progenitor cells, wherein said method comprises culturing one or more progenitor cells in a differentiation medium, the differentiation medium comprising a basal medium and further comprising: (a) one or more Wnt inhibitors, (b) one or more GSK-3 inhibitors (and preferably one or more Wnt inhibitors that act downstream of the β-catenin destruction complex) and/or (c) one or more AP-1 stimulants (e.g. one or more muscarinic acetylcholine receptor agonists). The differentiation medium is a differentiation medium of the invention. For instance, in one embodiment, the differentiation medium comprises a basal medium and further comprises one or more Wnt inhibitor (e.g. a Wnt secretion inhibitor, such as IWP-2, and/or an inhibitor of TCF/LEF, such as iCRT3). In another embodiment, the differentiation medium comprises a basal medium and further comprises one or more GSK-3 inhibitor (e.g. CHIR99021) and preferably one or more Wnt inhibitors that act downstream of the β-catenin destruction complex (e.g. iCRT3). In another embodiment, the differentiation medium comprises a basal medium and further comprises one or more AP-1 stimulant (e.g. carbachol). These embodiments are technically compatible and can be combined in any way.

In a preferred embodiment, the differentiation medium of the invention further comprises, in addition to the one or more components described above, one or more, preferably all, of the components in the list: one or more receptor tyrosine kinase ligands (e.g. EGF, HGF and/or FGF19), a Notch inhibitor (e.g. DAPT), a glucocorticoid (e.g. dexamethasone), and a TGF-beta inhibitor (e.g. an ALK5, ALK4 or ALK 7 inhibitor, such as A83-01). The differentiation medium optionally further comprises a BMP pathway activator (e.g. BMP7) and/or gastrin. The differentiation medium is optionally supplemented with N-acetylcysteine, B27 and/or N2. In some embodiments, the differentiation medium of the invention comprises a buffer (e.g. HEPES). In a preferred embodiment, the basal medium is Advanced DMEM/F12 (Gibco).

The differentiation medium of the invention is particularly advantageous for differentiating liver progenitor cells (e.g. liver epithelial stem cells), e.g. as shown in Example 1. This differentiation medium is also expected to be advantageous for tissues closely related to the liver, such as the pancreas, and also for other epithelial tissues. Each of the components of the differentiation medium is described in detail below.

In some embodiments, the method further comprises an expansion step in which the progenitor cells (e.g. epithelial stem cells) are first cultured in an expansion medium before subsequently culturing in a differentiation medium of the invention. There is therefore provided a method for culturing progenitor cells, wherein the method comprises (a) culturing one or more progenitor cells in an expansion medium to obtain an expanded population of progenitor cells (preferably an expansion organoid), and (b) culturing the expanded population progenitor cells or expansion organoid in a differentiation medium of the invention to obtain an differentiated population of progenitor cells (preferably a differentiation organoid).

There is also provided a method for culturing progenitor cells (e.g. epithelial stem cells), wherein said method comprises splitting the culture of progenitor cells before culturing in the presence of a differentiation medium. In some embodiments, this method further comprises an expansion step in which the progenitor cells are cultured in an expansion medium before splitting the cells and then culturing in a differentiation medium of the invention. For instance, there is provided a method for culturing progenitor cells, wherein the method comprises (a) culturing one or more progenitor cells in an expansion medium to obtain an expanded population of progenitor cells (preferably an expansion organoid), (b) splitting the expanded population of progenitor cells or expansion organoid to obtain split progenitor cells, and (c) culturing one or more of the split progenitor cells in a differentiation medium to obtain an differentiated population of progenitor cells (preferably a differentiation organoid). The differentiation medium used is preferably a differentiation medium of the invention as described herein. The advantageous effects of splitting the culture prior to differentiation are thought to be related to the fact that: it results in more complete removal of any previous culture medium, e.g. an expansion medium; and/or, when epithelial organoids are cultured, the splitting results in decreased organoid size prior to differentiation, which might result in better access of cells to the differentiation factors in the differentiation medium. Therefore, in some embodiments, a differentiation method of the invention further comprises the step of removal of any previous culture medium, e.g. removal of the expansion medium prior to differentiation. This may be achieved by splitting the culture and/or by any other method known in the art. In some embodiments, there is a provided a method for culturing progenitor cells, wherein the method comprises (a) culturing one or more progenitor cells in a first culture medium, e.g. an expansion medium, (b) removing the first culture medium, e.g. by splitting the cells, and (c) culturing the one or more progenitor cells in a differentiation medium to obtain an differentiated population of progenitor cells (preferably a differentiation organoid).

Any expansion medium suitable for epithelial cells can be used prior to differentiation. In a preferred embodiment, the expansion medium used is any expansion medium described in WO 2010/090513, WO 2012/014076, WO 2012/168930 or WO 2015/173425.

Accordingly, there is also provided a differentiation medium comprising one or more Wnt inhibitors (e.g. 1, 2, 3, 4, or more than 4), one or more receptor tyrosine kinase ligands (e.g. 1, 2, 3, 4, or more than 4), a Notch inhibitor, a glucocorticoid and a TGF-beta inhibitor.

Accordingly, there is also provided a differentiation medium comprising one or more GSK-3 inhibitors (e.g. 1, 2, 3, 4, or more than 4), one or more receptor tyrosine kinase ligands (e.g. 1, 2, 3, 4, or more than 4), a Notch inhibitor, a glucocorticoid and a TGF-beta inhibitor. In some embodiments, the culture medium further comprises a Wnt inhibitor that acts downstream of the β-catenin destruction complex.

Accordingly, there is also provided a differentiation medium comprising one or more AP-1 stimulants (e.g. 1, 2, 3, 4, or more than 4), one or more receptor tyrosine kinase ligands (e.g. 1, 2, 3, 4, or more than 4), a Notch inhibitor, a glucocorticoid and a TGF-beta inhibitor. In some embodiments, the one or more AP-1 stimulants comprise one or more muscarinic acetylcholine receptor agonists.

In some embodiments, the differentiation medium comprises one or more GSK-3 inhibitors (e.g. 1, 2, 3, 4, or more than 4), one or more Wnt inhibitors (e.g. 1, 2, 3, 4, or more than 4) comprising a Wnt inhibitor that acts downstream of the β-catenin destruction complex, one or more AP-1 stimulants (e.g. 1, 2, 3, 4, or more than 4), one or more receptor tyrosine kinase ligands (e.g. 1, 2, 3, 4, or more than 4), a Notch inhibitor, a glucocorticoid and a TGF-beta inhibitor.

In some embodiments, the one or more GSK-3 inhibitors comprise CHIR99021. In some embodiments, the one or more Wnt inhibitors comprise an inhibitor of Wnt secretion (e.g. IWP-2) and an inhibitor of β-catenin target gene expression (e.g. an inhibitor of the β-catenin:TCF/Lef transcription complex, such as iCRT3). In some embodiments, the one or more AP-1 stimulants comprise one or more muscarinic acetylcholine receptor agonists, such as carbachol. In some embodiments, the one or more receptor tyrosine kinase ligands comprise EGF, HGF and/or FGF (e.g. FGF19). In some embodiments, the Notch inhibitor is DAPT. In some embodiments, the glucocorticoid is dexamethasone. In some embodiments, the TGF-beta inhibitor is A83-01.

In some embodiments, the differentiation medium further comprises a BMP pathway activator, such as BMP7.

In some embodiments, the differentiation medium further comprises gastrin.

In some embodiments, the differentiation medium further comprises N-acetylcysteine. In some embodiments, the differentiation medium further comprises B27, preferably, B27 without vitamin A. In some embodiments, the differentiation medium further comprises N2. In some embodiments, the differentiation medium further comprises a basal medium for animal or human cells is Advanced DMEM/F12 (Gibco).

The invention therefore provides the use of a Wnt inhibitor, a GSK-3 inhibitor and/or an AP-1 stimulant for differentiating progenitor cells. In some embodiments, the progenitor cells (e.g. epithelial stem cells) are from the liver, pancreas, intestine, stomach, prostate, breast, ovarian, salivary gland, hair follicle, skin, oesophagus, ear, bladder or thyroid. In some embodiments, the progenitor cells are from the liver or pancreas. In some embodiments, the epithelial cells are from the liver.

The invention also provides a method for differentiating epithelial stem cells which uses a differentiation medium as described in WO 2010/090513, WO 2012/014076, WO 2012/168930 or WO 2015/173425 to which at least one (e.g. 1, 2, 3, 4, or more than 4) Wnt inhibitor, at least one (e.g. 1, 2, 3, 4, or more than 4) GSK-3 inhibitor, and/or at least one (e.g. 1, 2, 3, 4, or more than 4) AP-1 stimulant is added.

The various embodiments of the invention and their components are discussed below in detail. As the skilled person will appreciate, any of these embodiments are technically compatible and their components may be combined.

Wnt Inhibitors

The Wnt signalling pathway when activated typically prevents β-catenin degradation and enhances β-catenin-mediated signalling. This pathway is defined by a series of events that occur when the cell-surface Wnt receptor complex, comprising a Frizzled receptor and LRP5/6 is activated, usually by an extracellular signalling molecule, such as a member of the Wnt family. This results in the activation of Dishevelled family proteins which inhibit a destruction complex of proteins that degrades intracellular β-catenin. The destruction complex is formed of structural components including APC and axin, to which casein kinases CK1α, δ and ε and GSK-3 are recruited. The destruction complex is thought to phosphorylate β-catenin and to expose it to a ubiquitin ligase, β-TrCP. Ubiquitination of the β-catenin then results in its degradation in the proteasome.

The main effector function of β-catenin is in the nucleus, where it regulates transcription through interaction with various transcription factors, including the TCF/LEF family transcription factors (e.g. Tcf-1, Tcf-3, Tcf-4 and Lef1).

The Wnt pathway is highly regulated. For instance, Wnt signalling is enhanced when Rspondin binds to its receptors (Lgr4, Lgr5 and/or Lgr6). However, two transmembrane E3 ubiquitin ligases, Rnf43 and Znrf3, have been shown to remove Rspondin receptors (e.g. Lgr4, Lgr5 and/or Lgr6) from the cell surface (see, e.g., de Lau et al. 2016). Rspondins are vertebrate-specific Wnt-enhancing agents. In addition, the binding of Dishevelled family proteins to the Frizzled receptor can be inhibited by Dapper family proteins (e.g. Dapper1 and Dapper3). Furthermore, the activity of the destruction complex is thought to be partly regulated by the phosphorylation status of APC, axin and GSK-3. For example, dephosphorylation of APC or axin by phosphatases (e.g. serine/threonine phosphatases such as PP1, PP2C or PP2A) may inhibit β-catenin degradation. In addition, phosphorylation of GSK-3 by kinases (e.g. p38 MAPK, PKA, PKB, PKC, p90RSK or p70S6K) may inhibit GSK-3 activity and so inhibit β-catenin degradation.

The stability of the destruction complex is thought to be partly regulated by two PARPs, Tankyrases 1 and 2. Poly (ADP-ribosyl)ation of axin and auto-poly(ADP-ribosyl) ation by these Tankyrases may promote deoligomerisation of the destruction complex.

In the nucleus, Dishevelled family proteins can form a complex with the histone deacetylase SIRT1, which supports the transcription of Wnt target genes.

A protein that is thought to be key to the secretion of Wnt is the multipass membrane protein Porcupine (Porc), the loss of which results in Wnt accumulating in the endoplasmic reticulum.

The Wnt signalling pathway can be inhibited at many levels and Wnt inhibitors are reviewed in detail in Voronkov and Krauss (2013) Current Pharmaceutical Design 19:634-664.

A Wnt inhibitor is defined as an agent that inhibits TCF/LEF-mediated transcription in a cell or in a population of cells. Accordingly, Wnt inhibitors suitable for use in the invention include:

(1) inhibitors of Wnt secretion (e.g. inhibitors of Porc, such as LGK974, IWP-1 or IWP-2), (2) competitive and non-competitive inhibitors of the interaction between Wnt or Rspondin and their respective receptors (e.g. OMP-18R5, OMP54F28), (3) factors that promote the degradation of components of the Wnt receptor complex, such as LRP (e.g. niclosamide) and factors that promote the degradation of Rspondin receptors, such as Znrf3 and/or Rnf43 or factors that activate Znrf3 and/or Rnf43, (4) inhibitors of Dishevelled family proteins, such as inhibitors that reduce the binding of Dishevelled family proteins to Frizzled receptors and/or components of the destruction complex (e.g. Dapper family proteins, FJ9, sulindac, 3289-8625, J01-017a, NSC668036) or inhibitors that downregulate the expression of Dishevelled family proteins (e.g. niclosamide), (5) factors that promote destruction complex activity, including (a) inhibitors of phosphatases (e.g. PP1, PP2A and/or PP2C) that dephosphorylate components of the destruction complex, such as axin and/or APC (e.g. okadaic acid or tautomycin) and (b) inhibitors of kinases (e.g. p38 MAPK, PKA, PKB, PKC, p90RSK or p70S6K) that phosphorylate GSK-3 (e.g. SB239063, SB203580 or Rp-8-Br-cAMP), (6) inhibitors of the deoligomerisation of the destruction complex, such as inhibitors of Tankyrases 1 and/or 2 (e.g. XAV939, IWR1, JW74, JW55, 2-[4-(4-fluorophenyl) piperazin-1-yl]-6-methylpyrimidin-4(3H)-one or PJ34), and (7) inhibitors of β-catenin target gene expression, including inhibitors of the β-catenin:TCF/Lef transcription complex, such as inhibitors that disrupt the β-catenin: TCF-4 complex (e.g. iCRT3, CGP049090, PKF118310, PKF115-584, ZTM000990, PNU-74654, BC21, iCRT5, iCRT14 or FH535) and inhibitors of the histone deacetylase SIRT1 (e.g. cambinol).

The inventors have surprisingly found that the inclusion of a Wnt inhibitor in a differentiation medium may enhance the differentiation of epithelial stem cells. For example, the inventors found that inclusion of an inhibitor of Wnt secretion (IWP-2) in a differentiation medium increases the expression of hepatocyte markers (e.g. albumin and cyp3A4) in liver organoids (see FIG. 2D). In contrast, they found that addition of Wnt to the differentiation medium resulted in a decrease in albumin expression (see FIG. 2C). This observation was especially surprising because the inventors found that the absence of a Wnt agonist was not enough to achieve these advantageous effects, active inhibition of the Wnt pathway was required. This was highly unexpected because some cell types (e.g. Paneth cells) require autocrine Wnt pathway signalling in vivo for survival.

Accordingly, the differentiation medium of the invention preferably comprises a Wnt inhibitor. Any suitable Wnt inhibitor may be used as described in (1)-(7) above. For instance, in one preferred embodiment, the Wnt inhibitor is an inhibitor of Wnt secretion, such as a Porc inhibitor, e.g. selected from IWP-2, IWP-1 and LGK974. In another preferred embodiment, the Wnt inhibitor is an inhibitor of β-catenin target gene expression, for example, an inhibitor of the β-catenin:TCF/Lef transcription complex or an inhibitor of the histone deacetylase SIRT1 (e.g. cambinol). In some embodiments, the inhibitor of the β-catenin:TCF/Lef transcription complex is an inhibitor that disrupts the β-catenin:TCF-4 complex, for example an inhibitor selected from iCRT3, CGP049090, PKF118310, PKF115-584, ZTM000990, PNU-74654, BC21, iCRT5, iCRT14 and FH535.

In some embodiments, the Wnt inhibitor is selected from IWP-2, OMP-18R5, OMP54F28, LGK974, 3289-8625, FJ9, NSC 668036, IWR1 and XAV939.

In some embodiments, the Wnt inhibitor is selected from iCRT3, PFK115-584, CGP049090, iCRT5, iCRT14 and FH535.

In some embodiments, the Wnt inhibitor is one of the compounds listed in Table 1 below.

TABLE 1
| Wnt inhibitors | | |
|---|---|---|
| Structure | Compound | Target |
| 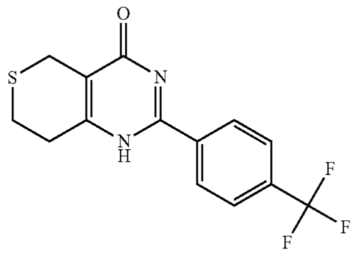 [SMILES: O=c1nc(-c2ccc(C(F)(F)F)cc2)[nH]c2c1CSCC2] | XAV939 | Tankyrases1, 2 |
| 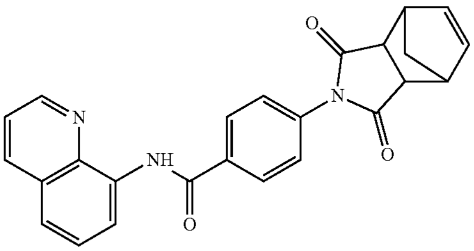 [SMILES: O=C(Nc1cccc2cccnc12)c1ccc(N2C(=O)C3C4C=CC(C4)C3C2=O)cc1] | IWR1 | Tankyrases1, 2 |
| 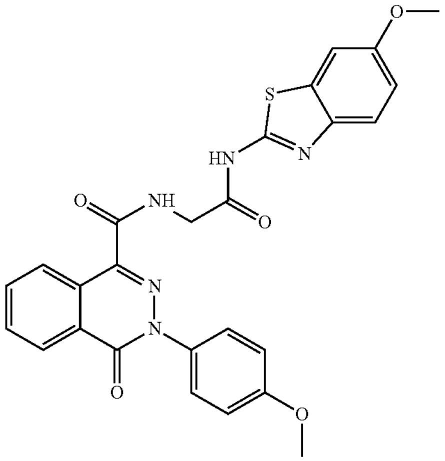 [SMILES: COc1ccc(-n2nc(C(=O)NCC(=O)Nc3nc4ccc(OC)cc4s3)c3ccccc3c2=O)cc1] | IWP-1 | Porcupine |
| 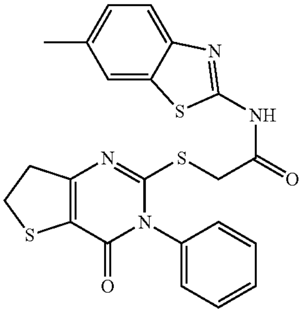 [SMILES: Cc1ccc2nc(NC(=O)CSc3nc4c(c(=O)n3-c3ccccc3)SCC4)sc2c1] | IWP-2 | Porcupine |

TABLE 1-continued
Wnt inhibitors
| Structure | Compound | Target |
|---|---|---|
| 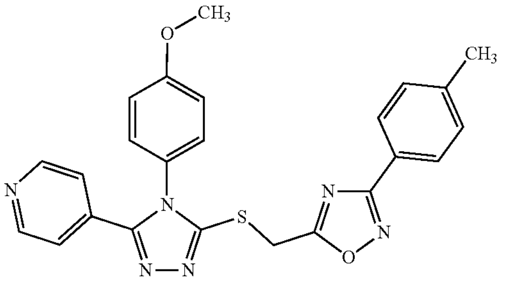 [SMILES: COc1ccc(-n2c(SCc3nc(-c4ccc(C)cc4)no3)nnc2-c2ccncc2)cc1] | JW74 | Tankyrases1, 2 |
| 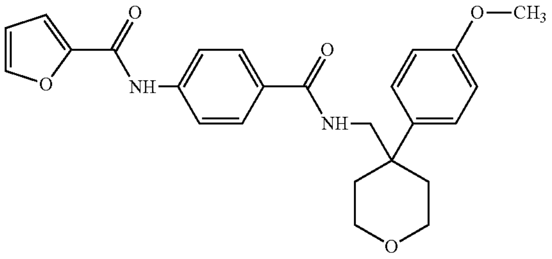 [SMILES: COc1ccc(C2(CNC(=O)c3ccc(NC(=O)c4ccco4)cc3)CCOCC2)cc1] | JW55 | Tankyrases1, 2 |
| 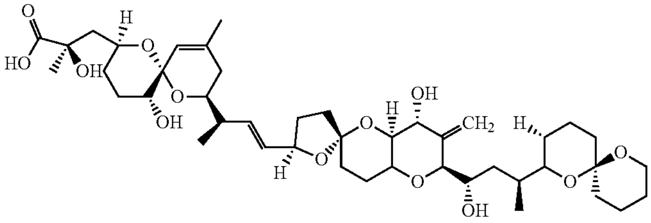 | Okadaic acid | PP2A phosphatase |
| 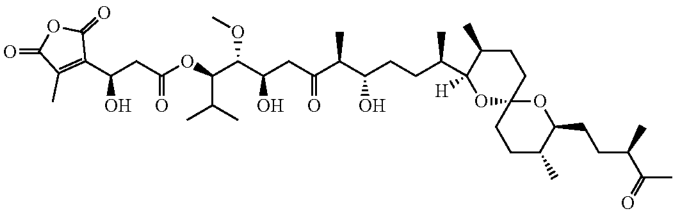 [SMILES: CO[C@H]([C@H](O)CC(=O)[C@@H](C)[C@@H](O)CC[C@@H](C)[C@@H]1O[C@]2(CC[C@@H](C)[C@H](CC[C@@H](C)C(C)=O)O2)CC[C@@H]1C)[C@H](OC(=O)C[C@@H](O)C1=C(C)C(=O)OC1=O)C(C)C] | Tautomycin | PP1 phosphatase |
| 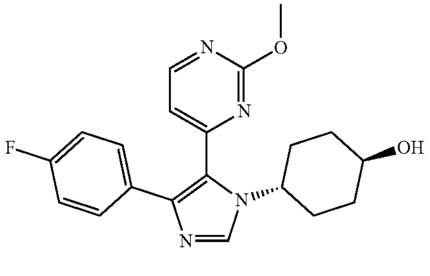 [SMILES: COc1nccc(-c2c(-c3ccc(F)cc3)ncn2[C@H]2CC[C@H](O)CC2)n1] | SB239063 | p38 MAPK |
| 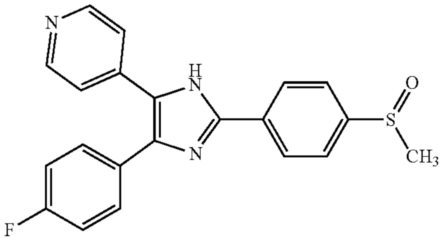 [SMILES: CS(=O)c1ccc(-c2nc(-c3ccc(F)cc3)c(-c3ccncc3)[nH]2)cc1] | SB203580 | p38 MAPK |

TABLE 1-continued
| Wnt inhibitors | | |
|---|---|---|
| Structure | Compound | Target |
| 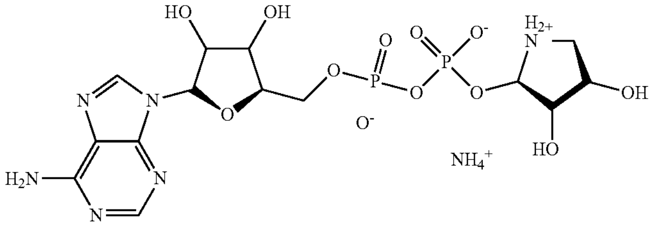 | ADP-HPD | PARG |
| 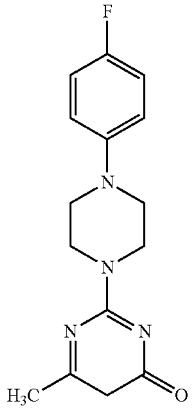 [SMILES: CC1=NC(N2CCN(c3ccc(F)cc3)CC2)=NC(=O)C1] | 2-[4-(4-fluorophenyl) piperazin-1-yl]-6-methylpyrimidin-4(3H)-one | Tankyrases1, 2 |
| 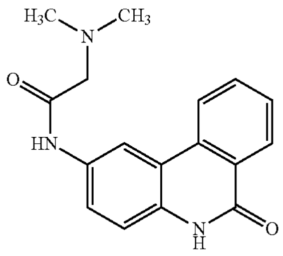 [SMILES: CN(C)CC(=O)Nc1ccc2[nH]c(=O)c3ccccc3c2c1] | PJ34 | Tankyrases1, 2 |
| 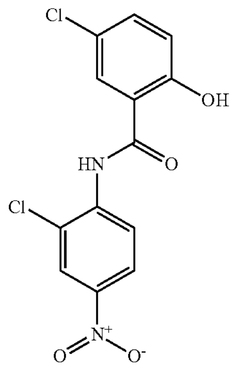 [SMILES: O=C(Nc1ccc([N+](=O)[O-])cc1Cl)c1cc(Cl)ccc1O] | Niclosamide | Downregulates Dvl-2, triggers LRP6 degradation |
| 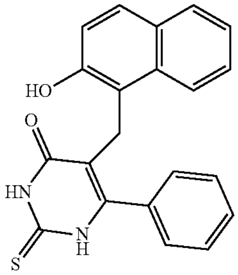 [SMILES: O=c1[nH]c(=S)[nH]c(-c2ccccc2)c1Cc1c(O)ccc2ccccc12] | Cambinol | SIRT1 |

TABLE 1-continued
| Wnt inhibitors | | |
|---|---|---|
| Structure | Compound | Target |
| 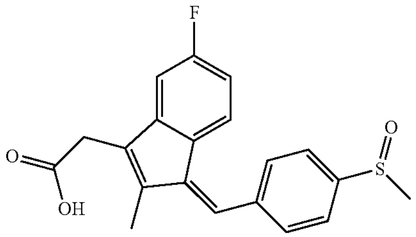 [SMILES: CC1=C(CC(=O)O)c2cc(F)ccc2/C1=C\c1ccc(S(C)=O)cc1] | Sulindac | PDZ domain of Dishevelled |
| 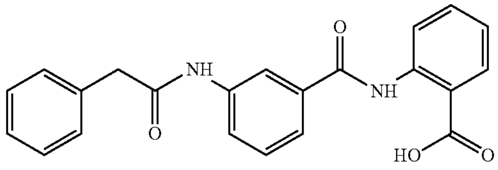 [SMILES: O=C(Cc1ccccc1)Nc1cccc(C(=O)Nc2ccccc2C(=O)O)c1] | 3289-8625 | Dishevelled |
| 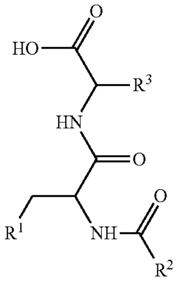 | Scaffold A for series of analogs | Dishevelled |
| 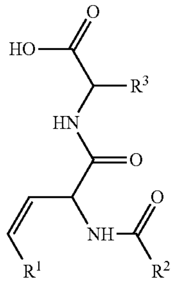 | Scaffold B for series of analogs | Dishevelled |
| 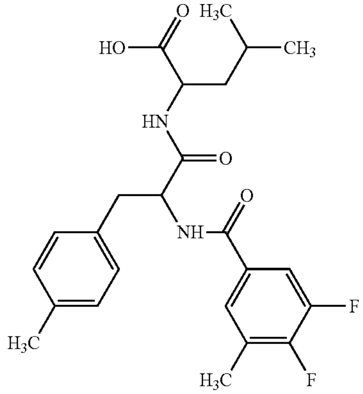 [SMILES: Cc1ccc(CC(NC(=O)c2cc(C)c(F)c(F)c2)C(=O)NC(CC(C)C)C(=O)O)cc1] | J01-017a | Dishevelled |
| 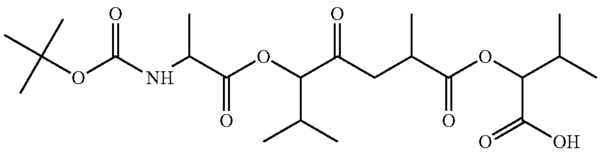 [SMILES: CC(CC(=O)C(OC(=O)C(C)NC(=O)OC(C)(C)C)C(C)C)C(=O)OC(C(=O)O)C(C)C] | NSC668036 | Dishevelled |

TABLE 1-continued
| Wnt inhibitors | | |
|---|---|---|
| Structure | Compound | Target |
| 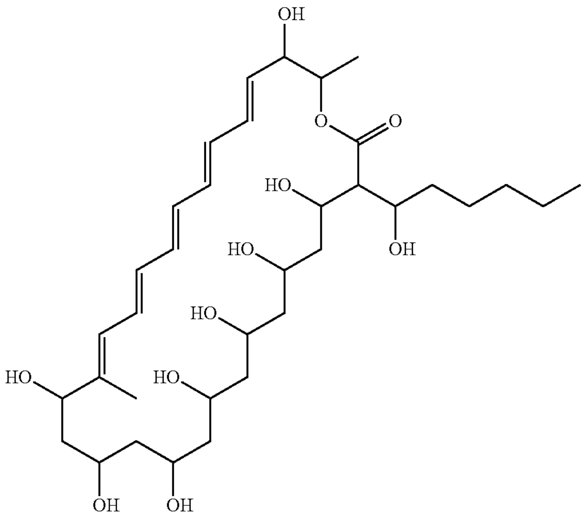 [SMILES: CCCCCC(O)C1C(=O)OC(C)C(O)/C=C/C=C/C=C/C=C/C=C(\C)C(O)CC(O)CC(O)CC(O)CC(O)CC(O)CC1O] | Filipin | Caveolin-mediated endocytosis |
| 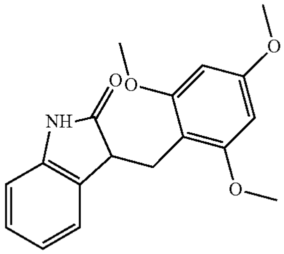 [SMILES: COc1cc(OC)c(CC2C(=O)Nc3ccccc32)c(OC)c1] | IC261 | CK1ε/δ |
| 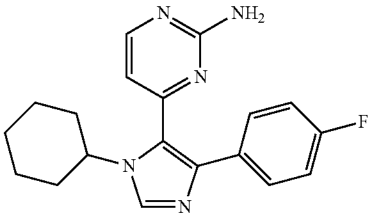 [SMILES: Nc1nccc(-c2c(-c3ccc(F)cc3)ncn2C2CCCCC2)n1] | PF670462 | CK1δ and CK1ε |
| 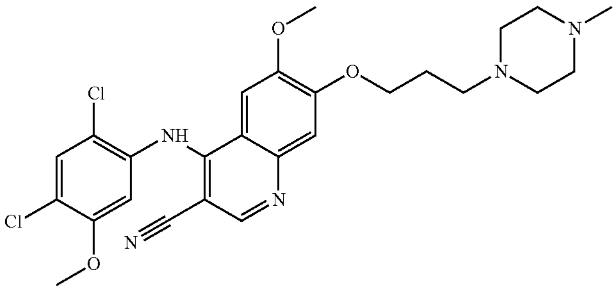 [SMILES: COc1cc(Nc2c(C#N)cnc3cc(OCCCN4CCN(C)CC4)c(OC)cc23)c(Cl)cc1Cl] | Bosutinib | Src kinase |

TABLE 1-continued
| Wnt inhibitors | | |
|---|---|---|
| Structure | Compound | Target |
| 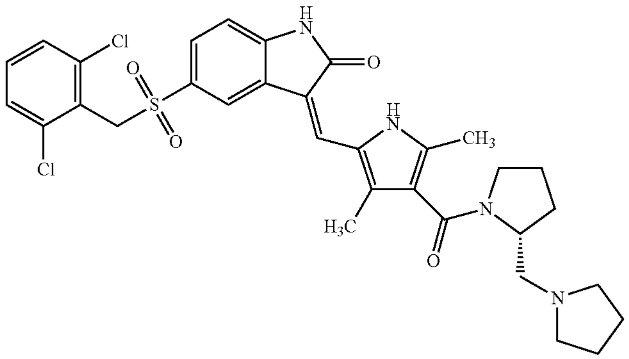 [SMILES: Cc1[nH]c(/C=C2\C(=O)Nc3ccc(S(=O)(=O)Cc4c(Cl)cccc4Cl)cc32)c(C)c1C(=O)N1CCC[C@@H]1CN1CCCC1] | PHA665752 | c-Met |
| 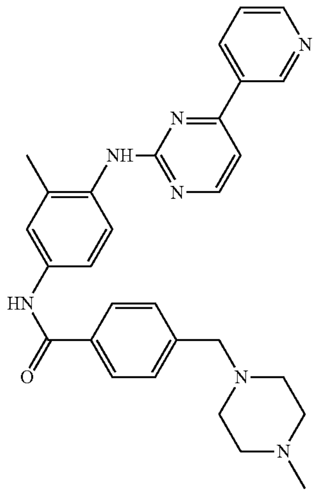 [SMILES: Cc1cc(NC(=O)c2ccc(CN3CCN(C)CC3)cc2)ccc1Nc1nccc(-c2cccnc2)n1] | Imatinib | Different tyrosine kinases |
| 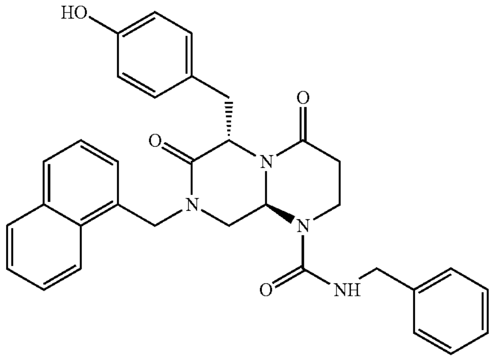 [SMILES: O=C1[C@H](Cc2ccc(O)cc2)N2C(=O)CCN(C(=O)NCc3ccccc3)[C@H]2CN1Cc1cccc2ccccc12] | ICG-001 | CREB binding protein (CBP) |
| 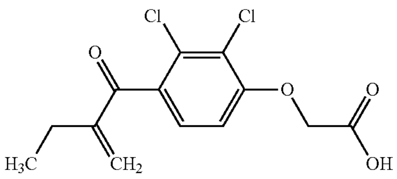 [SMILES: C=C(CC)C(=O)c1ccc(OCC(=O)O)c(Cl)c1Cl] | Ethacrynic acid | Lef-1 |

TABLE 1-continued
| Wnt inhibitors | | |
|---|---|---|
| Structure | Compound | Target |
| 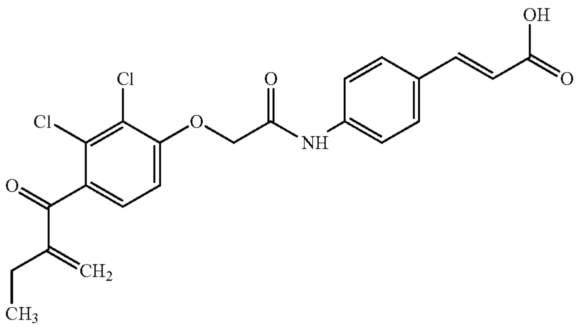 [SMILES: C=C(CC)C(=O)c1ccc(OCC(=O)Nc2ccc(/C=C/C(=O)O)cc2)c(Cl)c1Cl] | Ethacrynic acid derivative | Lef-1 |
| 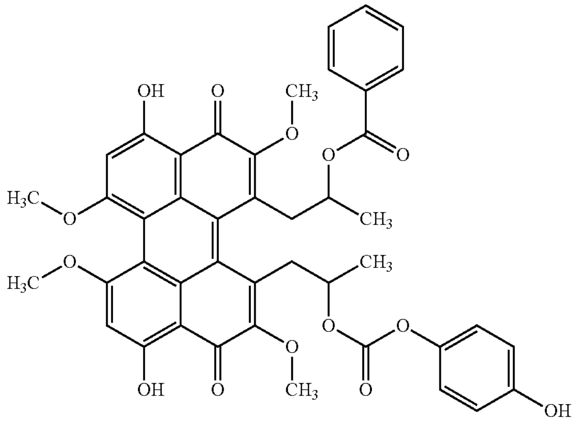 [SMILES: COc1c(CC(C)OC(=O)Oc2ccc(O)cc2)c2c3c(CC(C)OC(=O)c4ccccc4)c(OC)c(=O)c4c(O)cc(OC)c(c5c(OC)cc(O)c(c1=O)c52)c43] | PKF115-584 | β-catenin |
| 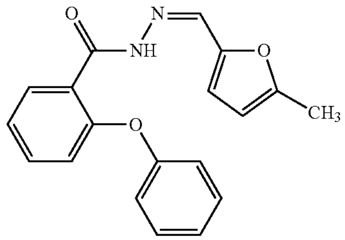 [SMILES: Cc1ccc(/C=N\NC(=O)c2ccccc2Oc2ccccc2)o1] | PNU-74654 | β-catenin |
| 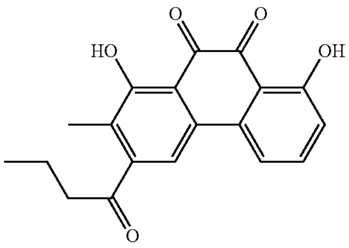 [SMILES: CCCC(=O)c1cc2c(c(O)c1C)C(=O)C(=O)c1c(O)cccc1-2] | PKF118-744 | β-catenin |

TABLE 1-continued
| Wnt inhibitors | | |
|---|---|---|
| Structure | Compound | Target |
| 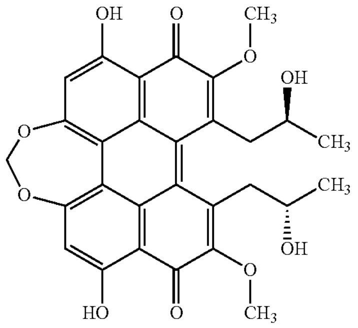 [SMILES: COc1c(C[C@H](C)O)c2c3c(C[C@H](C)O)c(OC)c(=O)c4c(O)cc5c(c6c(cc(O)c(c1=O)c62)OCO5)c43] | CGP049090 | β-catenin |
| 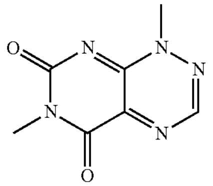 | PKF118-310 | β-catenin |
| 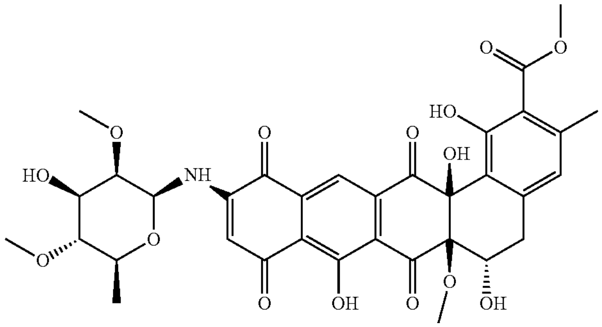 | ZTM000990 | β-catenin |
| 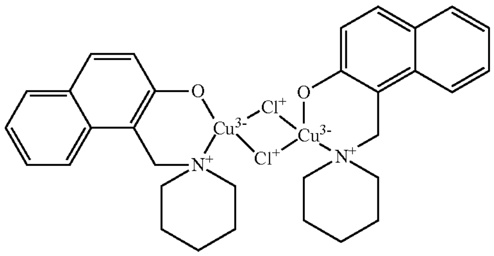 | BC21 | β-catenin |
| 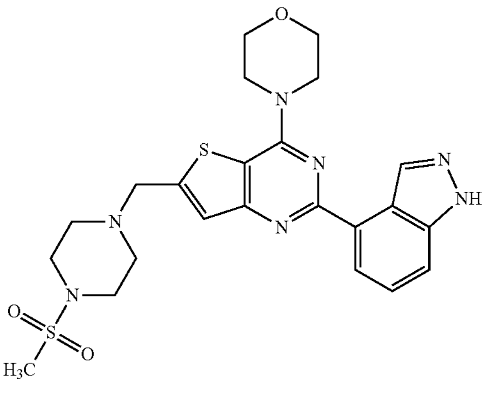 [SMILES: CS(=O)(=O)N1CCN(Cc2cc3nc(-c4cccc5[nH]ncc45)nc(N4CCOCC4)c3s2)CC1] | GDC-0941 | PI3K |

TABLE 1-continued

| Wnt inhibitors | | |
|---|---|---|
| Structure | Compound | Target |
| 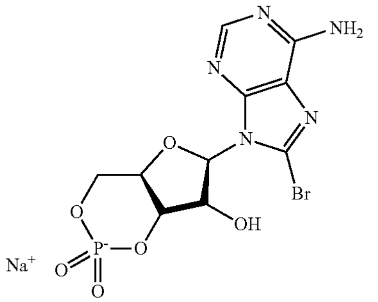 | Rp-8-Br-cAMP | PKA |

In some embodiments, a differentiation medium of the invention comprises one or more of any of the Wnt inhibitors listed in table 1.

The Wnt inhibitor is preferably added to the media in an amount effective to inhibit a Wnt activity in a cell by at least 10%, more preferred at least 20%, more preferred at least 30%, more preferred at least 50%, more preferred at least 70%, more preferred at least 90%, more preferred 100%, relative to a level of said Wnt activity in the absence of said molecule, as assessed in the same cell type. As is known to a skilled person, Wnt activity can be determined by measuring the transcriptional activity of Wnt, for example by pTOPFLASH and pFOPFLASH Tcf luciferase reporter constructs (Korinek et al., 1997. Science 275:1784-1787). New Wnt inhibitors can therefore easily be identified by a skilled person using an assay known in the art.

In some embodiments, the differentiation medium of the invention comprises a Wnt inhibitor at a concentration of 0.01-150 μM, 0.1-150 μM, 0.5-100 μM, 0.1-100 μM, 0.5-50 μM, 1-100 μM or 10-80 μM, 1-20 μM or 1-5 μM.

In some embodiments, the differentiation medium of the invention comprises IWP-2 at a concentration of 0.01-150 μM, 0.1-100 μM, 0.5-50 μM, 1-20 μM or 1-5 μM. For example, in some embodiments, the differentiation medium of the invention comprises IWP-2 at a concentration of about 3 μM.

In some embodiments, the differentiation medium of the invention comprises iCRT3 at a concentration of 0.05-150 μM, 0.1-150 μM, 0.5-100 μM, 1-100 μM or 10-80 μM. For example, in some embodiments, the differentiation medium of the invention comprises iCRT3 at a concentration of about 50 μM. In some embodiments, the differentiation medium of the invention further comprises IWP-2 at a concentration of 0.01-150 μM, 0.1-100 μM, 0.5-50 μM, 1-20 μM, 1-5 μM or about 3 μM. For example, in some embodiments, the differentiation medium of the invention comprises iCRT3 at a concentration of about 50 μM and IWP-2 at a concentration of about 3 μM.

In some embodiments, the differentiation medium does not comprise a Wnt agonist that binds and activates the Wnt receptor complex including any and all of the Wnt family proteins and Rspondin.

GSK-3 Inhibitor

As discussed above, the inventors surprisingly found that the inclusion of Wnt inhibitors in a differentiation medium may enhance the differentiation of epithelial stem cells. Unexpectedly, the inventors also found that the inclusion of a GSK-3 inhibitor (CHIR99021 in Example 1) also improved the differentiation of epithelial stem cells. As explained above, GSK-3 is a component of the β-catenin destruction complex. Inhibiting GSK-3 activity results in reduced destruction of β-catenin, and so GSK-3 inhibitors are Wnt agonists. The enhanced differentiation elicited by the inclusion of a GSK-3 inhibitor in the differentiation medium was greatly increased by the addition of a Wnt inhibitor (iCRT3) that inhibits TCF/LEF-mediated transcription downstream from the destruction complex (see FIG. 2E). Accordingly, the inventors found that there was a pronounced improvement in the expression of hepatocyte markers (albumin and Cyp3A4) when both a Wnt agonist (CHIR99021) and a Wnt inhibitor (iCRT3) are included in a differentiation medium. Without wishing to be bound by any theory, the inventors believe that GSK-3 inhibitors both stimulate and inhibit differentiation in epithelial stem cells (with the stimulation being stronger than the inhibition). The inhibition of differentiation by GSK-3 inhibitors is thought to occur via the promotion of β-catenin destruction. In contrast, the promotion of differentiation by GSK-3 inhibitors is thought to occur by a distinct effector mechanism. Accordingly, the inventors believe that the inclusion of a Wnt inhibitor that inhibits TCF/LEF-mediated transcription downstream from the destruction complex in the GSK-3 inhibitor-comprising differentiation medium counteracts the differentiation-inhibiting effects of the GSK-3 inhibitor. Wnt inhibitors that act downstream of the destruction complex include Wnt inhibitors in class (7) mentioned above, i.e. inhibitors of β-catenin target gene expression, including inhibitors of the β-catenin:TCF/Lef transcription complex, such as inhibitors that disrupt the β-catenin:TCF-4 complex (e.g. iCRT3, CGP049090, PKF118310, PKF115-584, ZTM000990, PNU-74654, BC21, iCRT5, iCRT14 or FH535) and inhibitors of the histone deacetylase SIRT1 (e.g. cambinol).

Thus, the differentiation-promoting effects of GSK-3 inhibitors remain unaffected and are added to by the differentiation-promoting effects of the Wnt inhibitor.

Accordingly, in some embodiments, the differentiation medium of the invention comprises a GSK-3 inhibitor. Any suitable GSK-3 inhibitor may be used. A GSK-3 inhibitor is defined as being an agent that reduces GSK-3 kinase activity.

Two different isoforms of GSK-3 are found in humans (GSK-3α and GSK-3β). Inhibitors are known that inhibit one or both of these isoforms. Accordingly, in some embodiments, the GSK-3 inhibitor inhibits GSK-3α and GSK-3β. In some embodiments, the GSK-3 inhibitor inhibits GSK-3α but does not inhibit GSK-3β. In some embodiments, the GSK-3 inhibitor inhibits GSK-3β but does not inhibit GSK-3α.

In some embodiments, the differentiation medium comprises more than one GSK-3 inhibitor (e.g. two, three, four, five or more GSK-3 inhibitors).

In some embodiments, the GSK-3 inhibitor is CHIR99021.

The GSK-3 inhibitor is preferably added to the media in an amount effective to inhibit a GSK-3 activity in a cell by at least 10%, more preferred at least 20%, more preferred at least 30%, more preferred at least 50%, more preferred at least 70%, more preferred at least 90%, more preferred 100%, relative to a level of said GSK-3 activity in the absence of said molecule, as assessed in the same cell type. As is known to a skilled person, GSK-3 activity can be measured by monitoring phosphorylation of specific GSK-3 substrates, e.g. β-catenin (see, e.g., Cole et al. (2008) Methods Mol Biol. 468:45-65). New GSK-3 inhibitors can therefore easily be identified by a skilled person using an assay known in the art.

In some embodiments, the GSK-3 inhibitor is selected from one or more of the following: CHIR99021, 6-BIO, Dibromocantharelline, Hymenialdesine, Indirubins, Meridianins, CT98014, CT98023, CT99021, TWS119, SB-216763, SB-41528, AR-A014418, AZD-1080, Alsterpaullone, Cazpaullone, Kenpaullone, Aloisines, Manzamine A, Palinurine, Tricantine, TDZD-8, NP00111, NP031115, Tideglusib, HMK-32 and L803-mts.

In some embodiments, the differentiation medium of the invention comprises a GSK-3 inhibitor at a concentration of 0.001-500 μM, 0.01-150 μM, 0.1-100 μM, 1-100 μM, 0.5-50 μM, 1-50 μM, 1-20 μM or 1-5 μM.

In some embodiments, the differentiation medium of the invention comprises CHIR99021 at a concentration of 0.01-150μ, 0.1-100 μM, 1-100 μM, 0.5-50 μM, 1-50 μM, 1-20 μM or 1-5 μM. For example, in some embodiments, the differentiation medium of the invention comprises CHIR99021 at a concentration of about 3 μM.

In some embodiments, the differentiation medium of the invention comprises a GSK-3 inhibitor and a Wnt inhibitor that acts downstream of the destruction complex such as inhibitors of β-catenin target gene expression as described earlier. For example, in some embodiments, differentiation medium of the invention comprises a GSK-3 inhibitor and an inhibitor of β-catenin target gene expression. Inhibitors of β-catenin target gene expression include inhibitors of the β-catenin:TCF/Lef transcription complex, such as inhibitors that disrupt the β-catenin:TCF-4 complex (e.g. iCRT3, CGP049090, PKF118310, PKF115-584, ZTM000990, PNU-74654 or BC21) and inhibitors of the histone deacetylase SIRT1 (e.g. cambinol).

Accordingly, in some embodiments, the differentiation medium of the invention comprises a GSK-3 inhibitor (e.g. at a concentration of 0.001-500 μM, 0.01-150 μM, 0.1-100 μM, 0.5-50 μM, 1-20 M or 1-5 μM) and an inhibitor of β-catenin target gene expression (e.g. at a concentration of 0.001-500 μM, 0.01-150 μM, 0.1-100 μM, 0.5-50 μM, 1-500 μM, 1-150 μM, 1-100 μM, 1-50 μM, 1-20 μM or 1-5 μM). In some embodiments, the inhibitor of β-catenin target gene expression is an inhibitor of the β-catenin:TCF/Lef transcription complex.

Accordingly, in some embodiments, the differentiation medium of the invention comprises CHIR99021 (e.g. at a concentration of 0.01-150 μM, 0.1-100 μM, 0.5-50 μM, 1-20 μM or 1-5 μM) and iCRT3 (e.g. at a concentration of 0.05-150 μM, 0.1-150 μM, 1-150 μM, 0.5-100 μM, 1-100 μM or 10-80 μM). For example, in some embodiments, the differentiation medium of the invention comprises CHIR99021 at a concentration of about 3 μM and iCRT3 at a concentration of about 50 μM.

CHIR99021 Agonists

As explained above, the inventors unexpectedly found that inclusion of a Wnt agonist, CHIR99021, in a differentiation medium promotes differentiation. Accordingly, in some embodiments, the differentiation medium of the invention comprises CHIR99021 or a CHIR99021 agonist. A CHIR99021 agonist is defined herein as being an agent that shares one or more biological activities with CHIR99021.

Accordingly, there is provided a method for differentiating progenitor cells, wherein said method comprises culturing one or more progenitor cells in a differentiation medium, the differentiation medium comprising a basal medium and further comprising CHIR99021 or a CHIR99021 agonist, and preferably one or more Wnt inhibitors that act downstream of the β-catenin destruction complex (e.g. iCRT3). In a preferred embodiment, this differentiation medium further comprises one or more, preferably all, of the components in the list: one or more receptor tyrosine kinase ligands (e.g. EGF, HGF and/or FGF19), a Notch inhibitor (e.g. DAPT), a glucocorticoid (e.g. dexamethasone), and a TGF-beta inhibitor (e.g. an ALK5, ALK4 or ALK 7 inhibitor, such as A83-01). The differentiation medium optionally further comprises one or more, preferably all, of the components in the list: a BMP pathway activator (e.g. BMP7), gastrin, N-acetylcysteine, B27. In some embodiments, the differentiation medium comprises a buffer (e.g. HEPES). In a preferred embodiment, the basal medium for human or animal cells is Advanced DMEM/F12 (Gibco).

The invention also provides the use of CHIR99021 or a CHIR99021 agonist for differentiating progenitor cells, e.g. liver epithelial stem cells.

AP-1 Stimulants

The activating protein 1 (AP-1) complex is a transcription factor that is a heterodimer composed of proteins belonging to the Fos protein family, Jun, ATF and JDP families. This transcription factor regulates gene expression in response to a variety of stimuli including cytokines, growth factors, stress and bacterial and viral infections.

The inventors unexpectedly observed that human liver organoids have a reduced expression of the components of the AP-1 complex in comparison to primary hepatocytes. Based on this observation, they hypothesised that stimulating AP-1 complex formation would promote differentiation of epithelial stem cells in the liver organoids to a hepatocyte fate. The inventors found that including an AP-1 stimulant, carbachol (2-[(Aminocarbonyl)oxy]-N,N,N-trimethylethanaminium chloride), in a differentiation medium increased the expression of hepatocyte markers (including Cyp3A4 and albumin).

The AP-1 stimulant tested by the inventors is a muscarinic acetylcholine receptor agonist. There are five subtypes of muscarinic acetylcholine receptor ($M_1$-$M_5$). These are G-protein-coupled receptors that are found in the cell membranes of various cell types (e.g. neurones).

Accordingly, in some embodiments, the differentiation medium of the invention comprises an AP-1 stimulant. In some embodiments, the AP-1 stimulant is a muscarinic acetylcholine receptor agonist. Any suitable muscarinic acetylcholine receptor agonist may be used. In some embodiments, the muscarinic acetylcholine receptor agonist is an $M_3$ muscarinic acetylcholine receptor agonist (e.g. acetylcholine, bethanechol, carbachol, oxotremorine or pilocarpine).

In some embodiments, the muscarinic acetylcholine receptor agonist is selected from one or more of the following: acetylcholine, bethanecol, carbachol, oxotremorine, L-689,660 (1-azabicyclo[2.2.2]octane, 3-(6-chloropyrazinyl) maleate), pilocarpine, muscarine, McN-A 343 (4-[[[(3-Chlorophenyl)amino]carbonyl]oxy]-N,N,N-trimethyl-2-butyn-1-aminium chloride), 77-LH-218-1 (1-[3-(4-Butyl-1-piperidinyl) propyl]-3,4-dihydro-2(1H)-quinolinone) and methacholine.

In some embodiments, the muscarinic acetylcholine receptor agonist is carbachol.

In some embodiments the AP-1 stimulant (e.g. the muscarinic acetylcholine receptor agonist) is present in the differentiation medium of the invention at a concentration of 0.001-500 μM, 0.01-500 μM, 0.01-250 μM, 0.01-150 μM, 0.1-500 μM, 0.1-100 μM, 0.5-500 μM, 0.5-100 μM, 0.5-50 μM, 1-500 μM, 1-300 μM, 1-200 μM, 1-20 μM, 1-5 μM, 10-300 μM, 50-300 μM, 50-200 μM or 50-150 μM.

In some embodiments, the differentiation medium of the invention comprises carbachol at a concentration of 0.001-500 μM, 0.001-300 μM, 0.01-500 μM, 0.01-300 μM, 0.1-500 μM, 0.1-300 μM, 1-500 μM, 10-500 μM, 100-500 μM, 1-300 μM, 10-300 μM, 50-300 μM, 50-200 μM or 50-150 μM. For example, in some embodiments, the differentiation medium of the invention comprises carbachol at a concentration of 100 μM.

Muscarinic Acetylcholine Receptor Agonists

As explained above, the inventors unexpectedly found that inclusion of a muscarinic acetylcholine receptor agonist, carbachol, in a differentiation medium promotes differentiation. Accordingly, in some embodiments, the differentiation medium of the invention comprises a muscarinic acetylcholine receptor agonist.

Accordingly, there is provided a method for differentiating progenitor cells, wherein said method comprises culturing one or more progenitor cells in a differentiation medium, the differentiation medium comprising a basal medium and further comprising a muscarinic acetylcholine receptor agonist, and preferably one or more Wnt inhibitors that act downstream of the β-catenin destruction complex (e.g. iCRT3). In a preferred embodiment, this differentiation medium further comprises one or more, preferably all, of the components in the list: one or more receptor tyrosine kinase ligands (e.g. EGF, HGF and/or FGF19), a Notch inhibitor (e.g. DAPT), a glucocorticoid (e.g. dexamethasone), and a TGF-beta inhibitor (e.g. an ALK5, ALK4 or ALK 7 inhibitor, such as A83-01). The differentiation medium optionally further comprises one or more, preferably all, of the components in the list: a BMP pathway activator (e.g. BMP7), gastrin, N-acetylcysteine, B27. In some embodiments, the differentiation medium of the invention comprises a buffer (e.g. HEPES). In a preferred embodiment, the basal medium is Advanced DMEM/F12 (Gibco).

Any suitable muscarinic acetylcholine receptor agonist may be used. In some embodiments, the muscarinic acetylcholine receptor agonist is an $M_3$ muscarinic acetylcholine receptor agonist (e.g. acetylcholine, bethanechol, carbachol, oxotremorine or pilocarpine).

In some embodiments, the muscarinic acetylcholine receptor agonist is selected from one or more of the following: acetylcholine, bethanecol, carbachol, oxotremorine, L-689,660 (1-azabicyclo[2.2.2]octane, 3-(6-chloropyrazinyl) maleate), pilocarpine, muscarine, McN-A 343 (4-[[[(3-Chlorophenyl)amino]carbonyl]oxy]-N,N,N-trimethyl-2-butyn-1-aminium chloride), 77-LH-218-1 (1-[3-(4-Butyl-1-piperidinyl) propyl]-3,4-dihydro-2(1H)-quinolinone) and methacholine.

In some embodiments, the muscarinic acetylcholine receptor agonist is carbachol.

In some embodiments the AP-1 stimulant (e.g. the muscarinic acetylcholine receptor agonist) is present in the differentiation medium of the invention at a concentration of 0.001-500 μM, 0.01-500 μM, 0.01-250 μM, 0.01-150 μM, 0.1-500 μM, 0.1-100μ, 0.5-500 μM, 0.5-100 μM, 0.5-50 μM, 1-500 μM, 1-300 μM, 1-200 μM, 1-20 μM, 1-5 μM, 10-300 μM, 50-300 μM, 50-200 μM or 50-150 μM.

In some embodiments, the differentiation medium of the invention comprises carbachol at a concentration of 0.001-500 μM, 0.001-300 μM, 0.01-500 μM, 0.01-300 μM, 0.1-500 μM, 0.1-300 μM, 1-500 μM, 10-500 μM, 100-500 μM, 1-300 μM, 10-300 μM, 50-300 μM, 50-200 μM or 50-150 μM. For example, in some embodiments, the differentiation medium of the invention comprises carbachol at a concentration of 100 μM.

The invention also provides the use of a muscarinic acetylcholine receptor agonist for differentiating epithelial cells, e.g. liver progenitor or stem cells.

Carbachol Agonist

As explained above, the inventors unexpectedly found that inclusion of a muscarinic acetylcholine receptor agonist, carbachol, in a differentiation medium promotes differentiation. Accordingly, in some embodiments, the differentiation medium of the invention comprises carbachol or a carbachol agonist. A carbachol agonist is defined herein as being an agent that shares one or more biological activities with carbachol.

Accordingly, there is provided a method for differentiating epithelial cells, wherein said method comprises culturing one or more epithelial cells in contact with an extracellular matrix in the presence of a differentiation medium, the differentiation medium comprising a basal medium for animal or human cells and further comprises carbachol or a carbachol agonist, and preferably one or more Wnt inhibitors that act downstream of the β-catenin destruction complex (e.g. iCRT3). In a preferred embodiment, this differentiation medium further comprises one or more, preferably all, of the components in the list: one or more receptor tyrosine kinase ligands (e.g. EGF, HGF and/or FGF19), a Notch inhibitor (e.g. DAPT), a glucocorticoid (e.g. dexamethasone), and a TGF-beta inhibitor (e.g. an ALK5, ALK4 or ALK 7 inhibitor, such as A83-01). The differentiation medium optionally further comprises one or more, preferably all, of the components in the list: a BMP pathway activator (e.g. BMP7), gastrin, N-acetylcysteine, B27. In some embodiments, the differentiation medium comprises a buffer (e.g. HEPES). In a preferred embodiment, the basal medium is Advanced DMEM/F12 (Gibco).

The invention also provides the use of carbachol or a carbachol agonist for differentiating progenitor cells, e.g. liver epithelial stem cells.

Receptor Tyrosine Kinase Ligands

Receptor tyrosine kinases (RTKs) are high-affinity cell surface receptors for polypeptide growth factors, cytokines, and hormones. RTKs are key regulators of cell maintenance, growth and development, and also to have a critical role in the development and progression of many types of cancer. A differentiation medium of the invention preferably comprises one or more receptor tyrosine kinase ligand. In the context of the invention, a receptor tyrosine kinase ligand is any ligand that activates an RTK. Many receptor tyrosine kinase ligands are mitogenic growth factors. Thus in some embodiments, the one or more receptor tyrosine kinase ligands in the differentiation medium comprises one or more mitogenic growth factor.

There are approximately 20 different known classes of RTKs, including RTK class I (EGF receptor family) (ErbB family), RTK class II (Insulin receptor family), RTK class III (PDGF receptor family), RTK class IV (FGF receptor family), RTK class V (VEGF receptors family), RTK class VI (HGF receptor family), RTK class VII (Trk receptor family), RTK class VIII (Eph receptor family), RTK class IX (AXL receptor family), RTK class X (LTK receptor family), RTK class XI (TIE receptor family), RTK class XII (ROR receptor family), RTK class XIII (DDR receptor family), RTK class XIV (RET receptor family), RTK class XV (KLG receptor family), RTK class XVI (RYK receptor family), RTK class XVII (MuSK receptor family). In some embodiments, the one or more receptor tyrosine kinase ligands comprises ligands for one or more, or all of these 20 classes of RTKs. In a preferred embodiment, the one or more receptor tyrosine kinase ligands comprises one or more, or all, of a ligand for RTK class I (EGF receptor family) (ErbB family), a ligand for RTK class IV (FGF receptor family), and a ligand for RTK class VI (HGF receptor family). For instance, in some embodiments, the one or more receptor tyrosine kinase ligands comprises a ligand for RTK class I (EGF receptor family) (ErbB family). In some embodiments, the one or more receptor tyrosine kinase ligands comprises a ligand for RTK class IV (FGF receptor family). In some embodiments, the one or more receptor tyrosine kinase ligands comprises a ligand for RTK class VI (HGF receptor family).

Thus, in some embodiments, the one or more receptor tyrosine kinase ligands in the differentiation medium are selected from the group consisting of epidermal growth factor (EGF), fibroblast growth factor (FGF) and hepatocyte growth factor (HGF). In some embodiment, the one or more receptor tyrosine kinase ligands comprises EGF and FGF. In some embodiments, the one or more receptor tyrosine kinase ligands comprises EGF and HGF. In some embodiments, the one or more receptor tyrosine kinase ligands comprises FGF and HGF. In a preferred embodiment, the one or more receptor tyrosine kinase ligands comprises EGF, FGF and HGF. In some embodiments, only one receptor tyrosine kinase ligand is included in the differentiation medium, for example, wherein the receptor tyrosine kinase is selected from FGF, HGF and EGF.

The FGF is preferably an FGF able to bind to FGFR2 or FGFR4 and is preferably FGF19.

Three or more, for example, 3, 4, 5 or more receptor tyrosine kinase ligands may be used in the differentiation media of the invention.

EGF

EGF is a potent mitogenic growth factor for a variety of cultured ectodermal and mesodermal cells and has a profound effect on the differentiation of specific cells in vivo and in vitro and of some fibroblasts in cell culture. The EGF precursor exists as a membrane-bound molecule which is proteolytically cleaved to generate the 53-amino acid peptide hormone that stimulates cells.

Any suitable EGF may be used, for example, EGF obtained from PEPROTECH®. In some embodiments the EGF is human EGF.

EGF is preferably present in the differentiation medium of the invention at a concentration of 0.01-500 ng/ml, 0.1-250 ng/ml, 1-200 ng/ml, 1-100 ng/ml, 10-90 ng/ml or 25-75 ng/ml. A preferred concentration is at least 10, 20, 25, 30, 40, 45, or 50 ng/ml and not higher than 500, 450, 400, 350, 300, 250, 200, 150, or 100 ng/ml. For example, in some embodiments, EGF is added to the basal culture medium at a concentration of about 1-100 ng/ml. In some embodiments, EGF is added to the basal culture medium at a concentration of about 50 ng/ml.

FGF

FGF family members possess broad mitogenic and cell survival activities, and are involved in a variety of biological processes, including embryonic development, cell growth, morphogenesis, tissue repair, tumor growth and invasion. FGFs stimulate cells by interacting with cell surface tyrosine kinase receptors (FGFR). Four closely related receptors (FGFR1-FGFR4) have been identified. FGFR1-FGFR3 genes have been shown to encode multiple isoforms, and these isoforms can be critical in determining ligand specificity. In some embodiments, the FGF is any one of FGF1-10.

Most FGFs bind more than one receptor (Ornitz J Biol Chem. 1998 Feb. 27; 273 (9): 5349-57). In some embodiments, the FGF is an FGF able to bind to FGFR2 and/or FGFR4. In some embodiments, the FGF is an FGF able to bind FGFR4, such as FGF19. For example, in a preferred embodiment, FGF19 is included in the differentiation medium as a receptor tyrosine kinase ligand. In some embodiments, no more than one FGF is used. In other embodiments, two or more FGF are used, e.g. 2, 3 or more. In some embodiments, FGF is substituted with a compound that activates the FGFR2 or FGFR4 pathway (a "FGF-pathway activator"). In some embodiments, FGF is substituted with an alternative compound that activates a FGFR. Accordingly, in some embodiments, FGF is substituted with an FGFR agonist.

FGF is preferably added to the basal culture medium at a concentration of 0.1-500 ng/ml, 0.1-250 ng/ml, 1-200 ng/ml, 10-200 ng/ml or 20-150 ng/ml. For example, in some embodiments, FGF is added to the basal culture medium at a concentration of about 100 ng/ml.

In preparing the differentiation medium, FGF19 is preferably added to the basal culture medium at a concentration of 0.1-500 ng/ml, 0.1-250 ng/ml, 1-200 ng/ml, 10-200 ng/ml or 20-150 ng/ml. Preferred concentrations for FGF19 are about 20, 50, 100, 250, 500 ng/ml, not higher than 500 ng/ml. For example, in some embodiments, FGF19 is added to the basal culture medium at a concentration of about 100 ng/ml.

HGF

Hepatocyte growth factor/scatter factor (HGF/SF) is a morphogenic factor that regulates cell growth, cell motility, and morphogenesis by activating a tyrosine kinase signaling cascade after binding to the proto-oncogenic c-Met receptor. Any suitable HGF may be used, for example, HGF obtained from Peprotech. In some embodiments, HGF is substituted with a compound that activates the HGF receptor. Accordingly, in some embodiments, HGF is substituted with an HGR receptor agonist.

HGF is preferably added to the basal culture medium at a concentration of 0.01-500 ng/ml, 0.1-250 ng/ml, 1-200 ng/ml, 1-100 ng/ml, 10-90 ng/ml or 25-75 ng/ml. Preferred concentrations for HGF are about 1, 10, 20, 25, 50 ng/ml, not higher than 50 ng/ml. For example, in some embodiments, HGF is added to a basal culture medium at a concentration of about 25 ng/ml.

Notch Inhibitor

Notch is a transmembrane surface receptor that can be activated through multiple proteolytic cleavages, one of them being cleavage by a complex of proteins with protease activity, termed gamma-secretase. Gamma-secretase is a protease that performs its cleavage activity within the membrane. Gamma-secretase is a multicomponent enzyme and is composed of at least four different proteins, namely, presenilins (presenilin 1 or 2), nicastrin, PEN-2 and APH-I. Presenilin is the catalytic centre of gamma-secretase. On ligand binding the Notch receptor undergoes a conformational change that allows ectodomain shedding through the action of an ADAM protease which is a metalloprotease. This is followed immediately by the action of the gamma-secretase complex which results in the release of the Notch intracellular domain (NICD). NICD translocates to the nucleus where it interacts with CSL (C-promoter-binding factor/recombinant signal-sequence binding protein JK/Supressor-of-Hairless/Lagl). The binding of NICD converts CSL from a transcriptional repressor to an activator which results in the expression of Notch target genes.

The Notch signalling pathway has previously been implicated in biliary cell fate in vivo. For example, deletion of Rbpj (essential to achieve active Notch signalling) results in abnormal tubulogenesis (Zong Y. Development 2009). In addition, it has previously been shown that inclusion of a Notch inhibitor in a differentiation medium can inhibit biliary duct cell-fate and trigger the differentiation of the cells towards a more hepatocytic phenotype (see WO 2012/168930). In particular, inclusion of a Notch inhibitor (such as DAPT) in a differentiation medium was found to enhance the expression of mature hepatocyte markers and increase the number of hepatocyte-like cells.

Accordingly, preferably, the differentiation medium comprises a Notch inhibitor. Any suitable Notch inhibitor may be used.

In some embodiments, the Notch inhibitor is an inhibitor capable of diminishing ligand mediated activation of Notch (for example via a dominant negative ligand of Notch or via a dominant negative Notch or via an antibody capable of at least in part blocking the interacting between a Notch ligand and Notch), or an inhibitor of ADAM proteases.

In some embodiments the Notch inhibitor is a gamma-secretase inhibitor, for example DAPT, dibenzazepine (DBZ), benzodiazepine (BZ) or LY-411575. One or more Notch inhibitors may be used, for example, 2, 3, 4 or more.

In some embodiments, the Notch inhibitor (e.g. DAPT) is used at a concentration of 0.001-200 μM, 0.01-100 μM, 0.1-50 μM, 0.1-20 μM, 1-100 μM, 1-50 μM, 1-30 μM, 5-100 μM, 5-50 μM or 5-20 μM. For example, in some embodiments, the differentiation medium comprises DAPT at a concentration of about 10 μM.

Glucocorticoid

Glucocorticoids are a class of corticosteroids, which are a class of steroid hormones. Glucocorticoids are corticosteroids that bind to the glucocorticoid receptor. Cortisol is the most important human glucocorticoid. Hydrocortisone is the synthetic version of cortisol. Many other synthetic glucocorticoids with related structures exist (e.g. prednisone, prednisolone, methylprednisolone, dexamethasone, betamethasone, triamcinolone, beclomethasone and fludrocortisone acetate). Glucocorticoids have varying potency for activating a glucocorticoid receptor. This is called the glucocorticoid potency and is usually measured in comparison to cortisol. The biochemistry, pharmacology and mechanism of action of various glucocorticoids are reviewed in, for example, Cecil Textbook of Medicine (1988), pages 128-130, and The Science and Practice of Pharmacy 20th Edition (2000), pages 1363-1370.

Preferably, the differentiation medium comprises a glucocorticoid. Any suitable glucocorticoid may be used. In some embodiments, the glucocorticoid is selected from one or more of the following: cortisol, cortisone, hydrocortisone acetate, hydrocortisone hydrochloride, hydrocortisone valerate, prednisone, prednisolone, methylprednisolone, dexamethasone, betamethasone, betamethasone dipropionate, betamethasone valerate, triamcinolone, triamcinolone acetonide, beclomethasone, beclomethasone dipropionate, fludrocortisone, fludrocortisone acetate, fluticasone, fluticasone acetonide, fluticasone propionate, flunisolide, budesonide, clobetasol, clobetasol propionate, difluorasone, difluorasone diacetate, halobetasol, halobetasol propionate, amcinonide, desoximetasone, fluocinonide, fluocinonide acetonide, halcinonide, mometasone, mometasone furoate, fluandrenolide, prednicarbate, aclometasone, aclometasone dipropionate, desonide, flucinolone, flucinolone acetonide, pramoxine and pramoxine hydrochloride.

Dexamethasone is one of the most potent glucocorticoids and is a preferred glucocorticoid for use in the differentiation medium of the invention. In some embodiments, the glucocorticoid is any glucocorticoid with the same or higher glucocorticoid potency than dexamethasone.

Betamethasone and fludrocortisone acetate are also highly potent glucocorticoids. Accordingly, betamethasone is a preferred glucocorticoid for use in the differentiation medium of the invention. In some embodiments, the glucocorticoid is any glucocorticoid with the same or higher glucocorticoid potency than betamethasone. Accordingly, fludrocortisone acetate is a preferred glucocorticoid for use in the differentiation medium of the invention. In some embodiments, the glucocorticoid is any glucocorticoid with the same or higher glucocorticoid potency than fludrocortisone acetate.

In some embodiments, the glucocorticoid is any glucocorticoid with the same or higher glucocorticoid potency than cortisol.

A list of exemplary glucocorticoids for use in the differentiation medium of the invention is provided below. The potency presented refers to oral dosing.

| Glucocorticoid | Glucocorticoid potency |
|---|---|
| Cortisol (hydrocortisone) | 1 |
| Cortisone | 0.8 |
| Prednisone | 3.5-5 |
| Prednisolone | 4 |
| Methylprednisolone | 5-7.5 |
| Dexamethasone | 25-80 |
| Betamethasone | 25-30 |
| Triamcinolone | 5 |
| Fludrocortisone acetate | 15 |

In some embodiments, the glucocorticoid (e.g. dexamethasone) is used at a concentration of 0.01-150 μM, 0.1-15 μM, 0.5-10 μM or 1-5 μM. In a preferred embodiment, the glucocorticoid is dexamethasone. For example, in some embodiments, the differentiation medium comprises dexamethasone at a concentration of about 3 μM.

TGF-Beta Inhibitor

TGF-beta signalling is involved in many cellular functions, including cell growth, cell fate and apoptosis. Signalling typically begins with binding of a TGF-beta superfamily ligand to a type II receptor which recruits and phosphorylates a type I receptor. The type I receptor then phosphorylates SMADs, which act as transcription factors in the nucleus and regulate target gene expression.

The TGF-beta inhibitor signalling pathway has previously been implicated in biliary cell fate in vivo. For example, the addition of TGF-beta to liver explants facilitates the biliary differentiation in vitro (Clotman et al. (2005) Genes Dev. 19 (16): 1849-54). In addition, it has previously been shown that inclusion of a TGF-beta inhibitor in a differentiation medium can inhibit biliary duct cell-fate and trigger the differentiation of the cells towards a more hepatocytic phenotype (see WO 2012/168930). In particular, inclusion of a TGF-beta inhibitor (such as A83-01) in a differentiation medium was found to enhance the expression of mature hepatocyte markers and increase the number of hepatocyte-like cells.

Accordingly, the differentiation medium of the invention preferably comprises a TGF-beta inhibitor.

The TGF-beta superfamily ligands comprise bone morphogenic proteins (BMPs), growth and differentiation factors (GDFs), anti-müllerian hormone (AMH), activin, nodal and TGF-betas. In general, Smad2 and Smad3 are phosphorylated by the ALK4, 5 and 7 receptors in the TGF-beta/activin pathway. By contrast, Smad1, Smad5 and Smad8 are phosphorylated as part of the bone morphogenetic protein (BMP) pathway. Although there is some cross-over between pathways, in the context of this invention, a “TGF-beta inhibitor” or an “inhibitor of TGF-beta signalling” is preferably an inhibitor of the TGF-beta pathway which acts via Smad2 and Smad3 and/or via ALK4, ALK5 or ALK7. Therefore, in some embodiments the TGF-beta inhibitor is not a BMP inhibitor, i.e. the TGF-beta inhibitor is not Noggin. In some embodiments, a BMP inhibitor is added to the culture medium in addition to the TGF-beta inhibitor. Thus the TGF-beta inhibitor may be any agent that reduces the activity of the TGF-beta signalling pathway, preferably the signalling pathway that acts via Smad2 and/or Smad3, more preferably the signalling pathway that acts via ALK4, ALK5 or ALK7.

There are many ways of disrupting the TGF-beta signaling pathway that are known in the art and that can be used in conjunction with this invention. For example, the TGF-beta signaling may be disrupted by: inhibition of TGF-beta expression by a small-interfering RNA strategy; inhibition of furin (a TGF-beta activating protease); inhibition of the pathway by physiological inhibitors; neutralisation of TGF-beta with a monoclonal antibody; inhibition with small-molecule inhibitors of TGF-beta receptor kinase 1 (also known as activin receptor-like kinase, ALK5), ALK4, ALK6, ALK7 or other TGF-beta-related receptor kinases; inhibition of Smad 2 and Smad 3 signaling e.g. by overexpression of their physiological inhibitor, Smad 7, or by using thioredoxin as an Smad anchor disabling Smad from activation (Fuchs, O. Inhibition of TGF-Signaling for the Treatment of Tumor Metastasis and Fibrotic Diseases. Current Signal Transduction Therapy, Volume 6, Number 1, January 2011, pp. 29-43 (15)).

Various methods for determining if a substance is a TGF-beta inhibitor are known and might be used in conjunction with the invention. For example, a cellular assay may be used in which cells are stably transfected with a reporter construct comprising the human PAI-1 promoter or Smad binding sites, driving a luciferase reporter gene. Inhibition of luciferase activity relative to control groups can be used as a measure of compound activity (De Gouville et al., Br J Pharmacol. 2005 May; 145 (2): 166-177). New TGF-beta inhibitors can therefore be easily identified by the skilled person in the art.

A TGF-beta inhibitor according to the present invention may be a protein, peptide, small-molecules, small-interfering RNA, antisense oligonucleotide, aptamer or antibody. The inhibitor may be naturally occurring or synthetic. In one embodiment, the TGF-beta inhibitor is an inhibitor of ALK4, ALK5 and/or ALK7. For example, the TGF-beta inhibitor may bind to and directly inhibit ALK4, ALK5 and/or ALK7. Examples of preferred small-molecule TGF-beta inhibitors that can be used in the context of this invention include but are not limited to the small molecule inhibitors listed in table 2 below.

TABLE 2

Small-molecule TGF-beta inhibitors targeting receptor kinases

| Inhibitor | Targets | IC50 (nM) | Mol Wt | Name | Formula |
|---|---|---|---|---|---|
| A83-01 | ALK5 (TGF-βR1)<br>ALK4<br>ALK7 | 12<br>45<br>7.5 | 421.52 | 3-(6-Methyl-2-pyridinyl)-N-phenyl-4-(4-quinolinyl)-1H-pyrazole-1-carbothioamide | C25H19N5S |
| SB-431542 | ALK5<br>ALK4<br>ALK7 | 94 | 384.39 | 4-[4-(1,3-benzodioxol-5-yl)-5-(2-pyridinyl)-1H-imidazol-2-yl]benzamide | C22H16N4O3 |
| SB-505124 | ALK5<br>ALK4 | 47<br>129 | 335.4 | 2-(5-benzo[1,3]dioxol-5-yl-2-tert-butyl-3Himidazol-4-yl)-6-methylpyridine hydrochloride hydrate | C20H21N3O2 |
| SB-525334 | ALK5 | 14.3 | 343.42 | 6-[2-(1,1-Dimethylethyl)-5-(6-methyl-2-pyridinyl)-1H-imidazol-4-yl]quinoxaline | C21H21N5 |
| SD-208 | ALK5 | 49 | 352.75 | 2-(5-Chloro-2-fluorophenyl)-4-[(4-pyridyl)amino]pteridine | C17H10C1FN6 |
| LY-36494 | TGR-βRI<br>TGF-βRII<br>MLK-7K | 59<br>400<br>1400 | 272.31 | 4-[3-(2-Pyridinyl)-1H-pyrazol-4-yl]-quinoline | C17H12N4 |
| SJN-2511 | ALK5 | 23 | 287.32 | 2-(3-(6-Methylpyridine-2-yl)-1H-pyrazol-4-yl)-1,5-naphthyridine | C17H13N5 |

In some embodiments, the TGF-beta inhibitor is a small molecule inhibitor optionally selected from the group consisting of: A83-01, SB-431542, SB-505124, SB-525334, LY 364947, SD-208 and SJN 2511.

In some embodiments, no more than one TGF beta inhibitor is present in the differentiation medium. In other embodiments, more than one TGF beta inhibitor is present in the differentiation medium, e.g. 2, 3, 4 or more. In some embodiments, a differentiation medium of the invention comprises one or more of any of the inhibitors listed in table 2. A differentiation medium may comprise any combination of one inhibitor with another inhibitor listed. For example, a medium may comprise SB-525334 or SD-208 or A83-01;

or SD-208 and A83-01. The skilled person will appreciate that a number of other small-molecule inhibitors exist that are primarily designed to target other kinases, but at high concentrations may also inhibit TGF-beta receptor kinases. For example, SB-203580 is a p38 MAP kinase inhibitor that, at high concentrations (for example, approximate 10 μM or more) is thought to inhibit ALK5. Any such inhibitor that inhibits the TGF-beta signalling pathway can also be used in the context of this invention.

In some embodiments, the TGF-beta inhibitor (e.g. A83-01) is present in the differentiation medium at at least 1 nM, for example, at least 5 nM, at least 50 nM, at least 100 nM, at least 300 nM, at least 450 nM or at least 475 nM. For example, the TGF-beta inhibitor (e.g. A83-01) is present in the differentiation medium at 1 nM-200μ, 10 nM-200 μM, 100 μM-200 μM, 1 μM-200 μM, 10 μM-100 μM, 50 nM-100 μM, 50 nM-10 μM, 100 nM-1 μM, 200 nM-800 nM, 350-650 nM or at about 500 nM. Accordingly, in some embodiments, the differentiation medium comprises A83-01 at a concentration of about 500 nM.

BMP Pathway Activator

In some embodiments, the differentiation medium comprises a BMP pathway activator. In some embodiments, the BMP pathway activator is selected from BMP7, BMP4 and BMP2. BMP7 is preferred. BMP7 induces the phosphorylation of SMAD1 and SMAD5. Thus in some embodiments, the BMP pathway activator is any compound that is capable of inducing the phosphorylation of SMAD1 and SMAD5. In addition, where BMP7 is mentioned, any compound that induces the phosphorylation of SMAD1 or SMAD5 can be used instead of BMP7.

In some embodiments, the BMP pathway activator, such as BMP7 is present in the differentiation medium at at least 0.01 ng·ml, at least 0.1 ng/ml, at least 1 ng/ml, at least 10 ng/ml, at least 20 ng/ml, at least 25 ng/ml. In some embodiments, the BMP pathway activator, such as BMP7 is present in the differentiation medium from about 0.01 ng/ml to about 500 ng/ml, from about 1 ng/ml to about 500 ng/ml, from about 10 ng/ml to about 500 ng/ml, from about 20 ng/ml to about 500 ng/ml. In some embodiments, the BMP pathway activator, such as BMP7, is present in the differentiation medium from about 0.01 ng/ml to about 200 ng/ml, from about 0.1 ng/ml to about 100 ng/ml, from about 1 ng/ml to about 100 ng/ml, from about 10 ng/ml to about 100 ng/ml, from about 10 ng/ml to about 50 ng/ml, from about 15 ng/ml to about 30 ng/ml. In some embodiments, the BMP pathway activator, such as BMP7 is present in the differentiation medium at about 25 ng/ml.

In some embodiments, the differentiation medium does not comprise a BMP pathway activator.

Additional Components

In some embodiments, the differentiation medium of the invention comprises gastrin. In some embodiments, the differentiation medium of the invention comprises gastrin at a concentration of 0.01-500 nM, 0.1-100 nM, 1-100 nM, 1-20 nM or 5-15 nM. For example, in some embodiments, the differentiation medium of the invention comprises gastrin at a concentration of about 10 nM.

The differentiation medium of the invention is preferably supplemented with one or more (e.g. 1, 2, 3 or all) of the compounds selected from the group consisting of B27, N-acetylcysteine and N2. Thus in some embodiments the differentiation medium further comprises one or more components selected from the group consisting of: B27, N2 and N-Acetylcysteine. For example, in some embodiments, the differentiation medium further comprises B27, N-Acetylcysteine and N2.

B27 (Invitrogen), N-Acetylcysteine (Sigma) and N2 (Invitrogen), and Nicotinamide (Sigma) are believed to control proliferation of the cells and assist with DNA stability.

In some embodiments, N-Acetylcysteine is present in the differentiation medium at a concentration of 0.1-200 mM, 0.1-100 mM, 0.1-50 mM, 0.1-10 mM, 0.1-5 mM, 0.5-200 mM, 0.5-100 mM, 0.5-50 mM, 0.5-10 mM, 0.5-5 mM, 1-100 mM, 1-50 mM, 1-10 mM, 1-5 mM. In some embodiments, N-Acetylcysteine is present in the differentiation medium at a concentration of about 1.25 mM.

In some embodiments, the B27 supplement is 'B27 Supplement minus Vitamin A' (also referred to herein as "B27 without Vitamin A" or "B27 wo VitA"; available from Invitrogen, Carlsbad, CA; www.invitrogen.com; currently catalog no. 12587010; and from PAA Laboratories GmbH, Pasching, Austria; www.paa.com; catalog no. F01-002; Brewer et al., J Neurosci Res., 35 (5): 567-76, 1993). In some embodiments, the B27 supplement can be replaced with a generic formulation that comprises one or more of the components selected from the list: biotin, cholesterol, linoleic acid, linolenic acid, progesterone, putrescine, retinyl acetate, sodium selenite, tri-iodothyronine (T3), DL-alpha tocopherol (vitamin E), albumin, insulin and transferrin.

The B27 Supplement supplied by PAA Laboratories GmbH comes as a liquid 50× concentrate, containing amongst other ingredients biotin, cholesterol, linoleic acid, linolenic acid, progesterone, putrescine, retinol, retinyl acetate, sodium selenite, tri-iodothyronine (T3), DL-alpha tocopherol (vitamin E), albumin, insulin and transferrin. Of these ingredients at least linolenic acid, retinol, retinyl acetate and tri-iodothyronine (T3) are nuclear hormone receptor agonists. B27 Supplement may be added to a differentiation medium as a concentrate or diluted before addition to a differentiation medium. It may be used at a 1× final concentration or at other final concentrations (e.g. 0.1× to 4× concentration, 0.1× to 2× concentration, 0.5× to 2× concentration, 1× to 4× concentration, or 1× to 2× concentration). Use of B27 Supplement is a convenient way to incorporate biotin, cholesterol, linoleic acid, linolenic acid, progesterone, putrescine, retinol, retinyl acetate, sodium selenite, tri-iodothyronine (T3), DL-alpha tocopherol (vitamin E), albumin, insulin and transferrin into a differentiation medium of the invention. It is also envisaged that some or all of these components may be added separately to the differentiation medium instead of using the B27 Supplement. Thus, the differentiation medium may comprise some or all of these components.

In some embodiments, retinoic acid is absent from the B27 Supplement used in the differentiation medium, and/or is absent from the differentiation medium.

'N2 Supplement' (also referred to herein as "N2") is available from Invitrogen, Carlsbad, CA; www.invitrogen.com; catalog no. 17502-048; and from PAA Laboratories GmbH, Pasching, Austria; www.paa.com; catalog no. F005-004; Bottenstein & Sato, PNAS, 76 (1): 514-517, 1979. The N2 Supplement supplied by PAA Laboratories GmbH comes as a 100× liquid concentrate, containing 500 μg/ml human transferrin, 500 μg/ml bovine insulin, 0.63 μg/ml progesterone, 1611 μg/ml putrescine, and 0.52 μg/ml sodium selenite. N2 Supplement may be added to a differentiation medium as a concentrate or diluted before addition to a differentiation medium. It may be used at a 1× final concentration or at other final concentrations (e.g. 0.1× to 4× concentration, 0.1× to 2× concentration, 0.5× to 2× concentration, 1× to 4× concentration, or 1× to 2× concentration). Use of N2 Supplement is a convenient way to incorporate transferrin, insulin, progesterone, putrescine and sodium selenite into a differentiation medium of the invention. It is of course also envisaged that some or all of these components may be added separately to the differentiation medium instead of using the N2 Supplement. Thus, the differentiation medium may comprise some or all of these components.

In some embodiments in which the medium comprises B27, it does not also comprise N2. The embodiments of the present invention can therefore be adapted to exclude N2 when B27 is present, if desired.

In some embodiments N2 is not present in the differentiation medium.

In some embodiments in which the medium comprises N2, it does not also comprise B27. The embodiments of the present invention can therefore be adapted to exclude B27 when N2 is present, if desired.

In some embodiments B27 is not present in the differentiation medium.

In some embodiments the differentiation medium is supplemented with B27 and/or N2.

In some embodiments, the basal medium is supplemented with 150 ng/ml to 250 ng/ml N-Acetylcysteine; preferably, the basal medium is supplemented with about 200 ng/ml N-Acetylcysteine.

Any suitable pH may be used. For example, the pH of the medium may be in the range from about 7.0 to 7.8, in the range from about 7.2 to 7.6, or about 7.4. The pH may be maintained using a buffer. A suitable buffer can readily be selected by the skilled person. Buffers that may be used include carbonate buffers (e.g. $NaHCO_3$), and phosphates (e.g. $NaH_2PO_4$). These buffers are generally used at about 50 to about 500 mg/l. Other buffers such as N-[2-hydroxy-ethyl]-piperazine-N'-[2-ethanesul-phonic acid] (HEPES) and 3-[N-morpholino]-propanesulfonic acid (MOPS) may also be used, normally at around 1000 to around 10,000 mg/l. In some embodiments, the buffer is selected from one or more of the list: phosphate buffer (e.g. $KH_2PO_4$, $K_2HPO_4$, $Na_2HPO_4$, NaCl, $NaH_2PO_4$) acetate buffer (e.g. HOAc or NaOAc), citrate buffer (e.g. Citric acid or Na-citrate), or a TRIS buffer (e.g. TRIS, TRIS-HCl) or an organic buffer. In some embodiments, the organic buffer is a zwitterionic buffer, such as a Good's buffer, e.g. selected from HEPES, MOPS, MES, ADA, PIPES, ACES, MOPSO, Cholamine Chloride, BES, TES, DIPSO, acetamindoglycine, TAPSO, POPSO, HEPPSO, HEPPS, Tricine, Glycinamide, Bicine, TAPS, AMPSO, CABS, CHES, CAPS and CAPSO. A preferred buffer is HEPES, e.g. at a concentration of 0.1-100 mM, 0.1-50 mM, 0.5-50 mM, 1-50 mM, 1-20 mM, or 5-15 mM. In some embodiments, HEPES is added to the culture medium at about 10 mM. A differentiation medium may also comprise a pH indicator, such as phenol red, to enable the pH status of the medium to be easily monitored (e.g. at about 5 to about 50 mg/litre).

A differentiation medium for use in the invention may comprise one or more amino acids. The skilled person understands the appropriate types and amounts of amino acids for use in differentiation media. Amino acids which may be present include L-alanine, L-arginine, L-asparagine, L-aspartic acid, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, L-valine and combinations thereof. Some differentiation media will contain all of these amino acids. Generally, each amino acid when present is present at about 0.001 to about 1 g/L of medium (usually at about 0.01 to about 0.15 g/L), except for L-glutamine which is present at about 0.05 to about 1 g/L (usually about 0.1 to about 0.75 g/L). The amino acids may be of synthetic origin.

A differentiation medium for use in the invention may comprise one or more vitamins. The skilled person understands the appropriate types and amounts of vitamins for use in differentiation media. Vitamins which may be present include thiamine (vitamin B1), riboflavin (vitamin B2), niacin (vitamin B3), D-calcium pantothenate (vitamin B5), pyridoxal/pyridoxamine/pyridoxine (vitamin B6), folic acid (vitamin B9), cyanocobalamin (vitamin B12), ascorbic acid (vitamin C), calciferol (vitamin D2), DL-alpha tocopherol (vitamin E), biotin (vitamin H) and menadione (vitamin K).

A differentiation medium for use in the invention may comprise one or more inorganic salts. The skilled person understands the appropriate types and amounts of inorganic salts for use in differentiation media. Inorganic salts are typically included in differentiation media to aid maintenance of the osmotic balance of the cells and to help regulate membrane potential. Inorganic salts which may be present include salts of calcium, copper, iron, magnesium, potassium, sodium, zinc. The salts are normally used in the form of chlorides, phosphates, sulphates, nitrates and bicarbonates. Specific salts that may be used include $CaCl_2$), $CuSO_4$-$5H_2O$, $Fe(NO_3)$-$9H_2O$, $FeSO_4$-$7H_2O$, MgCl, $MgSO_4$, KCl, $NaHCO_3$, NaCl, $Na_2HPO_4$, $Na_2HPO_4$—$H_2O$ and $ZnSO_4$-$7H_2O$.

The osmolarity of the medium may be in the range from about 200 to about 400 mOsm/kg, in the range from about 290 to about 350 mOsm/kg, or in the range from about 280 to about 310 mOsm/kg. The osmolarity of the medium may be less than about 300 mOsm/kg (e.g. about 280 mOsm/kg).

A differentiation medium for use in the invention may comprise a carbon energy source, in the form of one or more sugars. The skilled person understands the appropriate types and amounts of sugars to use in differentiation media. Sugars which may be present include glucose, galactose, maltose and fructose. The sugar is preferably glucose, particularly D-glucose (dextrose). A carbon energy source will normally be present at between about 1 and about 10 g/L.

A differentiation medium of the invention may contain serum. Serum obtained from any appropriate source may be used, including fetal bovine serum (FBS), goat serum or human serum. Preferably, human serum is used. Serum may be used at between about 1% and about 30% by volume of the medium, according to conventional techniques.

In other embodiments, a differentiation medium of the invention may contain a serum replacement. Various different serum replacement formulations are commercially available and are known to the skilled person. Where a serum replacement is used, it may be used at between about 1% and about 30% by volume of the medium, according to conventional techniques.

In other embodiments, a differentiation medium of the invention may be serum-free and/or serum replacement-free. A serum-free medium is one that contains no animal serum of any type. Serum-free media may be preferred to avoid possible xeno-contamination of the stem cells. A serum replacement-free medium is one that has not been supplemented with any commercial serum replacement formulation.

In a preferred embodiment, the differentiation medium is supplemented with a purified, natural, semi-synthetic and/or synthetic growth factor and does not comprise an undefined component, such as fetal bovine serum or fetal calf serum. For example, supplements such as B27 (Invitrogen), N-Acetylcysteine (Sigma) and N2 (Invitrogen) stimulate proliferation of some cells. In some embodiments, the differentiation medium is supplemented with one or more of these supplements, for example one, any two or all three of these supplements.

A differentiation medium for use in the invention may comprise one or more trace elements, such as ions of barium, bromium, cobalt, iodine, manganese, chromium, copper, nickel, selenium, vanadium, titanium, germanium, molybdenum, silicon, iron, fluorine, silver, rubidium, tin, zirconium, cadmium, zinc and/or aluminium.

The medium may comprise a reducing agent, such as beta-mercaptoethanol at a concentration of about 0.1 mM.

A differentiation medium of the invention may comprise one or more additional agents, such as nutrients or growth factors previously reported to improve stem cell culture, such as cholesterol/transferrin/albumin/insulin/progesterone, putrescine, selenite/other factors.

Basal Medium

A differentiation medium that is used in a method of the invention comprises a basal medium. The basal medium is any suitable basal medium for animal or human cells, subject to the limitations provided herein.

Basal media for animal or human cell culture typically contain a large number of ingredients, which are necessary to support maintenance of the cultured cells. Suitable combinations of ingredients can readily be formulated by the skilled person, taking into account the following disclosure. A basal medium for use in the invention will generally comprises a nutrient solution comprising standard cell culture ingredients, such as amino acids, vitamins, lipid supplements, inorganic salts, a carbon energy source, and a buffer, as described in more detail in the literature and above. In some embodiments, the culture medium is further supplemented with one or more standard cell culture ingredient, for example selected from amino acids, vitamins, lipid supplements, inorganic salts, a carbon energy source, and a buffer.

The skilled person will understand from common general knowledge the types of culture media that might be used as the basal medium in the differentiation medium of the invention. Potentially suitable cell culture media are available commercially, and include, but are not limited to, Dulbecco's Modified Eagle Media (DMEM), Minimal Essential Medium (MEM), Knockout-DMEM (KO-DMEM), Glasgow Minimal Essential Medium (G-MEM), Basal Medium Eagle (BME), DMEM/Ham's F12, Advanced DMEM/Ham's F12, Iscove's Modified Dulbecco's Media and Minimal Essential Media (MEM), Ham's F-10, Ham's F-12, Medium 199, and RPMI 1640 Media.

For example, the basal medium may be selected from DMEM/F12 and RPMI 1640 supplemented with glutamine, insulin, penicillin/streptomycin and transferrin. In a further preferred embodiment, Advanced DMEM/F12 or Advanced RPMI is used, which is optimized for serum free culture and already includes insulin. In this case, said Advanced DMEM/F12 or Advanced RPMI medium is preferably supplemented with glutamine and penicillin/streptomycin. AdDMEM/12 (Invitrogen) supplemented with N2 and B27 is also preferred. Preferably, the basal medium is Advanced DMEM/F12. More preferably, the basal medium comprises Advanced DMEM/F12, glutamine and B27.

In some embodiments, the basal medium comprises Advanced DMEM/F12, HEPES, penicillin/streptomycin, Glutamine, N-Acetylcysteine, B27, N2 and Gastrin.

In some embodiments, the basal culture medium comprises or consists of Advanced DMEM/F12 supplemented with penicillin/streptomycin, 10 mM HEPES, Glutamax, 1×N2, 1×B27 (all from Invitrogen) and about 1.25 mM N-acetylcysteine (Sigma).

It is furthermore preferred that said basal culture medium is supplemented with a purified, natural, semi-synthetic and/or synthetic growth factor and does not comprise an undefined component such as fetal bovine serum or fetal calf serum. Various different serum replacement formulations are commercially available and are known to the skilled person. Where a serum replacement is used, it may be used at between about 1% and about 30% by volume of the medium, according to conventional techniques.

The differentiation medium used in the invention may comprise serum, or may be serum-free and/or serum-replacement free, as described elsewhere herein. Culture media and cell preparations are preferably GMP processes in line with standards required by the FDA for biologics products and to ensure product consistency.

A differentiation medium of the invention will normally be formulated in deionized, distilled water. A differentiation medium of the invention will typically be sterilized prior to use to prevent contamination, e.g. by ultraviolet light, heating, irradiation or filtration. The differentiation medium may be frozen (e.g. at −20° C. or −80° C.) for storage or transport. The medium may contain one or more antibiotics to prevent contamination. The medium may have an endotoxin content of less than 0.1 endotoxin units per ml, or may have an endotoxin content less than 0.05 endotoxin units per ml. Methods for determining the endotoxin content of culture media are known in the art.

A preferred basal culture medium is a defined synthetic medium that is buffered at a pH of 7.4 (preferably with a pH 7.2-7.6 or at least 7.2 and not higher than 7.6) with a carbonate-based buffer, while the cells are cultured in an atmosphere comprising between 5% and 10% $CO_2$, or at least 5% and not more than 10% $CO_2$, preferably 5% $CO_2$.

In some embodiments, a differentiation medium is provided with a basal medium ready for use in a differentiation method. In other embodiments, the differentiation medium is provided without a basal medium, e.g. as a culture medium supplement, and the basal medium (or other components) can be added prior to use in a differentiation method. Accordingly, there is provided any differentiation medium described herein wherein the basal medium is absent or wherein the basal medium is only an optional component.

Compositions and Vessels

The invention also provides a composition or cell culture vessel comprising cells and/or organoids according to any one of the aspects of the invention described above, and a differentiation medium according to any one of the aspects of the invention described above. For example, such a composition or cell culture vessel may comprise any number of cells or organoids cultured according to a method of the invention, in a differentiation medium as described above.

According to a still further aspect of the invention, there is provided a hermetically-sealed vessel containing a differentiation medium of the invention. Hermetically-sealed vessels may be preferred for transport or storage of the differentiation media, to prevent contamination. The vessel may be any suitable vessel, such as a flask, a plate, a bottle, a jar, a vial or a bag.

Exemplary Culture Media of the Invention

In some embodiments, the differentiation medium of the invention comprises:

(i) one or more receptor tyrosine kinase ligands, e.g. selected from a ligand for RTK class I (e.g. EGF), a ligand for RTK class IV (e.g. FGF), and a ligand for RTK class VI (e.g. HGF), each preferably at a concentration of 1 to 200 ng/ml, (ii) one or more TGF-beta inhibitors, such as one or more inhibitor of ALK5, ALK4 or ALK7, e.g. selected from A83-01, SB-431542, SB-505124, SB-525334, LY 364947, SD-208 and SJN 2511, preferably at a concentration of 100 nM to 200 μM, (iii) a Notch inhibitor, for example, a gamma-secretase inhibitor, e.g. selected from DAPT, dibenzazepine (DBZ), benzodiazepine (BZ) and LY-411575, preferably at a concentration of 0.001 to 100 μM, and (iv) one or more Wnt inhibitor, such as (a) an inhibitor of Wnt secretion, e.g. a Porc inhibitor selected from IWP-2, LGK974 and IWP-1, preferably at a concentration of 0.01-150 μM, and/or (b) an inhibitor of β-catenin target gene expression, e.g. selected from iCRT3, CGP049090, PKF118310, PKF115-584, ZTM000990, PNU-74654, BC21, iCRT5, iCRT14 and FH535, preferably at a concentration of 0.05-150 μM.

In some embodiments, the differentiation medium of the invention comprises:

(i) one or more receptor tyrosine kinase ligands, e.g. selected from a ligand for RTK class I (e.g. EGF), a ligand for RTK class IV (e.g. FGF), and a ligand for RTK class VI (e.g. HGF), each preferably at a concentration of 1 to 200 ng/ml, (ii) one or more TGF-beta inhibitors, such as one or more inhibitor of ALK5, ALK4 or ALK7, e.g. selected from A83-01, SB-431542, SB-505124, SB-525334, LY 364947, SD-208 and SJN 2511, preferably at a concentration of 100 nM to 200 μM, (iii) a Notch inhibitor, for example, a gamma-secretase inhibitor, e.g. selected from DAPT, dibenzazepine (DBZ), benzodiazepine (BZ) and LY-411575, preferably at a concentration of 0.001 to 100 μM, and (iv) a GSK-3 inhibitor, e.g. selected from CHIR 99021, 6-BIO, Dibromocantharelline, Hymenialdesine, Indirubins, Meridianins, CT98014, CT98023, CT99021, TWS119, SB-216763, SB-41528, AR-A014418, AZD-1080, Alsterpaullone, Cazpaullone, Kenpaullone, Aloisines, Manzamine A, Palinurine, Tricantine, TDZD-8, NP00111, NP031115, Tideglusib, HMK-32 and L803-mts, preferably at a concentration of 0.01-150 μM.

In some embodiments, the differentiation medium of the invention comprises:

(i) one or more receptor tyrosine kinase ligands, e.g. selected from a ligand for RTK class I (e.g. EGF), a ligand for RTK class IV (e.g. FGF), and a ligand for RTK class VI (e.g. HGF), each preferably at a concentration of 1 to 200 ng/ml, (ii) one or more TGF-beta inhibitors, such as one or more inhibitor of ALK5, ALK4 or ALK7, e.g. selected from A83-01, SB-431542, SB-505124, SB-525334, LY 364947, SD-208 and SJN 2511, preferably at a concentration of 100 nM to 200 μM, (iii) a Notch inhibitor, for example, a gamma-secretase inhibitor, e.g. selected from DAPT, dibenzazepine (DBZ), benzodiazepine (BZ) and LY-411575, preferably at a concentration of 0.001 to 100 μM, (iv) one or more Wnt inhibitor, such as (a) an inhibitor of Wnt secretion, e.g. a Porc inhibitor selected from IWP-2, LGK974 and IWP-1, preferably at a concentration of 0.01-150 μM, and/or (b) an inhibitor of β-catenin target gene expression, e.g. selected from iCRT3, CGP049090, PKF118310, PKF115-584, ZTM000990, PNU-74654, BC21, iCRT5, iCRT14 and FH535, preferably at a concentration of 0.05-150 μM, and (v) a GSK-3 inhibitor, e.g. selected from CHIR 99021, 6-BIO, Dibromocantharelline, Hymenialdesine, Indirubins, Meridianins, CT98014, CT98023, CT99021, TWS119, SB-216763, SB-41528, AR-A014418, AZD-1080, Alsterpaullone, Cazpaullone, Kenpaullone, Aloisines, Manzamine A, Palinurine, Tricantine, TDZD-8, NP00111, NP031115, Tideglusib, HMK-32 and L803-mts, preferably at a concentration of 0.01-150 μM.

In some embodiments, the differentiation medium of the invention comprises:

(i) one or more receptor tyrosine kinase ligands, e.g. selected from a ligand for RTK class I (e.g. EGF), a ligand for RTK class IV (e.g. FGF), and a ligand for RTK class VI (e.g. HGF), each preferably at a concentration of 1 to 200 ng/ml, (ii) one or more TGF-beta inhibitors, such as one or more inhibitor of ALK5, ALK4 or ALK7, e.g. selected from A83-01, SB-431542, SB-505124, SB-525334, LY 364947, SD-208 and SJN 2511, preferably at a concentration of 100 nM to 200 μM, (iii) a Notch inhibitor, for example, a gamma-secretase inhibitor, e.g. selected from DAPT, dibenzazepine (DBZ), benzodiazepine (BZ) and LY-411575, preferably at a concentration of 0.001 to 100 μM, (iv) a GSK-3 inhibitor, e.g. selected from CHIR 99021, 6-BIO, Dibromocantharelline, Hymenialdesine, Indirubins, Meridianins, CT98014, CT98023, CT99021, TWS119, SB-216763, SB-41528, AR-A014418, AZD-1080, Alsterpaullone, Cazpaullone, Kenpaullone, Aloisines, Manzamine A, Palinurine, Tricantine, TDZD-8, NP00111, NP031115, Tideglusib, HMK-32 and L803-mts, preferably at a concentration of 0.01-150 μM, and (v) one or more Wnt inhibitor that acts downstream of the β-catenin destruction complex, such as an inhibitor of β-catenin target gene expression, e.g. selected from iCRT3, CGP049090, PKF118310, PKF115-584, ZTM000990, PNU-74654, BC21, iCRT5, iCRT14 and FH535, preferably at a concentration of 0.05-150 μM.

In some embodiments, the differentiation medium of the invention comprises:

(i) one or more receptor tyrosine kinase ligands, e.g. selected from a ligand for RTK class I (e.g. EGF), a ligand for RTK class IV (e.g. FGF), and a ligand for RTK class VI (e.g. HGF), each preferably at a concentration of 1 to 200 ng/ml, (ii) one or more TGF-beta inhibitors, such as one or more inhibitor of ALK5, ALK4 or ALK7, e.g. selected from A83-01, SB-431542, SB-505124, SB-525334, LY 364947, SD-208 and SJN 2511, preferably at a concentration of 100 nM to 200 μM, (iii) a Notch inhibitor, for example, a gamma-secretase inhibitor, e.g. selected from DAPT, dibenzazepine (DBZ), benzodiazepine (BZ) and LY-411575, preferably at a concentration of 0.001 to 100 μM, and (iv) an AP-1 stimulant, such as a muscarinic acetylcholine receptor agonist, e.g. selected from carbachol, acetylcholine, bethanecol, oxotremorine, L-689,660 (1-azabicyclo[2.2.2]octane, 3-(6-chloropyrazinyl) maleate), pilocarpine, muscarine, McN-A 343 (4-[[[(3-Chlorophenyl)amino]carbonyl]oxy]-N,N,N-trimethyl-2-butyn-1-aminium chloride), 77-LH-218-1 (1-[3-(4-Butyl-1-piperidinyl) propyl]-3,4-dihydro-2(1H)- quinolinone) and methacholine, preferably at a concentration of 0.001-300 μM.

In some embodiments, the differentiation medium of the invention comprises:

(i) one or more receptor tyrosine kinase ligands, e.g. selected from a ligand for RTK class I (e.g. EGF), a ligand for RTK class IV (e.g. FGF), and a ligand for RTK class VI (e.g. HGF), each preferably at a concentration of 1 to 200 ng/ml, (ii) one or more TGF-beta inhibitors, such as one or more inhibitor of ALK5, ALK4 or ALK7, e.g. selected from A83-01, SB-431542, SB-505124, SB-525334, LY 364947, SD-208 and SJN 2511, preferably at a concentration of 100 nM to 200 μM, (iii) a Notch inhibitor, for example, a gamma-secretase inhibitor, e.g. selected from DAPT, dibenzazepine (DBZ), benzodiazepine (BZ) and LY-411575, preferably at a concentration of 0.001 to 100 μM, (iv) one or more Wnt inhibitor, (a) an inhibitor of Wnt secretion, e.g. a Porc inhibitor selected from IWP-2, LGK974 and IWP-1, preferably at a concentration of 0.01-150 μM, and/or (b) an inhibitor of β-catenin target gene expression, e.g. selected from iCRT3, CGP049090, PKF118310, PKF115-584, ZTM000990, PNU-74654, BC21, iCRT5, iCRT14 and FH535, preferably at a concentration of 0.05-150 μM, and (v) an AP-1 stimulant, such as a muscarinic acetylcholine receptor agonist, e.g. selected from carbachol, acetylcholine, bethanecol, oxotremorine, L-689,660 (1-azabicyclo[2.2.2]octane, 3-(6-chloropyrazinyl) maleate), pilocarpine, muscarine, McN-A 343 (4-[[[(3-Chlorophenyl)amino]carbonyl]oxy]-N,N,N-trimethyl-2-butyn-1-aminium chloride), 77-LH-218-1 (1-[3-(4-Butyl-1-piperidinyl) propyl]-3,4-dihydro-2(1H)-quinolinone) and methacholine, preferably at a concentration of 0.001-300 μM.

In some embodiments, the differentiation medium of the invention comprises:

(i) one or more receptor tyrosine kinase ligands, e.g. selected from a ligand for RTK class I (e.g. EGF), a ligand for RTK class IV (e.g. FGF), and a ligand for RTK class VI (e.g. HGF), each preferably at a concentration of 1 to 200 ng/ml, (ii) one or more TGF-beta inhibitors, such as one or more inhibitor of ALK5, ALK4 or ALK7, e.g. selected from A83-01, SB-431542, SB-505124, SB-525334, LY 364947, SD-208 and SJN 2511, preferably at a concentration of 100 nM to 200 μM, (iii) a Notch inhibitor, for example, a gamma-secretase inhibitor, e.g. selected from DAPT, dibenzazepine (DBZ), benzodiazepine (BZ) and LY-411575, preferably at a concentration of 0.001 to 100 μM, (iv) a GSK-3 inhibitor, e.g. selected from CHIR 99021, 6-BIO, Dibromocantharelline, Hymenialdesine, Indirubins, Meridianins, CT98014, CT98023, CT99021, TWS119, SB-216763, SB-41528, AR-A014418, AZD-1080, Alsterpaullone, Cazpaullone, Kenpaullone, Aloisines, Manzamine A, Palinurine, Tricantine, TDZD-8, NP00111, NP031115, Tideglusib, HMK-32 and L803-mts, preferably at a concentration of 0.01-150 μM, and (v) an AP-1 stimulant, such as a muscarinic acetylcholine receptor agonist, e.g. selected from carbachol, acetylcholine, bethanecol, oxotremorine, L-689,660 (1-azabicyclo[2.2.2]octane, 3-(6-chloropyrazinyl) maleate), pilocarpine, muscarine, McN-A 343 (4-[[[(3-Chlorophenyl)amino]carbonyl]oxy]-N,N,N-trimethyl-2-butyn-1-aminium chloride), 77-LH-218-1 (1-[3-(4-Butyl-1-piperidinyl) propyl]-3,4-dihydro-2(1H)-quinolinone) and methacholine, preferably at a concentration of 0.001-300 μM.

In some embodiments, the differentiation medium of the invention comprises:

(i) one or more receptor tyrosine kinase ligands, e.g. selected from a ligand for RTK class I (e.g. EGF), a ligand for RTK class IV (e.g. FGF), and a ligand for RTK class VI (e.g. HGF), each preferably at a concentration of 1 to 200 ng/ml, (ii) one or more TGF-beta inhibitors, such as one or more inhibitor of ALK5, ALK4 or ALK7, e.g. selected from A83-01, SB-431542, SB-505124, SB-525334, LY 364947, SD-208 and SJN 2511, preferably at a concentration of 100 nM to 200 μM, (iii) a Notch inhibitor, for example, a gamma-secretase inhibitor, e.g. selected from DAPT, dibenzazepine (DBZ), benzodiazepine (BZ) and LY-411575, preferably at a concentration of 0.001 to 100 μM, (iv) one or more Wnt inhibitor, (a) an inhibitor of Wnt secretion, e.g. a Porc inhibitor selected from IWP-2, LGK974 and IWP-1, preferably at a concentration of 0.01-150 μM, and/or (b) an inhibitor of β-catenin target gene expression, e.g. selected from iCRT3, CGP049090, PKF118310, PKF115-584, ZTM000990, PNU-74654, BC21, iCRT5, iCRT14 and FH535, preferably at a concentration of 0.05-150 μM, (v) a GSK-3 inhibitor, e.g. selected from CHIR 99021, 6-BIO, Dibromocantharelline, Hymenialdesine, Indirubins, Meridianins, CT98014, CT98023, CT99021, TWS119, SB-216763, SB-41528, AR-A014418, AZD-1080, Alsterpaullone, Cazpaullone, Kenpaullone, Aloisines, Manzamine A, Palinurine, Tricantine, TDZD-8, NP00111, NP031115, Tideglusib, HMK-32 and L803-mts, preferably at a concentration of 0.01-150 μM, and (vi) an AP-1 stimulant, such as a muscarinic acetylcholine receptor agonist, e.g. selected from carbachol, acetylcholine, bethanecol, oxotremorine, L-689,660 (1-azabicyclo[2.2.2]octane, 3-(6-chloropyrazinyl) maleate), pilocarpine, muscarine, McN-A 343 (4-[[[(3-Chlorophenyl)amino]carbonyl]oxy]-N,N,N-trimethyl-2-butyn-1-aminium chloride), 77-LH-218-1 (1-[3-(4-Butyl-1-piperidinyl) propyl]-3,4-dihydro-2(1H)-quinolinone) and methacholine, preferably at a concentration of 0.001-300 μM.

In any of these embodiments, the differentiation medium may further comprise a BMP pathway activator (e.g. BMP7), preferably at a concentration of 0.01 ng/ml to 500 ng/ml, and/or gastrin, preferably at a concentration of 0.01 nM to 500 nM.

In preferred embodiments, the differentiation medium of the invention comprises (i) one or more receptor tyrosine kinase ligands (e.g. EGF, HGF and/or FGF19), (ii) one or more TGF-beta inhibitors (e.g. A83-01), (iii) a Notch inhibitor (e.g. DAPT and/or DBZ), (iv) a glucocorticoid (e.g. dexamethasone), (v) one or more Wnt inhibitors (e.g. IWP-2 and/or iCRT3), (vi) a GSK-3 inhibitor (e.g. CHIR99021) and (vii) an AP-1 stimulant (e.g. a muscarinic acetylcholine receptor agonist, such as carbachol). In some embodiments, the differentiation medium of the invention further comprises: (viii) a BMP pathway activator (e.g. BMP7) and/or (ix) gastrin.

Accordingly, in some embodiments, the differentiation medium of the invention comprises (i) EGF (e.g. at a concentration of about 50 ng/ml), HGF (e.g. at a concentration of about 25 ng/ml) and FGF19 (e.g. at a concentration of about 100 ng/ml), (ii) A83-01 (e.g. at a concentration of about 0.5 μM), (iii) DAPT (e.g. at a concentration of about 10 μM), (iv) dexamethasone (e.g. at a concentration of about 3 μM), (v) IWP-2 (e.g. at a concentration of about 3 μM) and iCRT3 (e.g. at a concentration of about 50 μM), (vi) CHIR99021 (e.g. at a concentration of about 3 M), (vii) carbachol (e.g. at a concentration of about 100 μM), (viii) BMP7 (e.g. at a concentration of about 25 ng/ml) and (ix) gastrin (e.g. at a concentration of about 10 nM).

These differentiation media are particularly suitable for differentiating liver cells. These media are also envisaged to be useful for closely related tissues, such as pancreas. These media are also envisaged to be useful for the differentiation of epithelial cells more generally.

Splitting

The inventors surprisingly found that differentiation is improved if smaller organoids are cultured in differentiation medium. In particular, the inventors found that splitting a liver organoid culture before adding the organoids to a differentiation medium resulted in a higher efficiency of differentiation (see FIG. 2F). Thus, a greater proportion of the cell population exhibited hepatocyte markers (e.g. albumin and Cyp3A4) and the differentiated cells exhibited higher levels of hepatocyte markers.

Accordingly, in some embodiments, a culture of progenitor cells is split before it is cultured in the differentiation medium. In some embodiments, this splitting occurs after at least three, at least four, at least five, at least six or at least seven days of culturing in an expansion medium. For example, in some embodiments, the progenitor cells, e.g. epithelial stem cells, are cultured in an expansion medium for five days, the culture is then split and then cultured in a differentiation medium of the invention.

In one embodiment, the invention provides a method for culturing a single epithelial stem cell, a population of epithelial stem cells, or an isolated tissue fragment, preferably to generate an organoid, wherein the method comprises:

culturing an epithelial cell, a population of epithelial cells or an isolated tissue fragment in an expansion medium to obtain an expanded cell population (preferably to obtain one or more organoid);

splitting the expansion culture after at least three, at least four, at least five, at least six or at least seven days of culturing in the expansion medium; and culturing the expanded cell population or one or more organoid in a differentiation medium.

In some embodiments, a BMP pathway activator as described herein (e.g. BMP7) is added to the expansion medium before splitting. For example, in some embodiments, BMP7 is added to the expansion medium after at least three, at least four, at least five, at least six or at least seven days of culturing in the expansion medium.

Extracellular Matrix

In some embodiments, the methods for culturing cells, e.g. the methods for expanding and/or differentiating cells, comprise culturing cells in contact with an extracellular matrix (ECM). Any suitable ECM may be used. Cells are preferably cultured in a microenvironment that mimics at least in part a cellular niche in which said cells naturally reside. A cellular niche is in part determined by the cells and by an ECM that is secreted by the cells in said niche. A cellular niche may be mimicked by culturing said cells in the presence of biomaterials or synthetic materials that provide interaction with cellular membrane proteins, such as integrins. An ECM as described herein is thus any biomaterial or synthetic material or combination thereof that mimics the in vivo cellular niche, e.g. by interacting with cellular membrane proteins, such as integrins.

In a preferred method of the invention, cells are cultured in contact with an ECM. "In contact" means a physical or mechanical or chemical contact, which means that for separating said resulting organoid or population of epithelial cells from said extracellular matrix a force needs to be used. In some embodiments, the ECM is a three-dimensional matrix. In some embodiment, the cells are embedded in the ECM. In some embodiments, the cells are attached to an ECM. A culture medium of the invention may be diffused into a three-dimensional ECM.

In another embodiments, the ECM is in suspension, i.e. the cells are in contact with the ECM in a suspension system. In some embodiments, the ECM is in the suspension at a concentration of at least 1%, at least 2% or at least 3%. In some embodiments, the ECM is in the suspension at a concentration of from 1% to about 10% or from 1% to about 5%. The suspension method may have advantages for upscale methods.

One type of ECM is secreted by epithelial cells, endothelial cells, parietal endoderm-like cells (e.g. Englebreth-Holm-Swarm Parietal Endoderm-Like cells described in Hayashi et al. (2004) Matrix Biology 23:47-62) and connective tissue cells. This ECM comprises of a variety of polysaccharides, water, elastin, and glycoproteins, wherein the glycoproteins comprise collagen, entactin (nidogen), fibronectin, and laminin. Therefore, in some embodiments, the ECM for use in the methods of the invention comprises one or more of the components selected from the list: polysaccharides, elastin, and glycoproteins, e.g. wherein the glycoproteins comprise collagen, entactin (nidogen), fibronectin, and/or laminin. For example, in some embodiments, collagen is used as the ECM. Different types of ECM are known, comprising different compositions including different types of glycoproteins and/or different combination of glycoproteins.

The ECM can be provided by culturing ECM-producing cells, such as for example epithelial cells, endothelial cells, parietal endoderm-like cells or fibroblast cells, in a receptacle, prior to the removal of these cells and the addition of isolated tissue fragments or isolated epithelial cells. Examples of extracellular matrix-producing cells are chondrocytes, producing mainly collagen and proteoglycans, fibroblast cells, producing mainly type IV collagen, laminin, interstitial procollagens, and fibronectin, and colonic myofibroblasts producing mainly collagens (type I, III, and V), chondroitin sulfate proteoglycan, hyaluronic acid, fibronectin, and tenascin-C. These are "naturally-produced ECMs": Naturally-produced ECMs can be commercially provided. Examples of commercially available extracellular matrices include: extracellular matrix proteins (Invitrogen) and basement membrane preparations from Engelbreth-Holm-Swarm (EHS) mouse sarcoma cells (e.g. CULTREX® Basement Membrane Extract (Trevigen, Inc.) or MATRIGEL™ (BD Biosciences)).

Therefore, in some embodiments, is a naturally-produced ECM. In some embodiments the ECM is a laminin-containing ECM such as MATRIGEL™ (BD Biosciences). In some embodiments, the ECM is MATRIGEL™ (BD Biosciences), which comprises laminin, entactin, and collagen IV. In some embodiments, the ECM comprises laminin, entactin, collagen IV and heparin sulphate proteoglycan (e.g. CULTREX® Basement Membrane Extract Type 2 (Trevigen, Inc.)). In some embodiments, the ECM comprises at least one glycoprotein, such as collagen and/or laminin. A preferred ECM for use in a method of the invention comprises collagen and laminin. A further preferred ECM comprises laminin, entactin, and collagen IV. Mixtures of naturally-produced or synthetic ECM materials may be used, if desired.

In another embodiment, the ECM may be a synthetic ECM. For instance, a synthetic ECM, such as ProNectin (Sigma Z378666) may be used. In a further example, the ECM may be a plastic, e.g. a polyester, or a hydrogel. In some embodiments, a synthetic matrix may be coated with biomaterials, e.g. one or more glycoprotein, such as collagen or laminin.

A three-dimensional ECM supports culturing of three-dimensional epithelial organoids. The extracellular matrix material will normally be a drop on the bottom of the dish in which cells are suspended. Typically, when the matrix solidifies at 37° C., the medium is added and diffuses into the ECM. The cells in the medium stick to the ECM by interaction with its surface structure, for example interaction with integrins.

The culture medium and/or cells may be placed on, embedded in or mixed with the ECM.

For instance, in some embodiments, the single cell, population of cells, or tissue fragment is embedded in MATRIGEL™, which is optionally growth factor reduced and/or phenol red-free.

In some embodiments, the culture medium is placed on top of the ECM. The culture medium can then be removed and replenished as and when required. In some embodiments, the culture medium is replenished every 1, 2, 3, 4, 5, 6 or 7 days. If components are "added" or "removed" from the media, then this can in some embodiments mean that the media itself is removed from the ECM and then a new media containing the "added" component or with the "removed" component excluded is placed on the ECM.

Progenitor and Stem Cells for Culture and Obtaining Said Cells

The differentiation methods are useful for progenitor cells. Progenitor cells are defined herein as any cells that have differentiation potential. The term "progenitor cells" therefore encompasses stem cells, including, but not limited to adult stem cells, embryonic stem cells and iPS cells. The progenitor cells may be, for example, primary stem cells or expanded stem cells or part-differentiated stem cells. In some embodiments, the progenitor cells are primary cells, meaning obtained directly from live tissue. In other embodiments, the progenitor cells are secondary cells, i.e. cells that have been cultured and/or passaged. In some embodiments, the progenitor cells are expanded cells. The term "expanded" means that the cells have been cultured in vitro in a culture medium that promotes expansion (e.g. proliferation) of cells in preference to differentiation.

In a preferred embodiment, the progenitor cells are adult progenitor cells, i.e. are derived from adult tissue. In some embodiments, the adult progenitor cells are adult stem cells (e.g. adult epithelial stem cells). In this context "adult" includes newly-born baby or child but excludes embryonic or foetal. In some embodiments the progenitor cells are not derived from embryonic stem cells or embryonic stem cell lines, for example human embryonic stem cells or human embryonic stem cell lines. In some embodiments, the progenitor cells are not derived from umbilical cord and/or placental tissue.

In a preferred embodiment, the progenitor cells are epithelial progenitor cells. For example, in a preferred embodiment, the progenitor cells are derived from epithelial tissue, more preferably adult epithelial tissue. Epithelial tissues include the liver, pancreas, intestine, stomach, prostate, lung, breast, ovary, salivary gland, hair follicle, skin, oesophagus, ear, bladder or thyroid. Thus in some embodiments; the progenitor cells are obtained from the liver, pancreas, intestine, stomach, prostate, lung, breast, ovary, salivary gland, hair follicle, skin, oesophagus, ear, bladder or thyroid. In some embodiments, the progenitor cells are obtained from the liver or pancreas. In a preferred embodiment, the progenitor cells are obtained from the liver.

In a preferred embodiment, the progenitor cells are mammalian cells. For example, in a preferred embodiment, the cells are derived from mammalian tissue. For example, in some embodiments the progenitor cells are human cells. In some embodiments the progenitor cells are from a laboratory animal (e.g. mouse, rabbit, rat, guinea pig), a companion animal (e.g. dog, cat, horse) or a farm animal (e.g. cow, pig, sheep, goat).

Primary cells represent the best experimental models for in vivo situations. In a preferred embodiment of the invention, the progenitor cells are (or are derived from) primary progenitor cells (e.g. primary epithelial stem cells). Primary cell cultures can be passaged to form secondary cell cultures. With the exception of cancer cells, traditional secondary epithelial cell cultures have a limited lifespan. After a certain number of population doublings (e.g. 50-100 generations) cells undergo the process of senescence and stop dividing. Cells from secondary cultures can become immortalized to become continuous cell lines. Immortalization can occur spontaneously, or may be virally- or chemically-induced. Immortalized cell lines are also known as transformed cells. In a preferred embodiment of the invention, the cells are obtained from expanded epithelial stem cell cultures, preferably expanded organoids, which have been expanded and/or passaged without immortalisation or transformation. In some embodiments, these expanded epithelial cultures or organoids may be genetically heterogeneous (unlike traditional cell lines). Thus in some embodiments, the progenitor cells are not immortalised or transformed cells or are not derived from an immortalised cell line or a transformed cell line.

The progenitor cells may be obtained by any suitable method, for example, as described in WO 2010/090513, WO 2012/014076, WO 2012/168930 or WO 2015/173425. In some embodiments, cells are isolated by collagenase digestion, for example, as described in the examples and in Dorell et al., 2008 (Hepatology. 2008 October; 48 (4): 1282-91. Surface markers for the murine oval cell response. Dorrell C, Erker L, Lanxon-Cookson K M, Abraham S L, Victoroff T, Ro S, Canaday P S, Streeter P R, Grompe M). In some embodiments, collagenase digestion is performed on a tissue biopsy. In some embodiments, collagenase and accutase digestion are used to obtain the progenitor cells for use in the invention.

In some embodiments, progenitor cell is an epithelial stem cell that expresses Lgr5. An organoid is preferably obtained using a cell from an adult tissue, preferably an epithelial stem cell from an adult tissue, more preferably an epithelial stem cell that expresses Lgr5.

In some embodiments the progenitor cells are normal cells, meaning that the cells have a normal karyotype, genotype and/or phenotype. In alternative embodiments, the progenitor cells are disease cells, meaning that they have a disease karyotype, genotype and/or phenotype. For example, in some embodiments, the progenitor cells are cancer cells. Thus, it is envisaged, for example, that the epithelial stem cells may be Lgr5 positive cancer stem cells. Accordingly, the cells may be obtained from a tumour, if required. In alternative embodiments, the progenitor cells are diseased progenitor cells, for example progenitor cells infected with intracellular pathogens (e.g. bacteria, viruses or parasites).

Exemplary Methods

The invention provides a method for differentiating progenitor cells, wherein said method comprises culturing the cells in a differentiation medium described herein. In a preferred embodiment, the cells are cultured in contact with an ECM as described herein.

The invention also provides a method for culturing progenitor cells, wherein said method comprises culturing the cells in an expansion medium and subsequently culturing the cells in a differentiation medium described herein. In some embodiments, the cells are cultured in contact with an ECM as described herein during the expansion and/or differentiation steps. In some embodiments, the expansion medium is removed prior to culturing the cells in the differentiation medium, e.g. by repeated washings or by splitting the cell culture.

The invention provides a method for culturing a single epithelial stem cell, a population of epithelial stem cells, or an isolated tissue fragment, preferably to obtain an organoid, wherein the method comprises:

- culturing an epithelial stem cell, a population of epithelial stem cells or an isolated tissue fragment in an expansion medium to provide an expanded cell population; and
- culturing the expanded cell population in a differentiation medium.

The invention also provides a method for differentiating a single progenitor cell or a population of progenitor cells, wherein the method comprises:

- culturing a progenitor cell or a population of progenitor cells in a differentiation medium.

The differentiation medium may be any differentiation medium described herein. For example, in some embodiments, the differentiation medium comprises (i) one or more receptor tyrosine kinase ligands (e.g. EGF, HGF and/or FGF19), (ii) one or more TGF-beta inhibitors (e.g. A83-01), (iii) a Notch inhibitor (e.g. DAPT and/or DBZ), (iv) a glucocorticoid (e.g. dexamethasone), (v) one or more Wnt inhibitors (e.g. IWP-2 and/or iCRT3), (vi) a GSK-3 inhibitor (e.g. CHIR99021) and (vii) an AP-1 stimulant (e.g. a muscarinic acetylcholine receptor agonist, such as carbachol). In some embodiments, the differentiation medium of the invention further comprises: (viii) a BMP pathway activator (e.g. BMP7) and/or (ix) gastrin.

The expansion medium may be any suitable expansion medium for epithelial stem or progenitor cells, preferably a suitable expansion medium for epithelial stem cells (e.g. as described in WO 2010/090513, WO 2012/014076, WO 2012/168930 or WO 2015/173425).

In some embodiments, the expansion medium comprises one or more receptor tyrosine kinase ligands (e.g. EGF, HGF and/or FGF10), nicotinamide and one or more Wnt agonists (e.g. Rspondin conditioned medium and/or Wnt conditioned medium).

In some embodiments, the expansion medium comprises one or more receptor tyrosine kinase ligands (e.g. EGF, HGF and/or FGF10), one or more Wnt agonists (e.g. Rspondin conditioned medium and/or Wnt conditioned medium) and one or more TGF-beta inhibitors (e.g. A83-01). In some embodiments, the expansion medium comprises one or more receptor tyrosine kinase ligands (e.g. EGF, HGF and/or FGF10), nicotinamide, one or more Wnt agonists (e.g. Rspondin conditioned medium and/or Wnt conditioned medium) and one or more TGF-beta inhibitors (e.g. A83-01).

In any of these embodiments, the expansion medium may further comprise a cAMP pathway activator (e.g. forskolin), gastrin and/or a BMP inhibitor (e.g. Noggin).

For example, in some embodiments (e.g. in a preferred embodiment for the liver), the expansion medium comprises (i) EGF (e.g. at about 50 ng/ml), HGF (e.g. at about 25 ng/ml) and FGF10 (e.g. at about 100 ng/ml); (ii) A83-01 (e.g. at about 5 μM); (iii) Rspondin conditioned medium (e.g. at about 10%); (iv) nicotinamide (e.g. at about 0.01 M); (v) forskolin (e.g. at about 10 μM) and (vi) gastrin (e.g. at about 10 nM). In some embodiments, the expansion medium further comprises n-Acetylcysteine (e.g. at about 1.25 mM), 1×N2 and 1×B27 (optionally 1×B27 without vitamin A).

Preferably, the cells are expanded to generate one or more (e.g. at least 2, 3, 4, 5, 6, 10, 15, 20 or more than 20) organoids prior to differentiation.

In some embodiments, cells are initially cultured in an expansion medium described herein and, once successful organoids have been established, the expansion medium is replaced with a differentiation medium described herein. Accordingly, in some embodiments after one or more (e.g. after two, three, four, five, six, seven, eight, nine, ten or more) passages, the expansion medium is replaced with a differentiation medium.

As will be apparent to the skilled reader, the preferred culture methods of the invention are advantageous because feeder cells are not required. Feeder cell layers are often used to support the culture of stem cells, and to inhibit their differentiation. A feeder cell layer is generally a monolayer of cells that is co-cultured with, and which provides a surface suitable for growth of, the cells of interest. The feeder cell layer provides an environment in which the cells of interest can grow. Feeder cells are often mitotically inactivated (e.g. by irradiation or treatment with mitomycin C) to prevent their proliferation. The use of feeder cells is undesirable, because it complicates passaging of the cells (the cells must be separated from the feeder cells at each passage, and new feeder cells are required at each passage). The use of feeder cells can also lead to contamination of the desired cells with the feeder cells. This is clearly problematic for any medical applications, and even in a research context, complicates analysis of the results of any experiments performed on the cells. As noted elsewhere herein, the culture media of the invention are particularly advantageous because they can be used to culture cells without feeder cell contact, i.e. the methods of the invention do not require a layer of feeder cells to support the cells whose growth is being sponsored.

Accordingly, the compositions of the invention may be feeder cell-free compositions. A composition is conventionally considered to be feeder cell-free if the cells in the composition have been cultured for at least one passage in the absence of a feeder cell layer. A feeder cell-free composition of the invention will normally contain less than about 5%, less than about 4%, less than about 3%, less than about 2%, less than about 1% feeder cells (expressed as a % of the total number of cells in the composition) or preferably no feeder cells at all.

In a further aspect, there is provided a method for obtaining a population of differentiated cells or an organoid, wherein the method comprises culturing progenitor cells in a differentiation medium of the invention. Preferably, the method comprises culturing the progenitor cells in a differentiation medium of the invention using a differentiation method as described herein.

In some embodiments, the method comprises obtaining the organoid/population of differentiated cells from a single epithelial stem cell. In another embodiment, the method comprises obtaining the organoid/population of differentiated cells from a population of epithelial stem cells, or from an epithelial tissue fragment.

In a particular embodiment, there is provided a method for obtaining a differentiated organoid, wherein the method comprises culturing epithelial progenitor cells (e.g. epithelial stem cells, optionally expressing Lgr5) in a differentiation medium of the invention, preferably wherein the epithelial progenitor cells are in contact with an ECM, preferably a three-dimensional ECM.

In some embodiments, the method comprises culturing the progenitor cells in an expansion medium for a period of time, for example, 3 days to 10 weeks, 1 to 10 weeks, 1 to 4 weeks or 10 days to 3 weeks, and then passaging the cells (e.g. dissociating the cells to a single cell density, seeding one or more cells at a ratio of 1 cell per container (e.g. per well)), continuing to expand the cells using an expansion medium for a period of time, for example, 3 days to 10 weeks, 1 to 10 weeks, 1 to 4 weeks or 10 days to 3 weeks and repeating the passaging and expanding steps at least once, at least twice, at least three times, at least four times, at least five times, at least six times, at least seven times, at least eight times, at least nine times, at least ten times, at least eleven times, at least twelve times, at least thirteen times or at least fourteen times, prior to differentiating the cells.

In some embodiments, the method comprises culturing the progenitor cells in a differentiation medium for at least 1, at least 2, at least 3, at least 4, at least 5, at least 6, at least 7, at least 8, at least 9, at least 10, at least 11, at least 12, at least 13, at least 14 days. In some embodiments, the method comprises culturing the progenitor cells in a differentiation medium for about 1 to about 20 days, for about 1 to about 10 days or for about 1 to about 5 days.

Following differentiation, the method may further comprise obtaining and/or isolating one or more differentiated cells or a differentiated organoid. For example, following culture of the progenitor cells, it may be useful to remove one or more cells and/or one or more organoids cultured in the culture medium from the culture medium for use in subsequent applications. Any one of a number of physical methods of separation known in the art may be used to select the cells of the invention and distinguish these from other cell types. Such physical methods may involve FACS and various immuno-affinity methods based upon makers specifically expressed by the cells of the invention.

In one embodiment, the cells may be isolated by FACS utilizing an antibody, for example, against one of these markers. As will be apparent to one skilled in the art, this may be achieved through a fluorescent labeled antibody, or through a fluorescent labeled secondary antibody with binding specificity for the primary antibody. Examples of suitable fluorescent labels includes, but is not limited to, FITC, ALEXA FLUOR® 488, GFP, CFSE, CFDA-SE, DYLIGHT™ 488, PE, PerCP, PE-ALEXA FLUOR® 700, PE-CY™5 (TRI-COLOR®), PE-CY™5.5, PI, PE-ALEXA FLUOR® 750, and PE-CY™7. This list is provided by way of example only, and is not intended to be limiting.

Alternatively, cells may be isolated by immuno-affinity purification, which is a separation method well known in the art. This method relies upon the immobilisation of antibodies on a purification column. The cell sample is then loaded onto the column, allowing the appropriate cells to be bound by the antibodies, and therefore bound to the column. Following a washing step, the cells are eluted from the column using a competitor which binds preferentially to the immobilised antibody, and permits the cells to be released from the column.

It will be apparent to a person skilled in the art that immuno-affinity purification using an immobilised antibody will provide a purified cell population. However, in some embodiments, it may be preferable to purify the cell population further by performing a further round of immuno-affinity purification using one or more of the other identifiable markers and use an aliquot of the isolated clones to ascertain the expression of other relevant intracellular markers.

It will be apparent to a person skilled in the art that the sequential purification steps are not necessarily required to involve the same physical method of separation.

Differentiated Cells and Organoids

The invention further provides a differentiated organoid or a population of one or more differentiated cells.

A differentiated organoid is a three-dimensional structure comprising differentiated epithelial cell types. A differentiated organoid is typically self-organising, meaning that the three-dimensional arrangement of the cells in the organoid occurs spontaneously as the cells differentiate. In some embodiments, a differentiated organoid is derived from epithelial stem cells, optionally expressing Lgr5.

In one embodiment, the invention provides a differentiated organoid or a population of one or more differentiated cells obtainable or obtained by a method of the invention, for example, which comprises culturing progenitor cells in a differentiation medium of the invention, preferably wherein the progenitor cells are in contact with a three-dimensional ECM.

A 'population' of cells is any number of cells greater than 1, but is preferably at least 10 cells, at least 50 cells, at least 100 cells, at least 500 cells, at least $1\times10^3$ cells, at least $1\times10^4$ cells, at least $1\times10^5$ cells, at least $1\times10^6$ cells, at least $1\times10^7$ cells, at least $1\times10^8$ cells, or at least $1\times10^9$ cells. A differentiated organoid according to the present invention may comprise a population of cells of at least 10 cells, at least 50 cells, at least 100 cells, at least 500 cells, at least $1\times10^3$ cells, at least $1\times10^4$ cells, at least $1\times10^5$ cells, at least $1\times10^6$ cells, at least $1\times10^7$ cells or more. In some embodiments, each organoid comprises between approximately $1\times10^3$ cells and $5\times10^3$ cells; generally, 10-20 organoids may be grown together in one well, for example of a 24 well plate.

It is clear to the skilled person that an organoid of the invention is not a naturally occurring tissue fragment and/or does not comprise a blood vessel. For example, in the case of a liver organoid of the invention, it does not comprise a naturally occurring liver lobule or a naturally occurring bile duct.

Organoids of the invention are, for example, distinguished from naturally occurring tissue because they comprise only epithelial cell types (and not mesenchymal cells or other structural cell types). Thus in some embodiments, the differentiated organoid of the invention comprises only epithelial cells. In some embodiments, the differentiated organoids do not comprise non-epithelial cells. For example, in a particular embodiment, the differentiated organoids do not comprise mesenchymal cells.

The differentiation medium described herein preferably induces or promotes a specific differentiation of cells during at least five days of culture. Differentiation may be measured by detecting the presence of a specific marker associated with the particular tissue lineage, e.g. the liver lineage, as defined herein. Differentiation may be measured by detecting the presence of a specific marker associated with the tissue lineage, e.g. the liver lineage, as defined herein. Depending on the identity of the marker, the expression of said marker may be assessed by RTPCR or immuno-histochemistry after at least 5, 7, 8, 9, 10, 11, 12, 13, 14, 15, 16 or more days of culture in a differentiation medium as defined herein.

The term "expressed" is used to describe the presence of a marker within a cell. In order to be considered as being expressed, a marker must be present at a detectable level. By "detectable level" is meant that the marker can be detected using one of the standard laboratory methodologies such as PCR, blotting or FACS analysis. A gene is considered to be expressed by a cell of the population of the invention if expression can be reasonably detected after 30 PCR cycles, which corresponds to an expression level in the cell of at least about 100 copies per cell. The terms "express" and "expression" have corresponding meanings. At an expression level below this threshold, a marker is considered not to be expressed. The comparison between the expression level of a marker in a cell of the invention, and the expression level of the same marker in another cell, such as for example an embryonic stem cell, may preferably be conducted by comparing the two cell types that have been isolated from the same species. Preferably this species is a mammal, and more preferably this species is human. Such comparison may conveniently be conducted using a reverse transcriptase polymerase chain reaction (RT-PCR) experiment.

The differentiated organoid of the invention or the population of differentiated cells of the invention preferably comprises at least 50% viable cells, more preferred at least 60% viable cells, more preferred at least 70% viable cells, more preferred at least 80% viable cells, more preferred at least 90% viable cells. Viability of cells may be assessed using Hoechst staining or Propidium Iodide staining in FACS. The viable cells preferably possess corresponding in vivo functions or characteristics. For example, viable liver cells preferably possess hepatic functions or characteristics or hepatocytes.

In some embodiments, the organoid is a liver, pancreas, intestine, stomach, prostate, lung, breast, ovary, salivary gland, hair follicle, skin, oesophagus, ear, bladder or thyroid organoid. This means that the organoid is derived from liver, pancreas, intestine, stomach, prostate, lung, breast, ovary, salivary gland, hair follicle, skin, oesophagus, ear, bladder or thyroid cells. In some embodiments, the organoid is a liver or pancreas organoid. In preferred embodiments, the organoid is a liver organoid.

In some embodiments, the population of differentiated cells of the invention is derived from liver, pancreas, intestine, stomach, prostate, lung, breast, ovary, salivary gland, hair follicle, skin, oesophagus, ear, bladder or thyroid cells. In some embodiments, the population of differentiated cells is derived from liver or pancreas cells. In preferred embodiments, the differentiated population of cell is derived from liver cells.

The inventors have shown that liver organoids obtained by the methods of the invention are improved because a greater proportion of the cells in these organoids are differentiated than in the differentiated liver organoids previously described in WO2012/014076 and WO 2015/173425 and a greater proportion of the cells in these organoids are differentiated than in the liver organoids differentiated in the old differentiation medium (DM) described in Example 1 (e.g. a greater proportion of the cell population in the organoids of the invention express hepatocyte markers). In addition, the differentiated cells in the organoids of the invention more closely resemble hepatocytes than the differentiated cells in the differentiated liver organoids previously described in WO2012/014076 and WO 2015/173425 and the differentiated cells in the organoids of the invention more closely resemble hepatocytes than the differentiated cells in the liver organoids differentiated in the old differentiation medium (DM) described in Example 1 (e.g. the average expression level of hepatocyte markers in individual differentiated cells in the organoids of the invention is higher). Furthermore, the liver organoids have reduced biliary fate commitment compared to liver organoids previously described in WO2012/014076 and WO 2015/173425, or liver organoids differentiated in the old differentiation medium (DM) described in Example 1.

In some embodiments, the differentiated organoid of the invention is a differentiated liver organoid in which at least 10%, at least 20%, at least 30%, at least 40%, at least 50%, at least 60%, at least 70%, at least 80%, at least 90% or at least 99% of the cells express hepatocyte markers (e.g. albumin, HNF4a, ASGPR, CYP1A2 and/or CYP3A4). In some embodiments, mRNA expression is measured by immunofluorescence staining.

In some embodiments, the population of differentiated cells is a population of differentiated liver cells in which at least 10%, at least 20%, at least 30%, at least 40%, at least 50%, at least 60%, at least 70%, at least 80%, at least 90% or at least 99% of the cells express hepatocyte markers (e.g. albumin, HNF4a, ASGPR, CYP1A2 and/or CYP3A4). In some embodiments, mRNA expression is measured by immunofluorescence staining.

In some embodiments, the differentiated organoid of the invention is a differentiated liver organoid in which there are at least 10%, at least 20%, at least 30%, at least 40%, at least 50%, at least 60%, at least 70%, at least 80%, at least 90% or at least 100%, at least 200% or at least 300% more cells expressing hepatocyte markers (e.g. albumin, HNF4a, ASGPR, CYP1A2 and/or CYP3A4), than the corresponding liver organoid differentiated in the previous DM medium (described in Example 1). In some embodiments, mRNA expression is measured by immunofluorescence staining. In this context, "corresponding liver organoid" means a liver organoid from the same source, e.g. derived from the same organoid culture and the same individual's cells. The same definition applies elsewhere in this section.

In some embodiments, the population of differentiated cells is a population of differentiated liver cells in which there are at least 10%, at least 20%, at least 30%, at least 40%, at least 50%, at least 60%, at least 70%, at least 80%, at least 90% or at least 100%, at least 200% or at least 300% more cells expressing hepatocyte markers (e.g. albumin, HNF4a, ASGPR, CYP1A2 and/or CYP3A4), than the corresponding population of liver cells differentiated in the previous DM medium (described in Example 1). In some embodiments, mRNA expression is measured by immunofluorescence staining. In this context, "corresponding population of liver cells" means a population of liver cells from the same source, i.e. derived from the same cell culture and the same individual's cells. The same definition applies elsewhere in this section.

As outlined in detail below, the differentiated liver organoid or the population of differentiated liver cells may be defined based on the mRNA expression level of various markers (e.g. albumin, HNF4, SerpinA1, ASPGR, Cyp1A2, Cyp3A4, CK7 and/or CK19) relative to the mRNA expression level of a house-keeping gene (e.g. GAPDH). In some embodiments, the mRNA expression levels of one or more of these markers and the house-keeping gene are determined using RT-PCR. In some embodiments, the determination comprises: (a) isolation of mRNA from the differentiated liver organoid of the invention or the population of differentiated liver cells of the invention, (b) reverse transcription of the isolated mRNA into cDNA, (c) PCR amplification of cDNA that corresponds to (i) the marker of interest (e.g. albumin, HNF4, SerpinA1, ASPGR, Cyp1A2, Cyp3A4, CK7 or CK19) and (ii) the house-keeping gene (e.g. GAPDH) and (d) quantification of the amount of PCR product obtained from PCR amplification of cDNA that corresponds to the marker of interest (e.g. albumin, HNF4, SerpinA1, ASPGR, Cyp1A2, Cyp3A4, CK7 or CK19) relative to the amount of PCR product obtained from PCR amplification of cDNA that corresponds to the house-keeping gene (e.g. GAPDH).

In some embodiments, the differentiated organoid of the invention is a differentiated liver organoid in which the mRNA expression level of albumin is at least $1.0\times10^{-2}$, at least $1.0\times10^{-1}$, at least $1.0\times10^{0}$, at least $1.0\times10^{1}$ or at least $5.0\times10^{1}$ (relative to GAPDH expression).

In some embodiments, the population of differentiated cells is a population of differentiated liver cells in which the mRNA expression level of albumin is at least $1.0\times10^{-2}$, at least $1.0\times10^{-1}$, at least $1.0\times10^{0}$, at least $1.0\times10^{1}$ or at least $5.0\times10^{1}$ (relative to GAPDH expression).

In some embodiments, the differentiated organoid of the invention is a differentiated liver organoid in which the mRNA expression level of HNF4a is at least 0.002, at least 0.003, at least 0.004, at least 0.005, at least 0.006, at least 0.007, at least 0.008, at least 0.009, or at least 0.01 (relative to GAPDH expression).

In some embodiments, the population of differentiated cells is a population of differentiated liver cells in which the mRNA expression level of HNF4a is at least 0.002, at least 0.003, at least 0.004, at least 0.005, at least 0.006, at least 0.007, at least 0.008, at least 0.009, or at least 0.01 (relative to GAPDH expression).

In some embodiments, the differentiated organoid of the invention is a differentiated liver organoid in which the mRNA expression level of SerpinA1 is at least 1, at least 2, at least 3, at least 4, at least 5, at least 6, at least 7, at least 8, at least 9 or at least 10 (relative to GAPDH expression).

In some embodiments, the population of differentiated cells is a population of differentiated liver cells in which the mRNA expression level of SerpinA1 is at least 1, at least 2, at least 3, at least 4, at least 5, at least 6, at least 7, at least 8, at least 9 or at least 10 (relative to GAPDH expression).

In some embodiments, the differentiated organoid of the invention is a differentiated liver organoid in which the mRNA expression level of ASPGR is at least 0.001, at least 0.002, at least 0.003, at least 0.004, at least 0.005, at least 0.006, at least 0.007, at least 0.008, at least 0.009, at least 0.01, at least 0.02, at least 0.03, at least 0.04, at least 0.05, at least 0.06, at least 0.07, at least 0.08, at least 0.09 or at least 0.1 (relative to GAPDH expression).

In some embodiments, the population of differentiated cells is a population of differentiated liver cells.

In some embodiments, the differentiated organoid of the invention is a differentiated liver organoid in which the mRNA expression level of Cyp1A2 is at least $2.0\times10^{-5}$, at least $3.0\times10^{-5}$, at least $4.0\times10^{-5}$, at least $5.0\times10^{-5}$, at least $6.0\times10^{-5}$, at least $7.0\times10^{-5}$, at least $8.0\times10^{-5}$, at least $9.0\times10^{-5}$, at least $1.0\times10^{-4}$, at least $2.0\times10^{-4}$, at least $3.0\times10^{-4}$, at least $4.0\times10^{-4}$, at least $5.0\times10^{-4}$, at least $7.0\times10^{-4}$, at least $1.0\times10^{-3}$, at least $5.0\times10^{-3}$, at least $1.0\times10^{-2}$, or at least $5.0\times10^{-2}$ (relative to GAPDH expression).

In some embodiments, the population of differentiated cells is a population of differentiated liver cells in which the mRNA expression level of Cyp1A2 is at least $2.0\times10^{-5}$, at least $3.0\times10^{-5}$, at least $4.0\times10^{-5}$, at least $5.0\times10^{-5}$, at least $6.0\times10^{-5}$, at least $7.0\times10^{-5}$, at least $8.0\times10^{-5}$, at least $9.0\times10^{-5}$, at least $1.0\times10^{-4}$, at least $2.0\times10^{-4}$, at least $3.0\times10^{-4}$, at least $4.0\times10^{-4}$, at least $5.0\times10^{-4}$, at least $7.0\times10^{-4}$, at least $1.0\times10^{-3}$, at least $5.0\times10^{-3}$, at least $1.0\times10^{-2}$, or at least $5.0\times10^{-2}$ (relative to GAPDH 1 expression).

In some embodiments, the differentiated organoid of the invention is a differentiated liver organoid in which the mRNA expression level of Cyp3A4 is at least 0.1, at least 0.2, at least 0.3, at least 0.4, at least 0.5, at least 0.6, at least 0.7, at least 0.8, at least 0.9 or at least 1.0 (relative to GAPDH expression). In some embodiments, the differentiated organoid of the invention is a differentiated liver organoid in which the mRNA expression level of Cyp3A4 is at least 10%, at least 20%, at least 30%, at least 40%, at least 50%; at least 60%, at least 70%, at least 80%, at least 90% or at least 99% of the expression level found in normal human hepatocytes.

In some embodiments, the population of differentiated cells is a population of differentiated liver cells in which the mRNA expression level of Cyp3A4 is at least 0.1, at least 0.2, at least 0.3, at least 0.4, at least 0.5, at least 0.6, at least 0.7, at least 0.8, at least 0.9 or at least 1.0 (relative to GAPDH expression). In some embodiments, the differentiated organoid of the invention is a differentiated liver organoid in which the mRNA expression level of Cyp3A4 is at least 10%, at least 20%, at least 30%, at least 40%, at least 50%, at least 60%, at least 70%, at least 80%, at least 90% or at least 99% of the expression level found in normal human hepatocytes.

In some embodiments, the differentiated organoid of the invention is a differentiated liver organoid in which the mRNA expression level of CK7 is less than 0.08, less than 0.07, less than 0.06, less than 0.05, less than 0.04, less than 0.03, less than 0.02, less than 0.01, less than 0.009, less than 0.008, less than 0.007, less than 0.006, less than 0.005, less than 0.004, less than 0.003 or less than 0.002 (relative to GAPDH expression).

In some embodiments, the population of differentiated cells is a population of differentiated liver cells in which the mRNA expression level of CK7 is less than 0.08, less than 0.07, less than 0.06, less than 0.05, less than 0.04, less than 0.03, less than 0.02, less than 0.01, less than 0.009, less than 0.008, less than 0.007, less than 0.006, less than 0.005, less than 0.004, less than 0.003 or less than 0.002 (relative to GAPDH expression).

In some embodiments, the differentiated organoid of the invention is a differentiated liver organoid in which the mRNA expression level of CK19 is less than 0.03, less than 0.02, less than 0.01, less than 0.009, less than 0.008, less than 0.007, less than 0.006, less than 0.005, less than 0.004, less than 0.003 or less than 0.002 (relative to GAPDH expression). In some embodiments, the mRNA expression level of CK19 is less than 10-fold, less than 9-fold, less than 8-fold, less than 7-fold, less than 6-fold, less than 5-fold, less than 4-fold, less than 3-fold or less than 2-fold higher than the mRNA expression level of CK19 in normal human hepatocytes.

In some embodiments, the population of differentiated cells is a population of differentiated liver cells in which the mRNA expression level of CK19 is less than 0.03, less than 0.02, less than 0.01, less than 0.009, less than 0.008, less than 0.007, less than 0.006, less than 0.005, less than 0.004, less than 0.003 or less than 0.002 (relative to GAPDH expression). In some embodiments, the mRNA expression level of CK19 is less than 10-fold, less than 9-fold, less than 8-fold, less than 7-fold, less than 6-fold, less than 5-fold, less than 4-fold, less than 3-fold or less than 2-fold higher than the mRNA expression level of CK19 in normal human hepatocytes.

In some embodiments, the differentiated organoid of the invention is a differentiated liver organoid in which the average Cyp3A4 activity is at least 10%, at least 20%, at least 30%, at least 40%, at least 50%, at least 60%, at least 70%, at least 80%, at least 90% or at least 99% of the average Cyp3A4 activity found in normal human hepatocytes.

In some embodiments, the population of differentiated cells is a population of differentiated liver cells in which the average Cyp3A4 activity is at least 10%, at least 20%, at least 30%, at least 40%, at least 50%, at least 60%, at least 70%, at least 80%, at least 90% or at least 99% of the average Cyp3A4 activity found in normal human hepatocytes.

In some embodiments, Cyp3A4 activity is measured using a P450-GLO™ assay (Promega). A P450-GLO™ assay comprises a luminescent method for measuring cytochrome P450 activity. In particular, a conventional cytochrome P450 reaction is performed by incubating the cytochrome P450 and a luminogenic cytochrome P450 substrate. The substrates of the P450-GLO™ assays are derivatives of beetle luciferin. The derivatives are converted by cytochrome P450s to luciferin, which in turn reacts with luciferase to produce light. The amount of light produced is directly proportional to cytochrome P450 activity. In some embodiments, the unit of measurement for Cyp3A4 activity is luminescence/ml/1000 cells.

In some embodiments, the differentiated organoid of the invention is a differentiated liver organoid in which the level of albumin secretion is at least 1%, at least 2%, at least 3%, at least 5%, at least 10%, at least 30%, at least 30%, at least 40%, at least 50%, at least 60%, at least 70%, at least 80%, at least 90% or at least 99% of the level of albumin secretion found in normal human hepatocytes. In some embodiments, the unit of measurement for albumin secretion is ng/$10^6$ cells/24 hours. In some embodiments, the level of albumin secretion is at least 100 ng/$10^6$ cells/24 hours, at least 200 ng/$10^6$ cells/24 hours, at least 500 ng/$10^6$ cells/24 hours, at least 1000 ng/$10^6$ cells/24 hours or at least 2000 ng/$10^6$ cells/24 hours.

In some embodiments, albumin secretion is measured by an enzyme linked immunosorbent assay (ELISA). For example, a Human Albumin ELISA Kit (Bethyl Laboratories, Inc.) may be used, which is based on a sandwich ELISA. The principles upon which the Human Albumin ELISA Kit is based are set out in the following paragraph. However, any suitable ELISA kit may be used.

Human albumin present in the test sample may be captured by anti-human albumin antibody that has been preadsorbed on the surface of microtiter wells. After sample binding, unbound proteins and molecules are washed off, and a biotinylated detection antibody is added to the wells to bind to the captured albumin. A streptavidin-conjugated horseradish peroxidase (SA-HRP) is then added to catalyze a colorimetric reaction with the chromogenic substrate TMB (3,3',5,5'-tetramethylbenzidine). The colorimetric reaction produces a blue product, which turns yellow when the reaction is terminated by addition of dilute sulfuric acid. The absorbance of the yellow product at 450 nm is proportional to the amount of albumin analyte present in the sample and a four-parameter standard curve can be generated. The albumin concentrations in the test samples can then be quantified by interpolating their absorbance from the standard curve generated in parallel with the samples. After factoring sample dilutions, the albumin concentrations in the original sample can finally be calculated.

An overview of an exemplary procedure for the Human Albumin ELISA Kit is provided below:

(1) Add 100 μl of standard or sample to designated wells. Run each standard or sample in duplicate.
(2) Cover the plate and incubate at room temperature (20-25° C.) for 1 hour.
(3) Wash the plate four times.
(4) Add 100 μl of anti-albumin detection antibody to each well.
(5) Cover the plate and incubate at room temperature for 1 hour.
(6) Wash the plate four times.
(7) Add 100 μl of HRP Solution A to each well.
(8) Cover the plate and incubate at room temperature for 30 minutes.
(9) Wash the plate four times.
(10) Add 100 μl of TMB substrate solution to each well.
(11) Incubate the plate in the dark at room temperature for 30 minutes.
(12) Stop the reaction by adding 100 μl of stop solution to each well.
(13) Measure absorbance on a plate reader at 450 nm.

In some embodiments, the population of differentiated cells is a population of differentiated liver cells in which the level of conversion of Midazolam to 1-OH-Midazolam is at least 1 mg/L/$10^6$ cells, at least 1.5 mg/L/$10^6$ cells, at least 2 mg/L/$10^6$ cells, at least 2.5 mg/L/$10^6$ cells, at least 3 mg/L/$10^6$ cells, at least 3.5 mg/L/$10^6$ cells, or at least 4 mg/L/$10^6$ cells.

In some embodiments, the differentiated organoid of the invention is a differentiated liver organoid in which the level of conversion of Midazolam to 1-OH-Midazolam is at least 1 mg/L/$10^6$ cells, at least 1.5 mg/L/$10^6$ cells, at least 2 mg/L/$10^6$ cells, at least 2.5 mg/L/$10^6$ cells, at least 3 mg/L/$10^6$ cells, at least 3.5 mg/L/$10^6$ cells, or at least 4 mg/L/$10^6$ cells.

In some embodiments, the differentiated liver organoid of the invention or the population of differentiated liver cells has at least 5%, at least 10%, at least 20%, at least 30%, at least 40%, at least 50%, at least 60%, at least 70%, at least 80%, at least 90% or at least 100%, at least 2-fold, at least 5-fold, at least 10-fold or at least 100-fold greater expression of one or more (or all) hepatocyte markers selected from albumin, HNF4a, ASGPR, CYP1A2 and CYP3A4, compared to the corresponding liver organoid or population of differentiated liver cells differentiated in the previous DM medium (described in Example 1) as determined using a suitable mRNA expression assay (e.g. as described herein).

In some embodiments, the differentiated liver organoid of the invention or the population of differentiated liver cells has at least 5%, at least 10%, at least 20%, at least 30%, at least 40%, at least 50%, at least 60%, at least 70%, at least 80%, at least 90% or at least 100%, at least 2-fold, at least 5-fold, at least 10-fold or at least 100-fold lower expression of one or more biliary marker selected from CK7 and/or CK19, compared to the corresponding liver organoid or population of differentiated liver cells differentiated in the previous DM medium (described in Example 1) as determined using a suitable mRNA expression assay (e.g. as described herein).

In some embodiments, the differentiated liver organoid of the invention or the population of differentiated liver cells has at least 5%, at least 10%, at least 20%, at least 30%, at least 40%, at least 50%, at least 60%, at least 70%, at least 80%, at least 90% or at least 100%, at least 2-fold, at least 3-fold or at least 5-fold greater midazolam metabolism, compared to the corresponding liver organoid or population of differentiated liver cells differentiated in the previous DM medium (described in Example 1), as determined using a suitable assay for midazolam metabolism (e.g. as known in the art).

In some embodiments, the differentiated liver organoid of the invention or the population of differentiated liver cells has average Cyp3A4 activity which is at least 10%, at least 20%, at least 30%, at least 40%, at least 50%, at least 60%, at least 70%, at least 80%, at least 90% or at least 100%, at least 2-fold, at least 5-fold, at least 10-fold or at least 100-fold, compared to the corresponding liver organoid or population of differentiated liver cells differentiated in the previous DM medium (described in Example 1), as determined using a suitable assay for Cyp3A4 activity (e.g. as using a P450-GLO™ assay (Promega), as described herein).

In some embodiments, the differentiated liver organoid of the invention or the population of differentiated liver cells has average Cyp1A2 activity which is at least 10%, at least 20%, at least 30%, at least 40%, at least 50%, at least 60%, at least 70%, at least 80%, at least 90% or at least 100%, at least 2-fold, at least 5-fold, at least 10-fold or at least 100-fold, compared to the corresponding liver organoid or population of differentiated liver cells differentiated in the previous DM medium (described in Example 1), as determined using a suitable assay for Cyp1A2 activity (e.g. using a P450-GLO™ assay (Promega), as described herein).

In some embodiments, the differentiated liver organoid of the invention or the population of differentiated liver cells has a level of albumin secretion is at least at least 10%, at least 20%, at least 30%, at least 40%, at least 50%, at least 60%, at least 70%, at least 80%, at least 90% or at least 100%, at least 2-fold, at least 5-fold, at least 10-fold or at least 100-fold, compared to the corresponding liver organoid or population of differentiated liver cells differentiated in the previous DM medium (described in Example 1), as determined using a suitable assay for albumin secretion (e.g. a Human Albumin ELISA Kit (Bethyl Laboratories, Inc.), as described herein).

In some embodiments, the differentiated organoid of the invention is a differentiated liver organoid in which one or more (e.g. one, two, three, four or five) of the following cell types is absent: liver macrophages, Kupffer cells, hepatic stellate cells, endothelial cells, smooth muscle cells and fibroblasts.

In some embodiments, the differentiated organoid has a cystic structure with a central lumen. In some embodiments the central lumen is surrounded by an epithelial monolayer.

In some embodiments, the differentiated organoid is a differentiated liver organoid that does not comprise blood vessels or formed bile ducts.

In some embodiments, the differentiated organoid is a differentiated liver organoid in which the hepatocytes are integrated in an epithelial monolayer.

In some embodiments, the differentiated organoid is a differentiated liver organoid with one or more of the following characteristics: (a) it has a cystic structure with a central lumen surrounded by an epithelial monolayer; (b) one or more (e.g. one, two, three, four or five) of the following cell types is absent: liver macrophages, Kupffer cells, hepatic stellate cells, endothelial cells, smooth muscle cells and fibroblasts; (c) it does not comprise blood vessels or formed bile ducts; and (d) the hepatocytes are integrated in an epithelial monolayer.

In some embodiments, the differentiated organoid is a differentiated liver organoid that is spherical.

In some embodiments, the differentiated organoid is a differentiated liver organoid that is 0.02-3 mm in diameter.

In some embodiments, the differentiated organoid is a differentiated liver organoid that exhibits one or more of the following functions: (i) secretory, metabolic and/or anabolic hepatocyte functions and (ii) secretory, metabolic and/or anabolic cholangyocyte functions.

In some embodiments, the differentiated organoid is a differentiated liver organoid that does not exhibit one or more of the following functions: (i) bile production; (ii) bile transport; and (iii) blood filtration.

Also provided is a differentiated organoid or a differentiated population of liver epithelial cells of the invention in a differentiation medium of the invention.

In one embodiment, there is provided an organoid in a differentiation medium, for example as described herein.

In an embodiment, a differentiated organoid is an organoid which is still being cultured using a method of the invention and is therefore in contact with an extracellular matrix. Preferably, a differentiated organoid is embedded in a non-mesenchymal extracellular matrix.

The organoid or population of progenitor cells may be from any mammalian tissue, but is preferably from a human. In some embodiments, it is from a mouse, rabbit, rat, guinea pig or other non-human mammal.

TABLE 3 differences between differentiated liver organoids and primary liver tissue

| | Differentiated organoid | Primary tissue |
|---|---|---|
| Morphology | Cystic structures with central lumen surrounded by epithelial monolayer. No blood vessels or formed bile ducts present. Hepatocytes are integrated in epithelial monolayer. | Solid organ divided into lobes and hexagonal lobules (smallest functional unit). Blood vessels and bile ducts are arranged in regular patterns around hepatocytes. Hepatocytes form stacked 3d structures. |

TABLE 3-continued

| differences between differentiated liver organoids and primary liver tissue | | |
|---|---|---|
| | Differentiated organoid | Primary tissue |
| Size | Organoid: Spheric, 0.02-3 mm diameter | Liver lobule: hexagonal 0.7-2 mm diameter |
| Cell composition | Biliary cells (Cholangyocytes), Hepatocytes, undifferentiated liver stem cells and progenitors | Biliary cells, Hepatocytes, liver macrophages, Kupffer cells, hepatic stellate cells, endothelial cells, smooth muscle cells, fibroblasts |
| Functions | Secretory, metabolic and anabolic hepatocyte and cholangyocyte functions | Secretory, metabolic and anabolic hepatocyte and cholangyocyte functions, bile production, bile transport, blood filtration |

Uses of the Differentiated Organoids

Uses of the organoids described herein and cells derived from the organoids are likewise provided. Where organoids are referred to in this section, these are differentiated organoids in accordance with the invention. It will be understood by the skilled person that may of uses are also applicable to a population of differentiated cells obtained and/or obtainable by the methods of the invention. Such uses of the population of differentiated cells obtained and/or obtainable by the methods of the invention are also provided.

For example, the invention provides the use of a differentiated organoid, or a cell derived from said organoid, in a drug discovery screen; toxicity assay; research of tissue embryology, cell lineages, and differentiation pathways; gene expression studies including recombinant gene expression; research of mechanisms involved in tissue injury and repair; research of inflammatory and infectious diseases; studies of pathogenetic mechanisms; or studies of mechanisms of cell transformation and aetiology of cancer.

The invention also provides an organoid of the invention, or a cell derived from said organoid, for use in medicine.

The invention also provides an organoid of the invention, or a cell derived from said organoid, for use in treating a disorder, condition or disease.

The invention also provides an organoid of the invention, or a cell derived from said organoid for use in regenerative medicine, for example, wherein the use involves transplantation of the organoid or cell into a patient.

The invention provides the use of an organoid of the invention or cells derived from said organoid in drug screening, (drug) target validation, (drug) target discovery, toxicology and toxicology screens, personalized medicine, regenerative medicine and/or as ex vivo cell/organ models, such as disease models.

Cells and organoids cultured according to the media and methods of the invention are thought to faithfully represent the in vivo situation. This is true both for differentiated populations of cells and organoids grown from normal tissue and for differentiated populations of cells and organoids grown from diseased tissue. Therefore, as well as providing normal ex vivo cell/organ models, the organoids of the invention can be used as ex vivo disease models.

Organoids of the invention can also be used for culturing of a pathogen and thus can be used as ex vivo infection models. Examples of pathogens that may be cultured using an organoid of the invention include viruses, bacteria, prions or fungi that cause disease in its animal host. Thus an organoid of the invention can be used as a disease model that represents an infected state. In some embodiments of the invention, the organoids can be used in vaccine development and/or production.

Diseases that can be studied by the organoids of the invention thus include genetic diseases, metabolic diseases, pathogenic diseases, inflammatory diseases etc, for example including, but not limited to: cystic fibrosis, inflammatory bowel disease (such as Crohn's disease), carcinoma, adenoma, adenocarcinoma, colon cancer, diabetes (such as type I or type II), Barrett's esophagus, Gaucher's disease, alpha-1-antitrypsin deficiency, Lesch-Nyhan syndrome, anaemia, Schwachman-Bodian-Diamond syndrome, polycythaemia vera, primary myelofibrosis, glycogen storage disease, familial hypercholestrolaemia, Crigler-Najjar syndrome, hereditary tyrosinanaemia, Pompe disease, progressive familial cholestasis, Hreler syndrome, SCID or leaky SCID, Omenn syndrome, Cartilage-hair hypoplasia, Herpes simplex encephalitis, Scleroderma, Osteogenesis imperfecta, Becker muscular dystrophy, Duchenne muscular dystrophy, Dyskeratosis congenitor etc.

Traditionally, cell lines and more recently iPS cells have been used as ex vivo cell/organ and/or disease models (for example, see Robinton et al. Nature 481, 295, 2012). However, these methods suffer a number of challenges and disadvantages. For example, cell lines cannot be obtained from all patients (only certain biopsies result in successful cell lines) and therefore, cell lines cannot be used in personalised diagnostics and medicine. iPS cells usually require some level of genetic manipulation to reprogramme the cells into specific cell fates. Alternatively, they are subject to culture conditions that affect karotypic integrity and so the time in culture must be kept to a minimum (this is also the case for human embryonic stem cells). This means that iPS cells cannot accurately represent the in vivo situation but instead are an attempt to mimic the behaviour of in vivo cells. Cell lines and iPS cells also suffer from genetic instability.

By contrast, the organoids of the invention provide a genetically stable platform which faithfully represents the in vivo situation. In some embodiments, the organoids of the invention comprise all differentiated cell types that are present in the corresponding in vivo situation. In other embodiments, the organoids of the invention may be further differentiated to provide all differentiated cell types that are present in vivo. Thus the organoids of the invention can be used to gain mechanistic insight into a variety of diseases and therapeutics, to carry out in vitro drug screening, to evaluate potential therapeutics, to identify possible targets (e.g. proteins) for future novel (drug) therapy development and/or to explore gene repair coupled with cell-replacement therapy.

The organoids of the invention can be frozen and thawed and put into culture without losing their genetic integrity or phenotypic characteristics and without loss of proliferative capacity. Thus the organoids can be easily stored and transported. Thus in some embodiments, the invention provides a frozen organoid.

For these reasons the organoids or differentiated populations of cells of the invention can be a tool for drug screening, target validation, target discovery, toxicology and toxicology screens and personalized medicine.

Accordingly, in a further aspect, the invention provides the use of an organoid or cell derived from said organoid according to the invention in a drug discovery screen, toxicity assay or in medicine, such as regenerative medicine. For example, any one of the small intestinal, colon, pancreatic, gastric, liver or prostate organoids may be used in a drug discovery screen, toxicity assay or in medicine, such as regenerative medicine.

Mucosal Vaccines

An additional important use of the organoids is in the development of mucosal vaccinations. Mucosal vaccines are vaccines that are administered via the mucosa. This can be any mucosal surface such as via the nose, mouth, or rectum. They can be administered via an inhaler, a spray or other external aids. This has several clear benefits over injections such as that no medical staff are needed for administering the vaccine, which may be important, for example in developing countries.

In the intestine, M cells (or "microfold cells") are cells found in the follicle-associated epithelium of the aggregated lymphoid nodules of the ileum. They transport organisms and particles from the gut lumen to immune cells across the epithelial barrier, and thus are important in stimulating mucosal immunity. They have the unique ability to take up antigen from the lumen of the small intestine via endocytosis or phagocytosis, and then deliver it via transcytosis to dendritic cells (an antigen presenting cell) and lymphocytes (namely T cells) located in a unique pocket-like structure on their basolateral side.

Organoids can in some cases develop into M cells when stimulated with RANK ligand (e.g. see FIG. 49 of WO2012/169830). Therefore, in some embodiments of the invention, the differentiated cell population comprises M cells. In some embodiments of the invention, an organoid comprises M cells. In some embodiments, there is provided a method for obtaining M cells or an organoid comprising M cells, wherein the method comprises stimulating an organoid with RANK ligand.

The efficiency of mucosal vaccines can be substantially increased when they are targeted to M cells. Therefore, the differentiated cell population or organoid of the invention can be used for testing the ability of M cells to take up pathogens or antigens and to present them to the immune system. Therefore, in some embodiments the invention provides the use of an organoid of the invention in drug screening, for example in vaccine development and/or vaccine production. For example, in some embodiments the organoid may be used for the development or production of vaccines against viral, bacterial, fungal or other parasitic infections, for example (but not limited to) cholera, Respiratory syncytial virus (RSV), Rotavirus and HIV. In a particular embodiment, the invention provides organoids that have been differentiated in a culture medium of the invention comprising RANKL, for use in mucosal vaccine development.

Drug Screening

For preferably high-throughput purposes, said organoid of the invention is cultured in multiwell plates such as, for example, 96 well plates or 384 well plates. Libraries of molecules are used to identify a molecule that affects said organoids. Preferred libraries comprise antibody fragment libraries, peptide phage display libraries, peptide libraries (e.g. LOPAP™, Sigma Aldrich), lipid libraries (BioMol), synthetic compound libraries (e.g. LOP AC™, Sigma Aldrich) or natural compound libraries (Specs, TimTec). Furthermore, genetic libraries can be used that induce or repress the expression of one of more genes in the progeny of the stem cells. These genetic libraries comprise cDNA libraries, antisense libraries, and siRNA or other non-coding RNA libraries. The cells are preferably exposed to multiple concentrations of a test agent for a certain period of time. At the end of the exposure period, the cultures are evaluated. The term "affecting" is used to cover any change in a cell, including, but not limited to, a reduction in, or loss of, proliferation, a morphological change, and cell death. Said organoid of the invention can also be used to identify drugs that specifically target epithelial carcinoma cells, but not said organoid of the invention.

The ability to obtain a useful organoid of the invention in short time periods (days) shows that the organoids would be highly useful for testing individual patient responses to specific drugs and tailoring treatment according to the responsiveness. In some embodiments, wherein the organoid is obtained from a biopsy from a patient, the organoid is cultured for less than 21 days, for example less than 14 days, less than 13 days, less than 12 days, less than 11 days, less than 10 days, less than 9 days, less than 8 days, less than 7 days (etc).

The organoids are also useful for wider drug discovery purposes (e.g. see WO2013/093812 which describes screening for drugs for cystic fibrosis or cholera). Therefore, in some embodiments, the organoids of the invention could be used for screening for cystic fibrosis drugs. However, it will be understood by the skilled person that the organoids of the invention would be widely applicable as drug screening tools for infectious, inflammatory and neoplastic pathologies of the human gastrointestinal tract and other diseases of the gastrointestinal tract and infectious, inflammatory and neoplastic pathologies and other diseases of other tissues described herein including pancreas, liver and prostate. In some embodiments the organoids of the invention could be used for screening for cancer drugs.

In some embodiments, the organoids of the invention can be used to test libraries of chemicals, antibodies, natural product (plant extracts), etc for suitability for use as drugs, cosmetics and/or preventative medicines. For instance, in some embodiments, a cell biopsy from a patient of interest, such as tumour cells from a cancer patient, can be cultured using culture media and methods of the invention and then treated with a chemical compound or a chemical library. It is then possible to determine which compounds effectively modify, kill and/or treat the patient's cells. This allows specific patient responsiveness to a particular drug to be tested thus allowing treatment to be tailored to a specific patient. Thus, this allows a personalized medicine approach.

The added advantage of using the organoids for identifying drugs in this way is that it is also possible to screen normal organoids (organoids derived from healthy tissue) to check which drugs and compounds have minimal effect on healthy tissue. This allows screening for drugs with minimal off-target activity or unwanted side-effects.

Drugs for any number of diseases can be screened in this way. For example the organoids of the invention can be used for screening for drugs for cystic fibrosis, Barrett's esophagus, carcinomas, adenocarcinomas, adenomas, inflammatory bowel disease (such as Crohn's disease), liver disease etc. The testing parameters depend on the disease of interest. For example, when screening for cancer drugs, cancer cell death is usually the ultimate aim. For cystic fibrosis, measuring the expansion of the organoids in response to the drugs and stimuli of CFTR is of interest. In other embodiments, metabolics or gene expression may be evaluated to study the effects of compounds and drugs of the screen on the cells or organoids of interest.

Therefore, the invention provides a method for screening for a therapeutic or prophylactic pharmaceutical drug or cosmetic, wherein the method comprises:

contacting a differentiated cell population or organoid with a candidate molecule (or a library of candidate molecules, evaluating said differentiated cell populations or organoid for any effects (e.g. any change in the cell, such as a reduction in or loss of proliferation, a morphological change and/or cell death) or a change in organoid (e.g. the organoid size or motility);

identifying the candidate molecule that causes said effects as a potential drug or cosmetic; and optionally preparing said candidate molecule as pharmaceutical or cosmetic.

In some embodiments, the invention provides a method for preparing a pharmaceutical or cosmetic, wherein the method comprises:

contacting a differentiated cell population or organoid with a candidate molecule (or a library of candidate molecules, evaluating said differentiated cell populations or organoid for any effects (e.g. any change in the cell, such as a reduction in or loss of proliferation, a morphological change and/or cell death) or a change in organoid (e.g. the organoid size or motility);

identifying the candidate molecule that causes said effects as a potential drug or cosmetic; and optionally preparing said candidate molecule as pharmaceutical or cosmetic.

In some embodiments, computer- or robot-assisted culturing and data collection methods are employed to increase the throughput of the screen. In some embodiments, the organoid is derived from a patient biopsy. In some embodiments, the candidate molecule that causes a desired effect on the cultured differentiated cell population (for example, an organoid) is administered to said patient.

Accordingly, in one aspect, there is provided a method of treating a patient comprising:

(a) obtaining a biopsy from the diseased tissue of interest in the patient;

(b) culturing the biopsy to obtain an organoid;

(c) screening for a suitable drug using a screening method of the invention; and (d) treating said patient with the drug obtained in step (c).

In some embodiments, the drug or cosmetic is used for treating, preventing or ameliorating symptoms of genetic diseases, metabolic diseases, pathogenic diseases, inflammatory diseases etc, for example including, but not limited to: cystic fibrosis, inflammatory bowel disease (such as Crohn's disease), carcinoma, adenoma, adenocarcinoma, colon cancer, diabetes (such as type I or type II), Barrett's esophagus, Gaucher's diseases, alpha-1-antitrypsin deficiency, Lesch-Nyhan syndrome, anaemia, Schwachman-Bodian-Diamond syndrome, polycythemia vera, primary myelofibrosis, glycogen storage disease, familial hypercholestrolaemia, Crigler-Najjar syndrome, hereditary tyrosinanaemia, Pompe disease, progressive familial cholestasis, Hreler syndrome, SCID or leaky SCID, Omenn syndrome, Cartilage-hair hypoplasia, Herpes simplex encephalitis, Scleroderma, Osteogenesis imperfecta, Becker muscular dystrophy, Duchenne muscular dystrophy, Dyskeratosis congenitor etc.

In some embodiments, the invention provides methods for screening for drugs for regenerative medicine, e.g. drugs for regenerating the liver.

Target Discovery

In some embodiments, the organoids of the invention can be used for target discovery. Cells of the organoids originating from healthy or diseased tissue may be used for target identification. The organoids of the invention may be used for discovery of drug targets for cystic fibrosis, inflammatory bowel disease (such as Crohn's disease), carcinoma, adenoma, adenocarcinoma, colon cancer, diabetes (such as type I or type II), Barrett's esophagus Gaucher's disease, alpha-1-antitrypsin deficiency, Lesch-Nyhan syndrome, anaemia, Schwachman-Bodian-Diamond syndrome, polycythaemia vera, primary myelofibrosis, glycogen storage disease, familial hypercholestrolaemia, Crigler-Najjar syndrome, hereditary tyrosinanaemia, Pompe disease, progressive familial cholestasis, Hreler syndrome, SCID or leaky SCID, Omenn syndrome, Cartilage-hair hypoplasia, Herpes simplex encephalitis, Scleroderma, Osteogenesis imperfecta, Becker muscular dystrophy, Duchenne muscular dystrophy, Dyskeratosis congenitor etc. Organoids cultured according to the media and methods of the invention are thought to faithfully represent the in vivo situation. For this reason they can be a tool to find novel (molecular) targets in specific diseases.

To search for a new drug target, a library of compounds (such as siRNA) may be used to transduce the cells and inactivate specific genes. In some embodiments, cells are transduced with siRNA to inhibit the function of a (large) group of genes. Any functional read out of the group of genes or specific cellular function can be used to determine if a target is relevant for the study. A disease-specific read out can be determined using assays well known in the art. For example, cellular proliferation is assayed to test for genes involved in cancer. For example, a Topflash assay as described herein, may be used to detect changes in Wnt activity caused by siRNA inhibition. Where growth reduction or cell death occurs, the corresponding siRNA related genes can be identified by methods known in the art. These genes are possible targets for inhibiting growth of these cells. Upon identification, the specificity of the identified target for the cellular process that was studied will need to be determined by methods well known in the art. Using these methods, new molecules can be identified as possible drug targets for therapy.

Target and Drug Validation Screens

Patient-specific organoids obtained from diseased and/or normal tissue can be used for target validation of molecules identified in high throughput screens. The same goes for the validation of compounds that were identified as possible therapeutic drugs in high throughput screens. The use of primary patient material differentiated in the organoid culture system can be useful to test for false positives, etc. from high throughput drug discovery cell line studies.

In some embodiments, the organoid of the invention can be used for validation of compounds that have been identified as possible drugs or cosmetics in a high-throughput screen.

Toxicity Assay

Said differentiated stem cell population (for example, organoid of the invention), such as liver, intestinal organoids or pancreatic organoids, can further replace the use of cell lines such as Caco-2 cells in toxicity assays of potential novel drugs or of known or novel food supplements.

Toxicology screens work in a similar way to drug screens (as described above) but they test for the toxic effects of drugs and not therapeutic effects. Therefore, in some embodiments, the effects of the candidate compounds are toxic.

Culturing Pathogens

Furthermore, an organoid of the invention can be used for culturing of a pathogen, such as a norovirus which presently lacks a suitable tissue culture or animal model.

Regenerative Medicine and Transplantation

The invention provides the use of organoids in regenerative medicine and/or transplantation. The invention also provides methods of treatment wherein the method comprises transplanting an organoid into an animal or human.

Organoids of the invention, such as liver, intestinal organoids or pancreatic organoids are useful in regenerative medicine, for example in treatment of cirrhosis of the liver, post-radiation and/or post-surgery repair of the intestinal epithelium, in the repair of the intestinal epithelium in patients suffering from inflammatory bowel disease such as Crohn's disease and ulcerative colitis, and in the repair of the intestinal epithelium in patients suffering from short bowel syndrome. Further use is present in the repair of the intestinal epithelium in patients with hereditary diseases of the small intestine/colon. Cultures comprising pancreatic organoids are also useful in regenerative medicine, for example as implants after resection of the pancreas or part thereof and for treatment of diabetes such as diabetes I and diabetes II.

In an alternative embodiment, the organoids or cells isolated from the organoids are reprogrammed into related tissue fates such as, for example, pancreatic cells including pancreatic beta-cells or hepatocytes or ductal cells for the liver. The culturing methods of the present invention will enable to analyse for factors that trans-differentiate the closely related epithelial stem cell to a pancreatic cell, including a pancreatic beta-cell or a hepatocyte.

It will be clear to a skilled person that gene therapy can additionally be used in a method directed at repairing damaged or diseased tissue. Use can, for example, be made of an adenoviral or retroviral gene delivery vehicle to deliver genetic information, like DNA and/or RNA to stem cells. A skilled person can replace or repair particular genes targeted in gene therapy. For example, a normal gene may be inserted into a nonspecific location within the genome to replace a nonfunctional gene. In another example, an abnormal gene sequence can be replaced for a normal gene sequence through homologous recombination. Alternatively, selective reverse mutation can return a gene to its normal function. A further example is altering the regulation (the degree to which a gene is turned on or off) of a particular gene. Preferably, the cells of an organoid or derived from an organoid are ex vivo treated by a gene therapy approach and are subsequently transferred to the mammal, preferably a human being in need of treatment.

Since small biopsies taken from adult donors can be expanded without any apparent limit or genetic harm, the technology may serve to generate transplantable epithelium for regenerative purposes. The fact that organoids can be frozen and thawed and put into culture without losing their 3D structure and integrity and without significant cell death further adds to the applicability of organoids for transplantation purposes. Furthermore, in some embodiments, organoids embedded in, or in contact with, an ECM can be transplanted into a mammal, preferably into a human. In another embodiment, organoids and ECM can be transplanted simultaneously into a mammal, preferably into a human.

The skilled person will understand that an ECM can be used as a 3D scaffold for obtaining tissue-like structures comprising expanded populations of cells or organoids according to the invention. Such structures can then be transplanted into a patient by methods well known in the art. An ECM scaffold can be made synthetically using ECM proteins, such as collagen and/or laminin, or alternatively an ECM scaffold can be obtained by "decellularising" an isolated organ or tissue fragment to leave behind a scaffold consisting of the ECM (for example see Macchiarini et al. The Lancet, Volume 372, Issue 9655, Pages 2023-2030, 2008). In some embodiments, an ECM scaffold can be obtained by decellularising an organ or tissue fragment, wherein optionally said organ or tissue fragment is from the pancreas, liver, intestine, stomach or prostate.

The invention provides an organoid of the invention or cells derived from said organoid for use in transplantation into a mammal, preferably into a human. Also provided is a method of treating a patient in need of a transplant comprising transplanting an organoid of the invention or cells derived from said organoid into said patient, wherein said patient is a mammal, preferably a human. In some embodiments, the organoid is further differentiated before transplantation into said patient.

For example, a small biopsy to be taken from an adult donor and expanded by an expansion method and subsequently differentiated according to the invention. Thus the technology provided herein may serve to generate transplantable epithelium for regenerative purposes.

The invention provides a method of treating an insulin-deficiency disorder such as diabetes in a patient, or a patient having a dysfunctional pancreas, comprising transplanting a pancreatic organoid of the invention or cells from a pancreatic organoid of the invention into the patient. The invention also provides a method for treating a liver disease or condition in a patient, wherein said method comprises transplanting a liver organoid, or cells from a liver organoid of the invention, into a patient.

In some embodiments, the cells or organoid do not express or secrete insulin upon transplantation into the patient but differentiate within the patient such that they secrete insulin. For example, the ability to secrete insulin may not be detectable immediately upon transplantation, but may be present by about one month after transplantation, for example, by 6 weeks, 2 months or 3 months after transplantation.

The patient is preferably a human, but may alternatively be a non-human mammal, such as a cat, dog, horse, cow, pig, sheep, rabbit or mouse.

Thus, included within the scope of the invention are methods of treatment of a human or non-human animal patient through cellular therapy. Such cellular therapy encompasses the application of the stem cells or organoids of the invention to the patient through any appropriate means.

Specifically, such methods of treatment involve the regeneration of damaged tissue. In accordance with the invention, a patient can be treated with allogeneic or autologous stem cells or organoids. "Autologous" cells are cells which originated from the same organism into which they are being re-introduced for cellular therapy, for example in order to permit tissue regeneration. However, the cells have not necessarily been isolated from the same tissue as the tissue they are being introduced into. An autologous cell does not require matching to the patient in order to overcome the problems of rejection. "Allogeneic" cells are cells which originated from an individual which is different from the individual into which the cells are being introduced for cellular therapy, for example in order to permit tissue regeneration, although of the same species. Some degree of patient matching may still be required to prevent the problems of rejection. Thus in some embodiments the transplantation involves autologous cells. In some embodiments, the transplantation involves allogeneic cells.

Generally the cells or organoids of the invention are introduced into the body of the patient by injection or implantation. Generally the cells will be directly injected into the tissue in which they are intended to act. Alternatively, the cells will be injected through the portal vein. A syringe containing cells of the invention and a pharmaceutically acceptable carrier is included within the scope of the invention. A catheter attached to a syringe containing cells of the invention and a pharmaceutically acceptable carrier is included within the scope of the invention.

The skilled person will be able to select an appropriate method and route of administration depending on the material that is being transplanted (i.e. population of cells, single cells in cell suspension, organoids or fragments of organoids) as well as the organ that is being treated.

As discussed above, organoids or cells of the invention can be used in the regeneration of tissue. In order to achieve this function, cells may be injected or implanted directly into the damaged tissue, where they may multiply and eventually differentiate into the required cell type, in accordance with their location in the body. Alternatively, the organoid can be injected or implanted directly into the damaged tissue. Tissues that are susceptible to treatment include all damaged tissues, particularly including those which may have been damaged by disease, injury, trauma, an autoimmune reaction, or by a viral or bacterial infection. In some embodiments of the invention, the cells or organoids of the invention are used to regenerate the colon, small intestine, pancreas, oesophagus or gastric system.

For example, in one embodiment, the cells or organoids of the invention are injected into a patient using a Hamilton syringe.

The skilled person will be aware what the appropriate dosage of cells or organoids of the invention will be for a particular condition to be treated.

In one embodiment the organoids or cells of the invention, either in solution, in microspheres or in microparticles of a variety of compositions, will be administered into the artery irrigating the tissue or the part of the damaged organ in need of regeneration. Generally such administration will be performed using a catheter. The catheter may be one of the large variety of balloon catheters used for angioplasty and/or cell delivery or a catheter designed for the specific purpose of delivering the cells to a particular local of the body. For certain uses, the cells or organoids may be encapsulated into microspheres made of a number of different biodegradable compounds, and with a diameter of about 15 μm. This method may allow intravascularly administered cells or organoids to remain at the site of damage, and not to go through the capillary network and into the systemic circulation in the first passage. The retention at the arterial side of the capillary network may also facilitate their translocation into the extravascular space.

In another embodiment, the organoids or cells may be retrograde injected into the vascular tree, either through a vein to deliver them to the whole body or locally into the particular vein that drains into the tissue or body part to which the cells or organoids are directed. For this embodiment many of the preparations described above may be used.

In another embodiment, the cells or organoids of the invention may be implanted into the damaged tissue adhered to a biocompatible implant. Within this embodiment, the cells may be adhered to the biocompatible implant in vitro, prior to implantation into the patient. As will be clear to a person skilled in the art, any one of a number of adherents may be used to adhere the cells to the implant, prior to implantation. By way of example only, such adherents may include fibrin, one or more members of the integrin family, one or more members of the cadherin family, one or more members of the selectin family, one or more cell adhesion molecules (CAMs), one or more of the immunoglobulin family and one or more artificial adherents. This list is provided by way of illustration only, and is not intended to be limiting. It will be clear to a person skilled in the art, that any combination of one or more adherents may be used.

In another embodiment, the organoids or cells of the invention may be embedded in a matrix, prior to implantation of the matrix into the patient. Generally, the matrix will be implanted into the damaged tissue of the patient. Examples of matrices include collagen based matrices, fibrin based matrices, laminin based matrices, fibronectin based matrices and artificial matrices. This list is provided by way of illustration only, and is not intended to be limiting.

In a further embodiment, the organoids or cells of the invention may be implanted or injected into the patient together with a matrix forming component. This may allow the cells to form a matrix following injection or implantation, ensuring that the cells or organoids remain at the appropriate location within the patient. Examples of matrix forming components include fibrin glue liquid alkyl, cyanoacrylate monomers, plasticizers, polysaccharides such as dextran, ethylene oxide-containing oligomers, block copolymers such as poloxamer and PLURONICS®, non-ionic surfactants such as Tween and Triton '8', and artificial matrix forming components. This list is provided by way of illustration only, and is not intended to be limiting. It will be clear to a person skilled in the art, that any combination of one or more matrix forming components may be used.

In a further embodiment, the organoids or cells of the invention may be contained within a microsphere. Within this embodiment, the cells may be encapsulated within the centre of the microsphere. Also within this embodiment, the cells may be embedded into the matrix material of the microsphere. The matrix material may include any suitable biodegradable polymer, including but not limited to alginates, Poly ethylene glycol (PLGA), and polyurethanes. This list is provided by way of example only, and is not intended to be limiting.

In a further embodiment, the cells or organoids of the invention may be adhered to a medical device intended for implantation. Examples of such medical devices include stents, pins, stitches, splits, pacemakers, prosthetic joints, artificial skin, and rods. This list is provided by way of illustration only, and is not intended to be limiting. It will be clear to a person skilled in the art, that the cells may be adhered to the medical device by a variety of methods. For example, the cells or organoids may be adhered to the medical device using fibrin, one or more members of the integrin family, one or more members of the cadherin family, one or more members of the selectin family, one or more cell adhesion molecules (CAMs), one or more of the immunoglobulin family and one or more artificial adherents. This list is provided by way of illustration only, and is not intended to be limiting. It will be clear to a person skilled in the art, that any combination of one or more adherents may be used.

The organoid or population of epithelial stem cells or population of differentiated cells obtained using a method of the invention have a variety of uses. For example, the invention provides the use of the organoid or population of epithelial stem cells/differentiated cells as described herein in a drug discovery screen; toxicity assay; research of embryology, cell lineages, and differentiation pathways; gene expression studies including recombinant gene expression; research of mechanisms involved in injury and repair; research of inflammatory and infectious diseases; studies of pathogenetic mechanisms; or studies of mechanisms of cell transformation and aetiology of cancer.

In one aspect, the invention provides the use of an organoid or population of epithelial stem cells/differentiated cells as described herein in a drug discovery screen, toxicity assay or in regenerative medicine. Similarly, the invention provides the use of the progeny of organoids of the invention for these uses.

Toxicity assays may be in vitro assays using an organoid or part thereof or a cell derived from an organoid. Such progeny and organoids are easy to culture and more closely resemble primary epithelial cells than, for example, epithelial cell lines such as Caco-2 (ATCC HTB-37), I-407 (ATCC CCL6), and XBF (ATCC CRL 8808) which are currently used in toxicity assays. It is anticipated that toxicity results obtained with organoids more closely resemble results obtained in patients. A cell-based toxicity test is used for determining organ specific cytotoxicity. Compounds that are tested in said test comprise cancer chemopreventive agents, environmental chemicals, food supplements, and potential toxicants. The cells are exposed to multiple concentrations of a test agent for certain period of time. The concentration ranges for test agents in the assay are determined in a preliminary assay using an exposure of five days and log dilutions from the highest soluble concentration. At the end of the exposure period, the cultures are evaluated for inhibition of growth. Data are analysed to determine the concentration that inhibited end point by 50 percent (TC50).

For example, according to this aspect of the invention, a candidate compound may be contacted with cell or organoid as described herein, and any change to the cells or in activity of the cells may be monitored.

For high-throughput purposes, said organoids are cultured in multiwell plates such as, for example, 96 well plates or 384 well plates. Libraries of molecules are used to identify a molecule that affects said organoids. Preferred libraries comprise antibody fragment libraries, peptide phage display libraries, peptide libraries (e.g. LOPAP™, Sigma Aldrich), lipid libraries (BioMol), synthetic compound libraries (e.g. LOP AC™, Sigma Aldrich) or natural compound libraries (Specs, TimTec). Furthermore, genetic libraries can be used that induce or repress the expression of one of more genes in the progeny of the adenoma cells. These genetic libraries comprise cDNA libraries, antisense libraries, and siRNA or other non-coding RNA libraries. The cells are preferably exposed to multiple concentrations of a test agent for certain period of time. At the end of the exposure period, the cultures are evaluated. The term "affecting" is used to cover any change in a cell, including, but not limited to, a reduction in, or loss of, proliferation, a morphological change, and cell death. Said organoids can also be used to identify drugs that specifically target epithelial carcinoma cells, but not said organoids.

Organoids according to the invention can further replace the use of cell lines such as Caco-2 cells in drug discovery screens and in toxicity assays of potential novel drugs or known drugs or known or novel food supplements.

Furthermore, such organoids can be used for culturing of a pathogen.

The invention further provides a differentiated organoid of the invention or a population of differentiated cells of the invention for use in therapy. Also provided is a differentiation organoid of the invention or a cell derived from said organoid for use in treating a disease or condition as described herein.

Similarly, there is provided a method of treating a disease or condition as described herein comprising administering one or more organoids of the invention, or cell derived from said organoid.

The inventors have also demonstrated successful transplantation of organoids into immunodeficient mice (see example 7 of WO 2012/014076), with transplanted liver organoid-derived cells generating both cholangyocytes and hepatocytes in vivo. Therefore, in one embodiment the invention provides organoids or organoid-derived cells of the invention for transplanting into human or animals.

An advantage of the organoids of the invention is that they can be frozen and later be defrosted without loss of function. This enables cell banking, easy storage and rapid availability for acute use. This could be useful for example, in the preparation of an "off-the-shelf" product, for example, in the case of liver, that might be used for the treatment of acute liver toxicity. Organoids can also be grown from cells or tissue fragments taken as small biopsies from live donors minimising any ethical objections to the treatment. The donor may even be from the patient that is to be treated, which could reduce any negative side-effects associated with transplantation of foreign cells and organs and reduce the need for immunosuppressive drugs.

In some embodiments, the invention also provides a pharmaceutical formulation comprising the components of the differentiation medium described herein and a pharmaceutically acceptable diluent and/or excipient. For example, there is provided a pharmaceutical formulation comprising one or more Wnt inhibitors (e.g. IWP-2 and/or iCRT3), one or more GSK-3 inhibitors (e.g. CHIR99021), one or more AP-1 stimulants (e.g. carbachol), one or more receptor tyrosine kinase ligands (e.g. EGF, HGF and/or FGF19) one or more TGF-beta inhibitors (e.g. A83-01), one or more Notch inhibitors (e.g. DAPT), one or more glucocorticoids (e.g. dexamethasone) and a pharmaceutically acceptable diluent and/or excipient. In a preferred embodiment, the pharmaceutical formulation does not comprise a basal medium. In some embodiments, the pharmaceutical formulation does not comprise an extracellular matrix. It is envisaged that such formulations may be suitable for promoting differentiation of stem cells in vivo, e.g. for regenerative therapy. Such formulations may be administered in situ (e.g. at the site of tissue damage) or systemically. Alternatively, the formulations may be formulated so that it is suitable for administration by any administration routes known in the art, for example intravenous, subcutaneous, intramuscular administration, mucosal, intradermal, intracutaneous, oral, and ocular. A pharmaceutical formulation may be thus be in any form suitable for such administration, e.g. a tablet, infusion fluid, capsule, syrup, etc.

Accordingly, included within the scope of the invention are methods of treatment of a human or non-human animal patient through cellular therapy. The term "animal" here denotes all mammalian animals. The patient may be at any stage of development, including embryonic and foetal stages. For example, the patient may be an adult, or the therapy may be for pediatric use (e.g. newborn, child or adolescent). Such cellular therapy encompasses the administration of cells or organoids generated according to the invention to a patient through any appropriate means. Specifically, such methods of treatment involve the regeneration of damaged tissue. The term "administration" as used herein refers to well recognized forms of administration, such as intravenous or injection, as well as to administration by transplantation, for example transplantation by surgery, grafting or transplantation of tissue engineered cell populations derived from cells or organoids according to the present invention. In the case of cells, systemic administration to an individual may be possible, for example, by infusion into the superior mesenteric artery, the celiac artery, the subclavian vein via the thoracic duct, infusion into the heart via the superior vena cava, or infusion into the peritoneal cavity with subsequent migration of cells via subdiaphragmatic lymphatics, or directly into liver sites via infusion into the hepatic arterial blood supply or into the portal vein.

In some embodiments, between $10^4$ and $10^{13}$ cells per 100 kg person are administered per infusion. Preferably, between about 1-5×$10^4$ and 1-5×$10^7$ cells may be infused intravenously per 100 kg person. More preferably, between about 1×$10^4$ and 10×$10^6$ cells may be infused intravenously per 100 kg person. In some embodiments, a single administration of cells or organoids is provided. In other embodiments, multiple administrations are used. Multiple administrations can be provided over an initial treatment regime, for example, of 3-7 consecutive days, and then repeated at other times.

It is also possible to obtain an organoid from one single cell expressing Lgr5 as explained herein. This single cell may have been modified by introduction of a nucleic acid construct as defined herein, for example, to correct a genetic deficiency or mutation. It would also be possible to specifically ablate expression, as desired, for example, using siRNA. Potential polypeptides to be expressed could be any of those that are deficient in metabolic diseases, including, for example, a polypeptide deficiency in metabolic liver disease, such as AAT (alpha antitrypsin). For elucidating physiology, we might also express or inactivate genes implicated in the Wnt, EGF, FGF, BMP or notch pathway. Also, for screening of drug toxicity, the expression or inactivation of genes responsible for liver drug metabolism (for example, genes in the CYP family) would be of high interest. This is particularly relevant when the cells of the invention are liver cells.

In one embodiment, the expanded epithelial stem cells may be reprogrammed into related tissue fates such as, for example, liver cells including a hepatocyte and a cholangiocyte cell. The culturing methods of the present invention will enable to analyse for factors that trans-differentiate the closely related epithelial stem cell to a liver cell, including a hepatocyte and a cholangiocyte cell.

It will be clear to a skilled person that gene therapy can additionally be used in a method directed at repairing damaged or diseased tissue. Use can, for example, be made of an adenoviral or retroviral gene delivery vehicle to deliver genetic information, like DNA and/or RNA to stem cells. A skilled person can replace or repair particular genes targeted in gene therapy. For example, a normal gene may be inserted into a nonspecific location within the genome to replace a non-functional gene. In another example, an abnormal gene sequence can be replaced for a normal gene sequence through homologous recombination. Alternatively, selective reverse mutation can return a gene to its normal function. A further example is altering the regulation (the degree to which a gene is turned on or off) of a particular gene. Preferably, the stem cells are ex vivo treated by a gene therapy approach and are subsequently transferred to the mammal, preferably a human being in need of treatment. For example, organoid-derived cells may be genetically modified in culture before transplantation into patients.

Thus, in some embodiments, the organoid or population of epithelial stem cells is for use in medicine, e.g. for treating a disorder, condition or disease and/or for use in regenerative medicine.

In one preferred embodiment, for example, if an organoid is to be used for regenerative medicine, the method may start from epithelial cells or from a tissue fragment in which the cells or tissue fragment are autologous or allogeneic. Some degree of patient matching may still be required to prevent the problems of rejection. Techniques for minimising tissue rejection will be known to those of skill in the art.

In embodiments in which the organoids and/or cells are transplanted into a patient, it can be advantageous to administer the cells in a scaffold. Accordingly, there is provided a scaffold comprising one or more organoids of the invention or cells derived from said organoids. A scaffold provides a two-dimensional or three dimensional network. Suitable synthetic materials for such a scaffold comprise polymers selected from porous solids, nanofibers, and hydrogels such as, for example, peptides including self-assembling peptides, hydrogels composed of polyethylene glycol phosphate, polyethylene glycol fumarate, polyacrylamide, polyhydroxyethyl methacrylate, polycellulose acetate, and/or co-polymers thereof (see, for example, Saha et al., 2007. Curr Opin Chem Biol. 11 (4): 381-387; Saha et al., 2008. Biophysical Journal 95:4426-4438; Little et al., 2008. Chem. Rev 108, 1787-1796). As is known to a skilled person, the mechanical properties such as, for example, the elasticity of the scaffold influences proliferation, differentiation and migration of stem cells. A preferred scaffold comprises biodegradable (co)polymers that are replaced by natural occurring components after transplantation in a subject, for example to promote tissue regeneration and/or wound healing. It is furthermore preferred that said scaffold does not substantially induce an immunogenic response after transplantation in a subject. Said scaffold is supplemented with natural, semi-synthetic or synthetic ligands, which provide the signals that are required for proliferation and/or differentiation, and/or migration of stem cells. In a preferred embodiment, said ligands comprise defined amino acid fragments. Examples of said synthetic polymers comprise PLURONIC® F127 block copolymer surfactant (BASF), and ETHISORB® (Johnson and Johnson). In some embodiments the cells are cultured in the scaffold. In other embodiments, they are cultured and then added to the scaffold.

The uses of the present invention may use a single organoid or they may use more than one organoid, for example, 2, 3, 4, 5, 10, 15, 20, 30, 50, 100, 200 or more organoids. Advantageously, the methods of the present invention allow a great number of organoids and epithelial stem cells to be generated in a short period of time, because they result in exponential growth, thereby ensuring that sufficient cells are available for use in the application of interest. Wherever there is reference herein to a "method of treatment" or "method for treatment", for example involving the organoids or cells obtained from the organoids of the invention, this also refers equally to organoids or cells "for use in treatment" and to organoids or cells "for use in the manufacture of a medicament".

Artificial Organs

In some embodiments, there is provided the use of a differentiated organoid or cells derived from the differentiated organoid in an artificial organ. The artificial organ may be transplanted in vivo by methods explained elsewhere. Alternatively, the artificial organ may be ex vivo. In some embodiments, the ex vivo artificial organ may be connected to a patient, e.g. via the blood supply. For instance, an artificial organ comprising a differentiated organoid may be used as part of a dialysis machine. Thus a differentiated organoid can be used to support a patient with diseased or injured epithelial tissue.

The uses of the invention are exemplified below in relation to the liver and pancreas.

Uses of Liver Organoids and Populations of Cells

The liver organoid or population of differentiated liver cells obtained using a method of the invention have a variety of uses. For example, the invention provides the use of the liver organoid or population of differentiated liver cells as described herein in a drug discovery screen; toxicity assay; research of liver embryology, liver cell lineages, and differentiation pathways; gene expression studies including recombinant gene expression; research of mechanisms involved in liver injury and repair; research of inflammatory and infectious diseases of the liver; studies of pathogenetic mechanisms; or studies of mechanisms of liver cell transformation and aetiology of liver cancer.

In one aspect, the invention provides the use of a liver organoid or population of liver differentiated cells as described herein in a drug discovery screen, toxicity assay or in regenerative medicine. Similarly, the invention provides the use of the progeny of liver organoids of the invention for these uses.

Toxicity assays may be in vitro assays using a liver organoid or part thereof or a cell derived from a liver organoid. Such progeny and liver organoids are easy to culture and more closely resemble primary epithelial cells than, for example, epithelial cell lines such as Caco-2 (ATCC HTB-37), I-407 (ATCC CCL6), and XBF (ATCC CRL 8808) which are currently used in toxicity assays. It is anticipated that toxicity results obtained with liver organoids more closely resemble results obtained in patients. A cell-based toxicity test is used for determining organ specific cytotoxicity. Compounds that are tested in said test comprise cancer chemopreventive agents, environmental chemicals, food supplements, and potential toxicants. The cells are exposed to multiple concentrations of a test agent for certain period of time. The concentration ranges for test agents in the assay are determined in a preliminary assay using an exposure of five days and log dilutions from the highest soluble concentration. At the end of the exposure period, the cultures are evaluated for inhibition of growth. Data are analysed to determine the concentration that inhibited end point by 50 percent (TC50).

For example, induction of cytochrome P450 enzymes in liver hepatocytes is a key factor that determines the efficacy and toxicity of drugs. In particular, induction of P450s is an important mechanism of troublesome drug-drug interactions, and it is also an important factor that limits drug efficacy and governs drug toxicity. Cytochrome P450 induction assays have been difficult to develop, because they require intact normal human hepatocytes. These cells have proven intractable to production in numbers sufficient to sustain mass production of high throughput assays.

The invention provides the use of liver organoids or populations of liver cells according to the invention for use in medicine or diagnostics. In one embodiment, the invention provides the use of liver organoids or populations of liver cells according to the invention for use in regenerative medicine, for example in post-radiation and/or post-surgery repair of the liver epithelium, in the repair of the epithelium in patients suffering from chronic or acute liver failure or disease. Liver diseases for which the liver organoid or cells derived from said organoid may be used include, but are not limited to Hepatocellular Carcinoma, Alagille Syndrome, Alpha-1-Antitrypsin Deficiency, Autoimmune Hepatitis, Biliary Atresia, Chronic Hepatitis, Cancer of the Liver, Cirrhosis, Liver Cysts, Fatty Liver Disease, Galactosemia Gilbert's Syndrome, Primary Biliary Cirrhosis, Hepatitis A, Hepatitis B, Hepatitis C, Primary Sclerosing Cholangitis, Reye's Syndrome, Sarcoidosis, Tyrosinemia, Type I Glycogen Storage Disease, Wilson's Disease, Neonatal Hepatitis, Non-alcoholic SteatoHepatitis, Porphyria, and Hemochromatosis.

In some embodiments, the liver organoids or populations of liver cells are used for therapy of genetic conditions. Genetic conditions that lead to liver failure could benefit from cell-based therapy in the form of partial or full cell replacement using cells cultured according to the media and/or methods of the invention. A non-limiting list of genetic conditions that lead to liver failure and which are treatable by the present invention includes: Progressive familial intrahepatic cholestasis, Glycogen storage disease type III, Tyrosinemia, Deoxyguanosine kinase deficiency, Pyruvate carboxylase deficiency, Congenital dyserythropoietic anemia, Polycystic Liver Disease Polycystic Kidney Disease, Alpha-1 antitrypsine deficiency, Ureum cycle defects, Organic acidemiea, lysosomal storage diseases, and Fatty Acid Oxydation Disorders. Other conditions that may also benefit from cell-based therapy include Wilson's Disease and Hereditary Amyloidosis (FAP).

Other non-hepatocyte related causes of liver failure that would require a full liver transplant to reach full therapeutic effect, may still benefit from some temporary restoration of function using cell-based therapy using cells cultured according to the media and/or methods of the invention. A non-limiting list of examples of such conditions which may be treatable by the organoids and/or populations of cells of the present invention includes: Primary Biliary Cirrhosis, Primary Sclerosing Cholangitis, Aglagille syndrome, Homozygous Familial hypercholesterolemia, Hepatitis B with cirrhosis, Hepatitis C with cirrhosis, Budd-Chiari syndrome, Primary hyperoxaluria, Autoimmune Hepatitis, and Alcoholic liver disease.

The liver organoids of the invention may be used in a method of treating a hereditary disease that involves malfunctioning hepatocytes. Such diseases may be early onset or late onset. Early onset disease include metabolite related organ failure (e.g. alpha-1-antitrypsin deficiency), glycogen storage diseases (e.g. GSD II, Pompe's disease), tyrosinemia, mild DGUOK, CDA type I, Ureum cycle defects (e.g. OTC deficiency), organic academia and fatty acid oxidation disorders. Late onset diseases include primary hyperoxaluria, familial hypercholesterolemia, Wilson's disease, Hereditary Amyloidosis and Polycystic liver disease. Partial or full replacement with healthy hepatocytes arising from liver organoids of the invention may be used to restore liver function or to postpone liver failure. Accordingly, the invention provides the use of the liver organoids and/or populations of liver cells for restoration of liver function or to postpone liver failure.

The liver organoids of the invention may be used in a method of treating chronic liver failure arising due to hereditary metabolic disease or as a result of hepatocyte infection. Treatment of a hereditary metabolic disease may involve administration of genetically modified autologous liver organoids of the invention. Treatment of hepatocyte infections may involve administration of allogeneic liver organoids of the invention. In some embodiments, the liver organoids are administered over a period of 2-3 months.

The liver organoids of the invention may be used to treat acute liver failure, for example, as a result of liver intoxication which may result from use of paracetamol, medication or alcohol. In some embodiments, the therapy to restore liver function will comprise injecting hepatocyte suspension from frozen, ready to use allogenic hepatocytes obtained from organoids of the invention. The ability to freeze suitable organoids means that the organoids can be available for immediate delivery and so it is not necessary to wait for a blood transfusion.

In the case of replacement or correction of deficient liver function, it may be possible to construct a cell-matrix structure from one or more liver organoids generated according to the present invention. Thus in some embodiments, there is provided a cell-matrix structure derived from a liver organoid and suitable for use in therapy as described herein.

It is thought that only about 10% of hepatic cell mass is necessary for adequate function. This makes implantation of organoid unit compositions into children especially preferable to whole organ transplantation, due to the relatively limited availability of donors and smaller size of juvenile organs. For example, an 8-month-old child has a normal liver that weighs approximately 250 g. That child would therefore need about 25 g of tissue. An adult liver weighsapproximately 1500 g; therefore, the required implant would only be about 1.5% of the adult liver. In some embodiments, therefore, the treatment described in this section is for children. In other embodiments it is for adults.

In some embodiments, the transplantation step involves a scaffold, such as a polymer scaffold. When organoid units according to the invention are implanted, optionally attached to a polymer scaffold, proliferation in the new host will occur, and the resulting hepatic cell mass replaces the deficient host function. The inventors have shown that it is possible to generate mature hepatocytes from adult liver stem cells or liver tissue fragments comprising stem cells that are suitable for transplantation into non-human animals or humans. Using the differentiation culture medium according to the invention, the inventors have shown that hepatoblasts can be differentiated in vivo to mature hepatocytes suitable for transplantation purposes. Hence, the inventors provide a new source of hepatocytes for liver regeneration, replacement or correction of deficient liver function.

In some embodiments it is desirable to repopulate/replace 10-20% of a patient's liver with healthy hepatocytes arising from a liver organoid of the invention.

In some embodiments, the invention provides the liver organoids or populations of liver cells obtained from the differentiation media for use in therapy. Such organoids and populations of cells are useful for treating ductal cell disease. For example, such organoids and populations of cells may be used to treat diseases of the ductal tree, for example diseases caused by a mutations in Jagged1 (JAG1), for example Alagille syndrome, or mutations in the transporter ABCB4, for example Low Phospholipid associated Cholelithiasis. Other non-hereditary cholangiopathies such as Primary Biliary Cirrhosis, Primary sclerosis cholangitis and *Caroli* disease may also be treated using the liver organoids or expanded populations of liver cells of the invention. Such diseases may benefit from expanding duct-cells in culture. Other diseases that could be treated with organoids or expanded populations of liver cells of the invention include hereditary liver diseases where bilirubin metabolism is affected. Such diseases would benefit from hepatocyte transplants. Examples of known hereditary defects in bilirubin metabolism are Crigler-Najjar syndrome (mutation in UGT1A1 gene), Dubin-Johnson syndrome (mutation in cMOAT), and Rotor syndrome (mutations in SLCO1B1 and SLCO1B3).

Thus, in some embodiments, the liver organoid or population of liver epithelial cells is for use in treating a liver disorder, condition or disease or for use in regenerative medicine.

Uses of Pancreas Organoids and Populations of Cells

Methods for culturing pancreatic cells are described in WO 2010/090513. It is envisaged that the differentiation media and methods of the invention will enhance the differentiation of epithelial stem cells obtained from the pancreas.

Thus, in some embodiments, the invention provides a pancreatic organoid or cell obtained from the pancreatic organoid for use in medicine, e.g. for use in treating a pancreatic disorder, condition or disease or for use in regenerative medicine.

The invention further provides a pancreatic organoid or cell obtained from the pancreatic organoids for use in the treatment of diabetes (e.g. diabetes type I or type II), pancreatitis, pancreatic cancer or cystic fibrosis, whereby the treating optionally comprises transplantation of the organoid or cells obtained from the pancreatic organoid into a patient in need thereof. In some embodiments, the transplanted cells are insulin secreting cells. In other embodiments, the cells are progenitor cells that mature further after transplantation into insulin secreting cells.

Abbreviations

β-TrCP: β-transducin-repeat-containing protein
GSK-3: glycogen synthase kinase 3
LGR: leucine-rich repeat-containing G protein-coupled receptor
LRP: low-density lipoprotein receptor-related protein
PP1: protein phosphatase 1
PP2A: protein phosphatase 2A
PP2C: protein phosphatase 2C

Definitions

As used herein, the verb "to comprise" and its conjugations is used in its non-limiting sense to mean that items following the word are included, but items not specifically mentioned are not excluded. In addition the verb "to consist" may be replaced, if necessary, by "to consist essentially of" meaning that a product as defined herein may comprise additional component(s) than the ones specifically identified, said additional component(s) not altering the unique characteristic of the invention. In addition a method as defined herein may comprise additional step(s) than the ones specifically identified, said additional step(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

As used herein, the term "about" or "approximately" means that the value presented can be varied by +/−10%. The value can also be read as the exact value and so the term "about" can be omitted. For example, the term "about 100" encompasses 90-110 and also 100.

All patent and literature references cited in the present specification are hereby incorporated by reference in their entirety.

The following examples are offered for illustrative purposes only, and are not intended to limit the scope of the present invention in any way.

DESCRIPTION OF THE DRAWINGS

FIG. 1A: Improved method for expanding and differentiating a population of liver epithelial stem cells. The liver epithelial stem cells are grown for five days in EM+BMP7 medium (EM+BMP7 comprises Gibco Advanced DMEM/F12 as a basal medium, to which is added: N2, B27 without retinoic acid, EGF, HGF, TGF-beta inhibitor, nicotinamide, Rspondin, forskolin, gastrin, N-acetylcysteine, FGF10 and BMP7). After this pre-treatment, the organoid culture is disrupted, split and transferred to DM+ medium. The previous method for expanding and differentiating a population of liver epithelial stem cells involved liver epithelial stem cells being grown for five days in EM+BMP7 medium and then, without disruption or splitting, transferred to DM medium. FIG. 1B: Components of DM and DM+ media. DM+ medium comprises Gibco Advanced DMEM/F12 as a basal medium, to which is added: 10 mM HEPES, 1×B27-VitA, 1×N2, 1.25 mM N-Acetylcysteine, 50 ng/ml hEGF, 10 nM gastrin, 25 ng/ml HGF, 0.5 μM A83.01, 25 ng/ml BMP7, 100 ng/ml FGF19, 10 μM DAPT, 3 μM dexamethasone, 3 μM IWP-2, 3 μM Chir, 50 M iCRT3 and 100 μM carbachol. DM medium comprises Gibco Advanced DMEM/F12 as a basal medium, to which is added: 10 mM HEPES, 1×B27-VitA, 1×N2, 1.25 mM N-Acetylcysteine, 50 ng/ml hEGF, 10 nM gastrin, 25 ng/ml HGF, 0.5 μM A83.01, 25 ng/ml BMP7, 100 ng/ml FGF19, 10 μM DAPT and 3 μM dexamethasone.

FIG. 2A List of factors that did not show positive effects on hepatocyte differentiation. FIG. 2B-2F qRT-PCR analysis of organoids in expansion medium (EM), after 11 days in differentiation medium (DM) or after 11 days in DM plus a modification. FIG. 2B The addition of the AP-1 stimulant carbachol to DM medium improves the expression of albumin and Cyp3A4, which are hepatocyte cell markers. FIG. 2C The addition of Wnt to DM medium decreases the expression of albumin and Cyp3A4. FIG. 2D The addition of an inhibitor of Wnt secretion, IWP-2, to DM medium enhances the expression of albumin and Cyp3A4. FIG. 2E The addition of CHIR99021 (a GSK3beta inhibitor that strongly increases Wnt signalling by interfering with the activity of the beta-catenin destruction complex) to DM medium increases the expression of albumin and Cyp3A4. The addition of CHIR99021 and iCRT3 (a small molecule that is capable of blocking the binding of beta-catenin to TCF4, and so capable of blocking Wnt signalling downstream of the beta-catenin destruction complex) leads to a significant increase in albumin and Cyp3A4 expression, while reducing the expression of CK19 (a biliary cell marker). FIG. 2F Disrupting and splitting the organoid culture after five days of EM+BMP7 pre-treatment and changing directly to DM medium improves both albumin and Cyp3A4 levels. FIG. 2G Human liver organoids after 11 days differentiation under standard conditions (standard DM) or using the new splitting technique (split DM). Splitting of the organoid culture results in decreased organoid size, which may contribute to enhanced differentiation. The complete removal of all expansion medium growth factors during the splitting procedure may also promote differentiation.

FIG. 4A Immunofluorescence staining for albumin after 11 days of differentiation following the standard (DM) or improved (DM+) protocol. Three views of exemplary organoids obtained using each protocol are provided: albumin, DAPI and brightfield. The DM+ protocol significantly increases the number of cell that differentiate to the hepatocyte fate. FIG. 4B Measurement of Cyp3A4 activity (P450-GLO™ assay) of HepG2, primary hepatocytes and human liver organoids in expansion medium (EM), standard differentiation medium (DM) or following the improved differentiation procedure (DM+) at day 11. The Cyp3A4 activity of cells differentiated using the DM+ protocol is at the level of primary hepatocytes and surpasses the levels achieved by HepG2 cells or the old DM condition by far. FIG. 4C Albumin secretion by HepG2, primary hepatocytes and human liver organoids in EM, DM or following the improved differentiation procedure (DM+) at day 11. FIG. 4D Conversion of Midazolam (a drug) to 1-OH-Midazolam by HepG2, human liver organoids in EM, DM or following the improved differentiation procedure (DM+) at day 11. Improved drug processing activity is seen in cells differentiated using the DM+ protocol. FIGS. 4B-4D Each point represents an independent donor.

EXAMPLES

Example 1

Figures 1A, 1B:
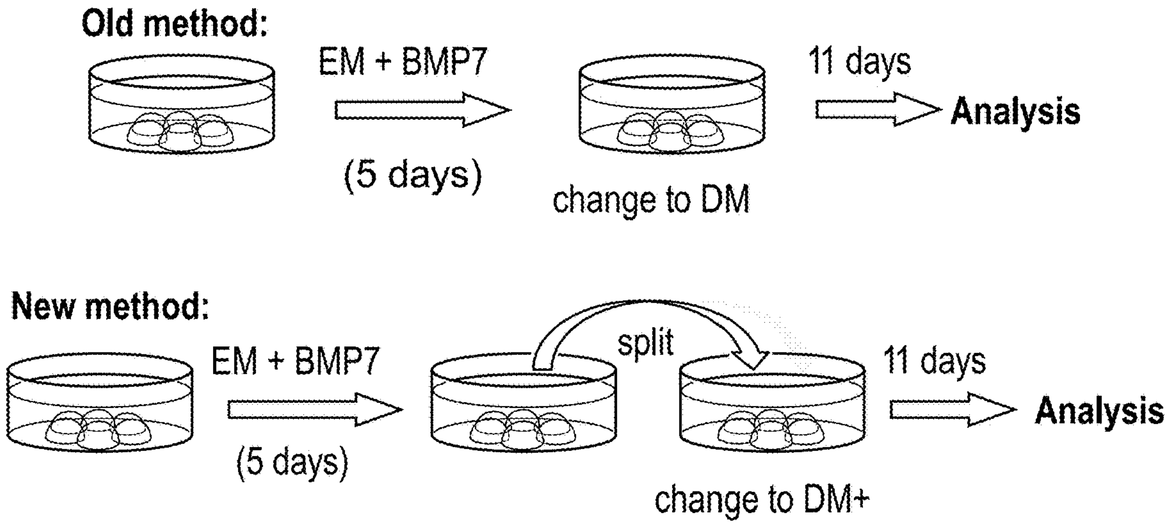
FIGS. 1A-1B.

We significantly improved our ability to differentiate human liver organoids from bipotential stem cells to the hepatocyte state. Building on the previously established (old) differentiation protocol (DM) we developed a new improved procedure (DM+) that combines the treatment with 4 additional differentiation factors with a changed splitting protocol for the differentiation process (FIG. 1A and FIG. 1B). The components in the previous and improved differentiation media are summarised in the tables below. The DM+ protocol results in increased expression of all tested hepatocyte markers and reduces biliary fate commitment during the differentiation process. Most notably, DM+ leads to a significant improvement in the expression and activity of cytochromes (e.g. Cyp3A4 at the level of primary hepatocytes), which are the key enzymes of drug metabolism in hepatocytes. Thus, DM+ is a major step forward to adapt human liver organoids for commercial applications such as toxicology assays and drug development.

Figures 2A, 2B:
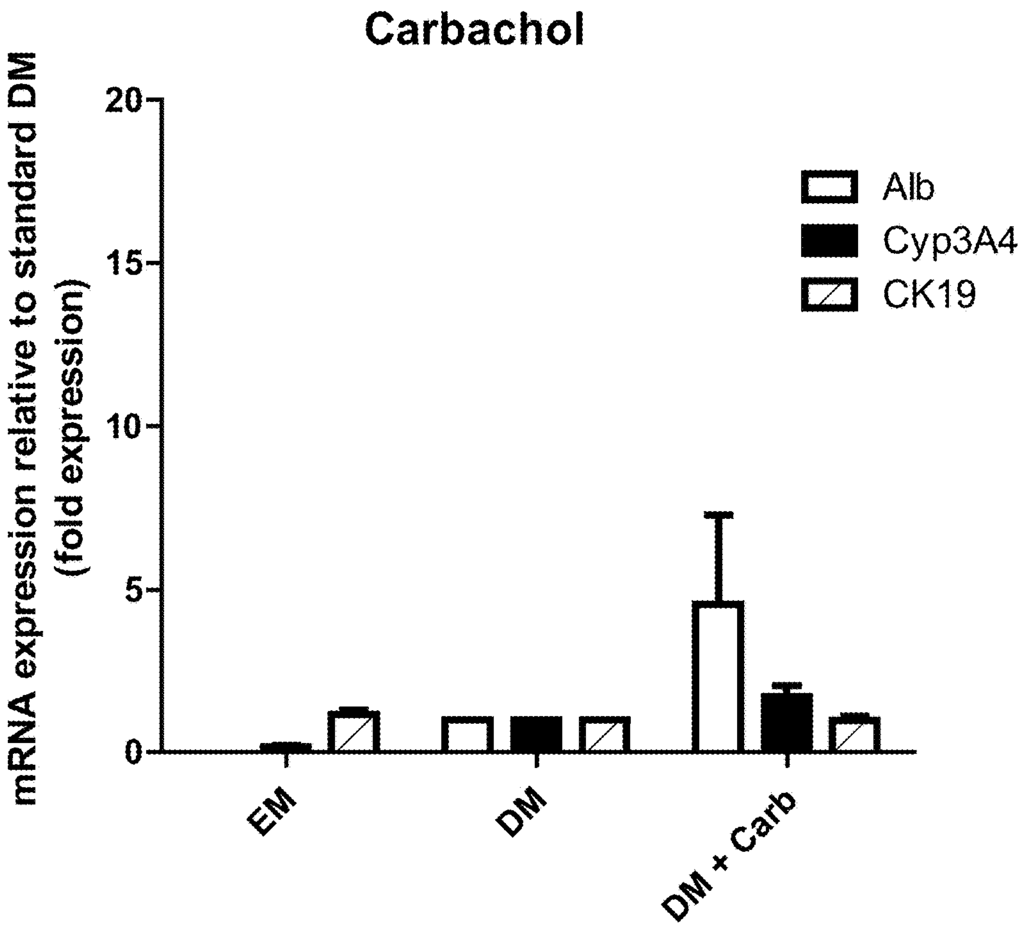
FIGS. 2A-2G.
Figure 2C:
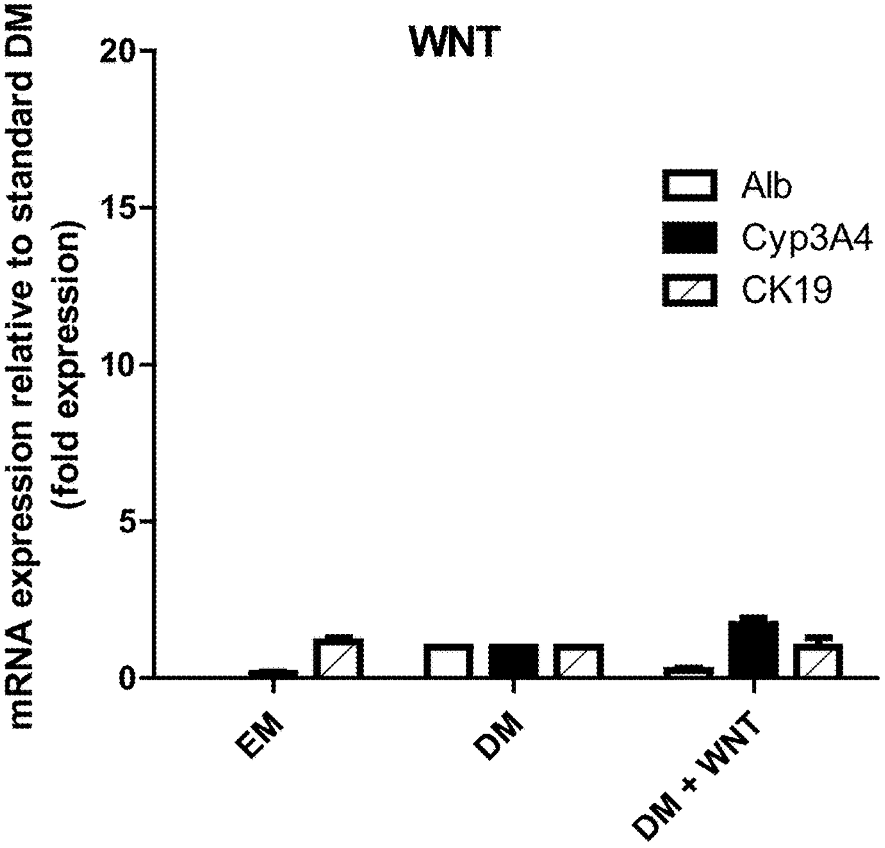
Figure 2D:
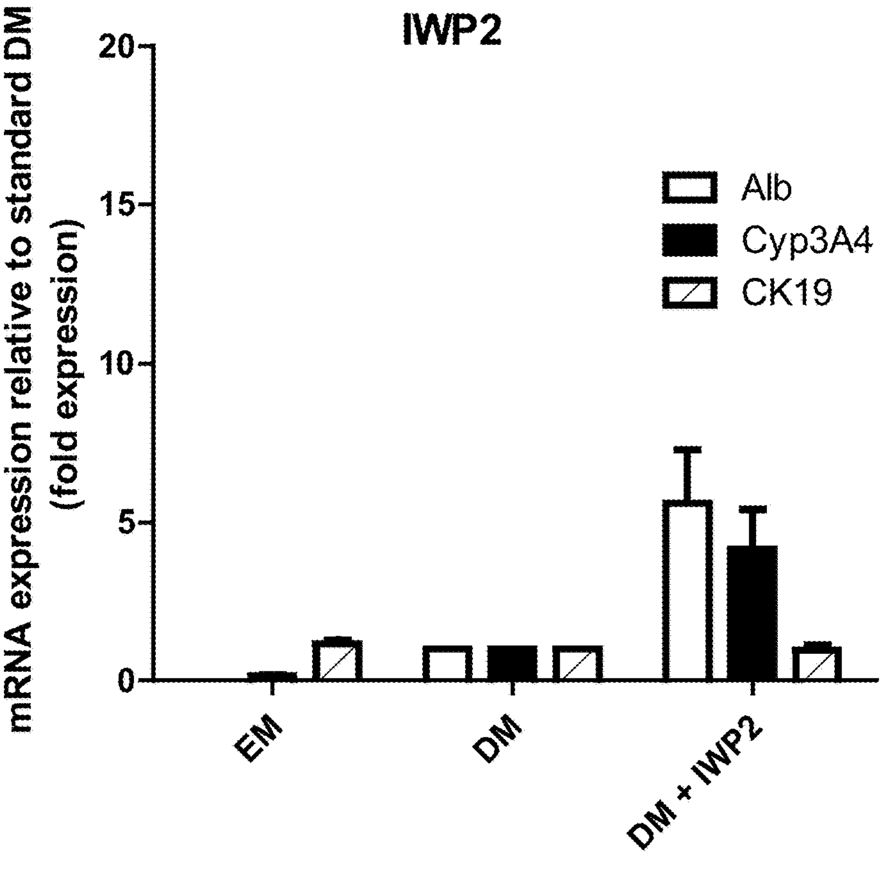
Figure 2E:
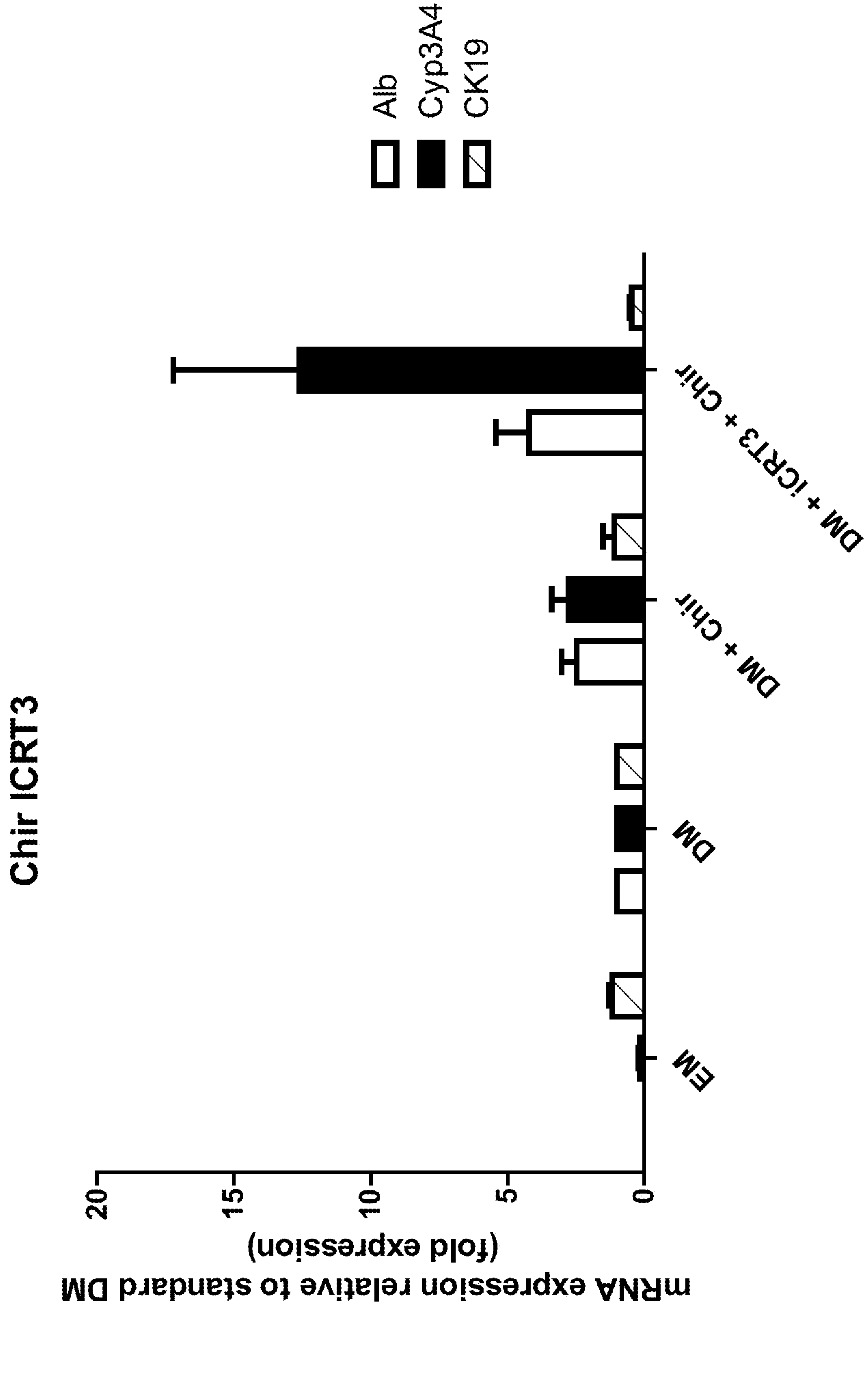
Figure 2F:
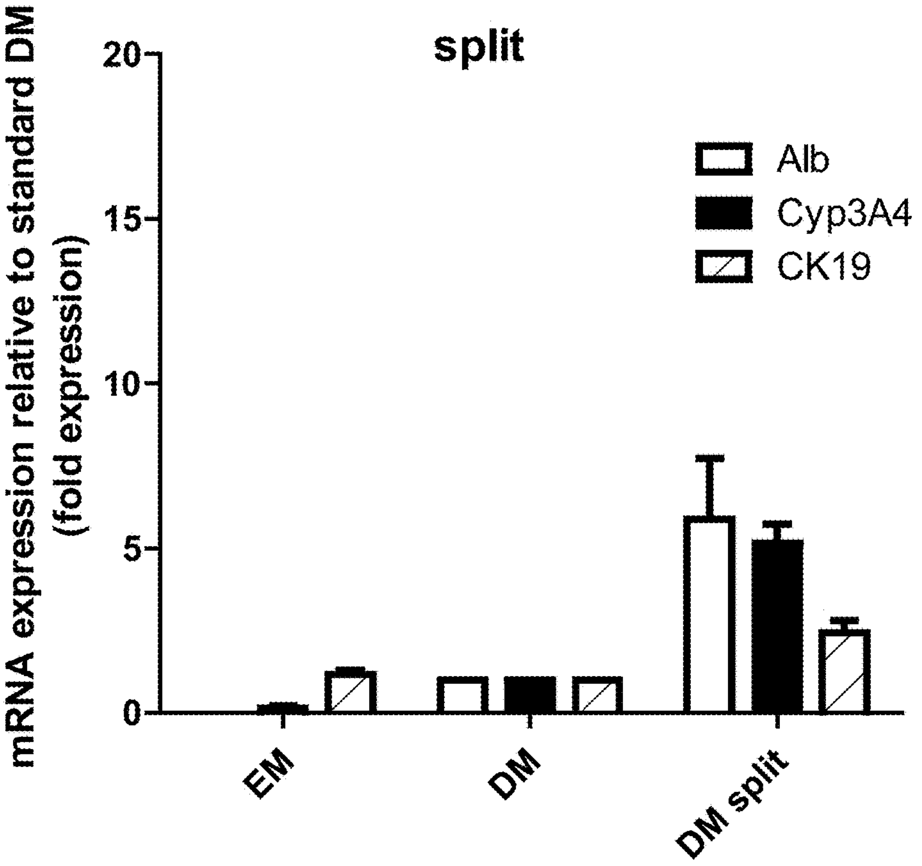
Figure 2G:
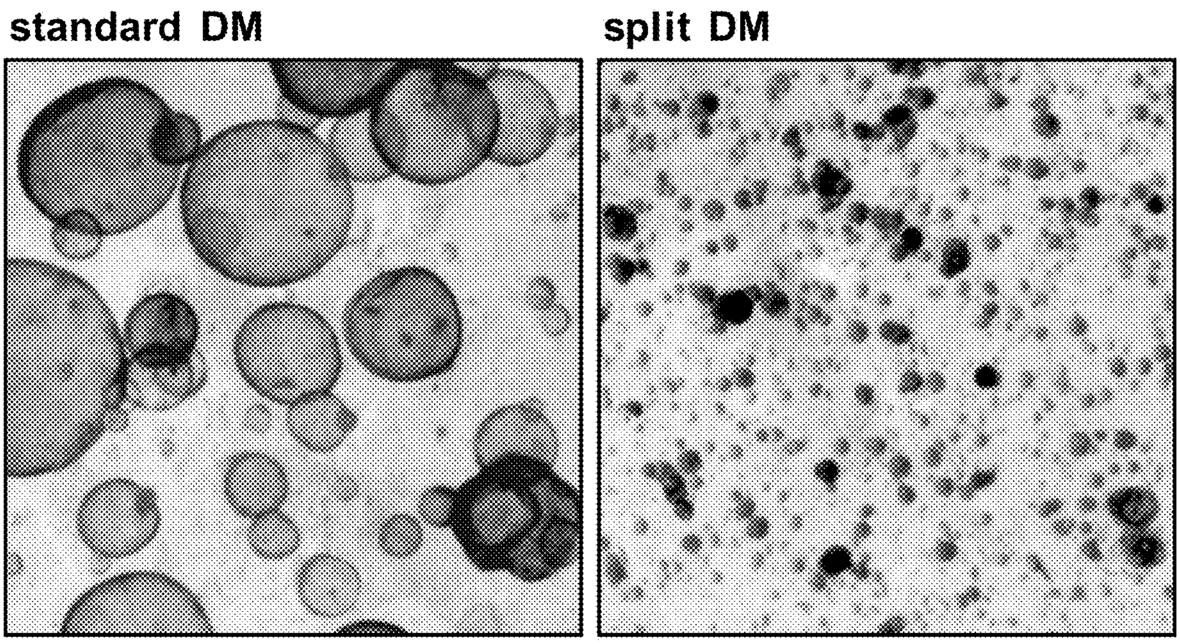

The human liver organoids were obtained from human liver stem cells cultured in an expansion medium (e.g. see table below) in accordance with methods previously described in WO2012/014076, WO2012/168930 and WO2015/173425. To improve human liver organoid differentiation, we tested a plethora of different factors with potentially beneficial effects. However, the majority of these did not contribute to differentiation improvement (see FIG. 2A). As human liver organoids have reduced expression of components of the AP-1 complex in comparison to primary hepatocytes (data not shown), we tested the AP-1 stimulant carbachol in addition to our standard differentiation medium and saw slight improvements in expression of Albumin and Cyp3A4 (FIG. 2B). Addition of WNT to the differentiation medium had the opposite effect and decreased expression of Albumin (FIG. 2C). Consequently, we tested an inhibitor of WNT secretion (IWP-2) to block endogenous WNT signaling and observed an increase in both Albumin and Cyp3A4 expression. In the same set of experiments we also tested CHIR, an inhibitor of GSK3beta, which strongly increases WNT signaling by interfering with activity of the beta-catenin destruction complex. Contrary to expectations, addition of CHIR99021 did not block differentiation (as stimulation by WNT did), but we observed a small increase in both Albumin and Cyp3A4 expression. This led us to the conclusion, that CHIR99021 stimulation has dual effects with a differentiation promoting and a differentiation inhibiting component. From the previous experiment we knew that WNT signaling would be the inhibitory component. Therefore, we looked into the possibility to combine CHIR99021 stimulation with a block of WNT signaling downstream of the destruction complex to cancel out the inhibitory component. Indeed, combination of CHIR99021 with iCRT3, a small molecule capable of blocking the binding of beta-catenin to TCF4, led to a significant increase in Albumin and Cyp3A4 expression, while reducing the expression of the biliary marker CK19 (FIG. 2E). In addition to medium additives we also looked into technical optimization of the differentiation process. We found that disrupting and splitting the organoid culture after 5 days of EM+BMP7 pretreatment and changing directly to differentiation medium improved both Albumin and Cyp3A4 levels (FIG. 2F). This is likely to be a combined effect of decreased organoid size (FIG. 2G) and the complete removal of all expansion medium growth factors during the splitting procedure.

Figure 3A:
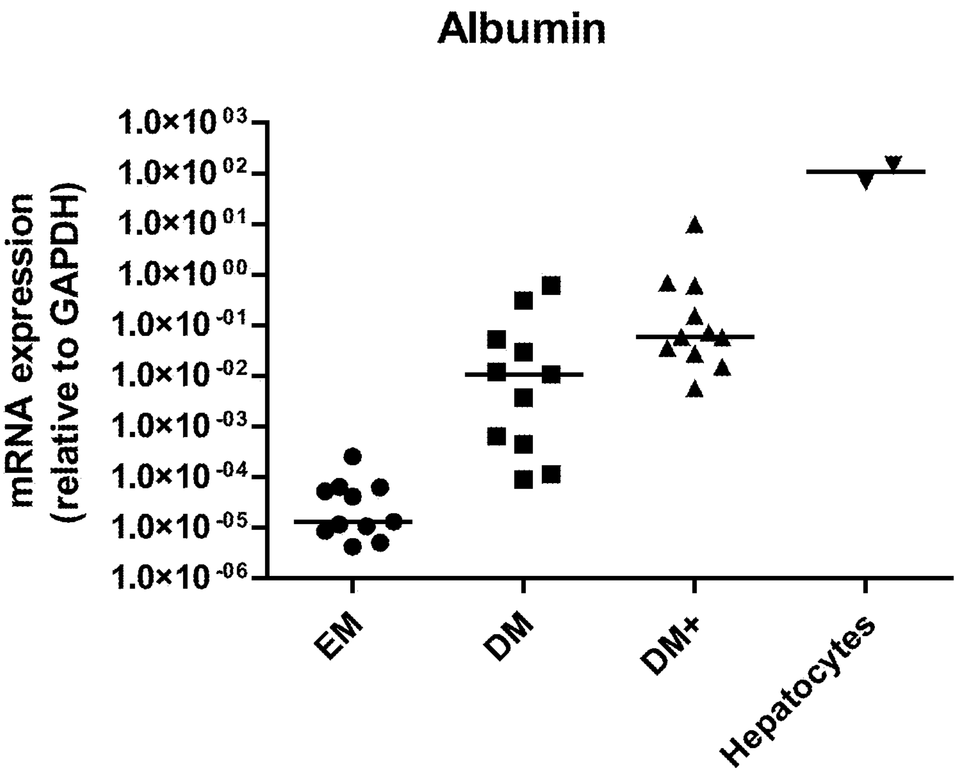
FIGS. 3A-3H. qRT-PCT analysis of primary hepatocytes or organoids in expansion medium (EM) or after 11 days differentiation following either the standard differentiation protocol (DM) or the improved procedure (DM+), which combines the DM+ medium with the splitting procedure. Expression levels of indicated genes are depicted relative to GAPDH. Each point represents an independent experiment. DM+ medium combined with the splitting procedure leads to a substantial improvement in expression of hepatocyte markers such as FIG. 3A albumin, FIG. 3B HNFa, FIG. 3C serpinA1 and FIG. 3D ASPGR. Most notably, however, the expression of cytochromes, such as FIG. 3E Cyp1A2 and FIG. 3F Cyp3A4 is strongly increased. The expression of Cyp3A4 is on average 50× higher in comparison to the DM protocol (without splitting) and reaches the level of primary hepatocytes. The expression of biliary markers, such as FIG. 3G CK7 and FIG. 3H CK19, is clearly reduced in the new DM+ protocol, which corroborates the increased differentiation to the hepatocyte lineage.
Figure 3B:
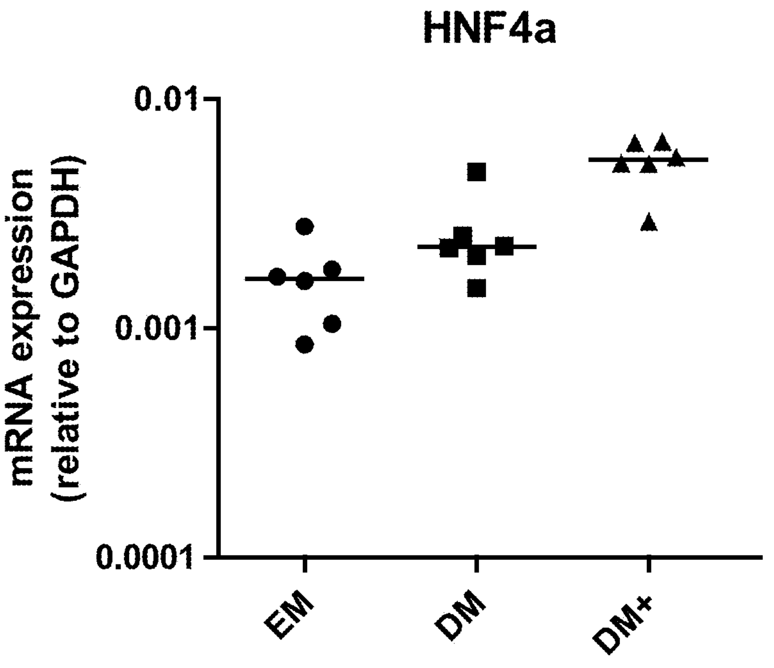
Figure 3C:
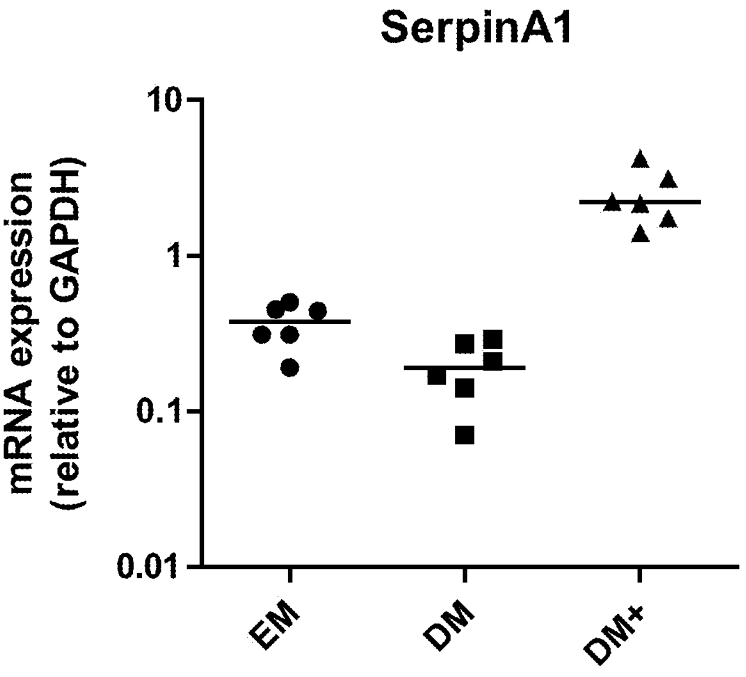
Figure 3D:
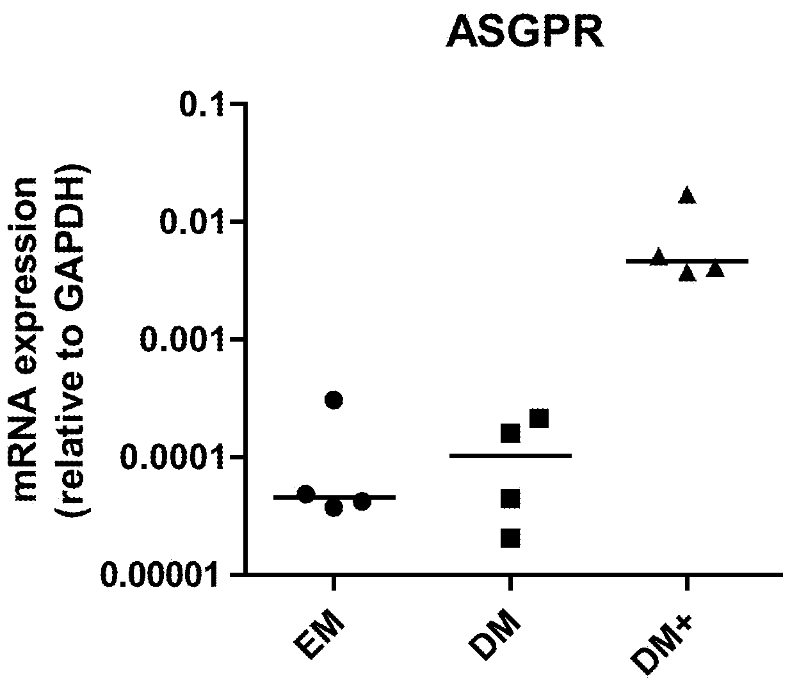
Figure 3E:
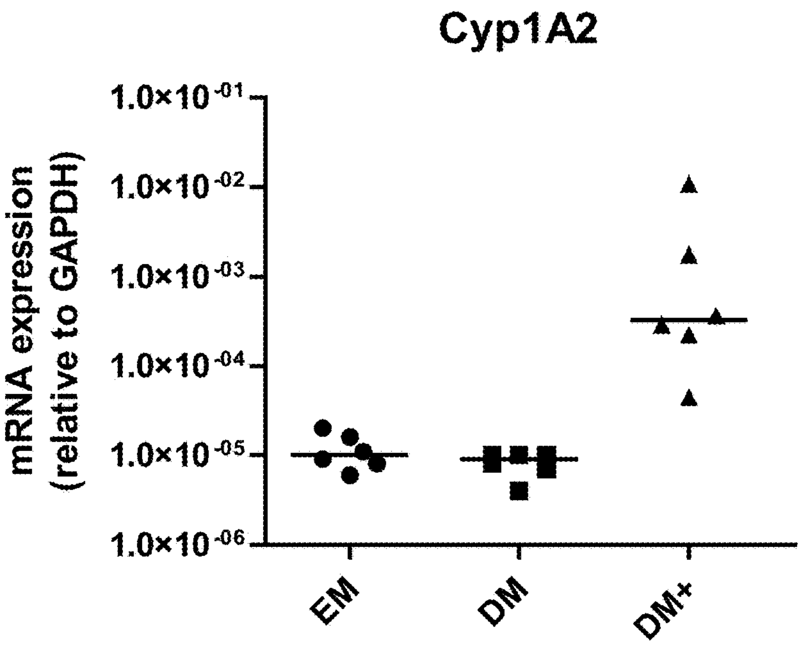
Figure 3F:
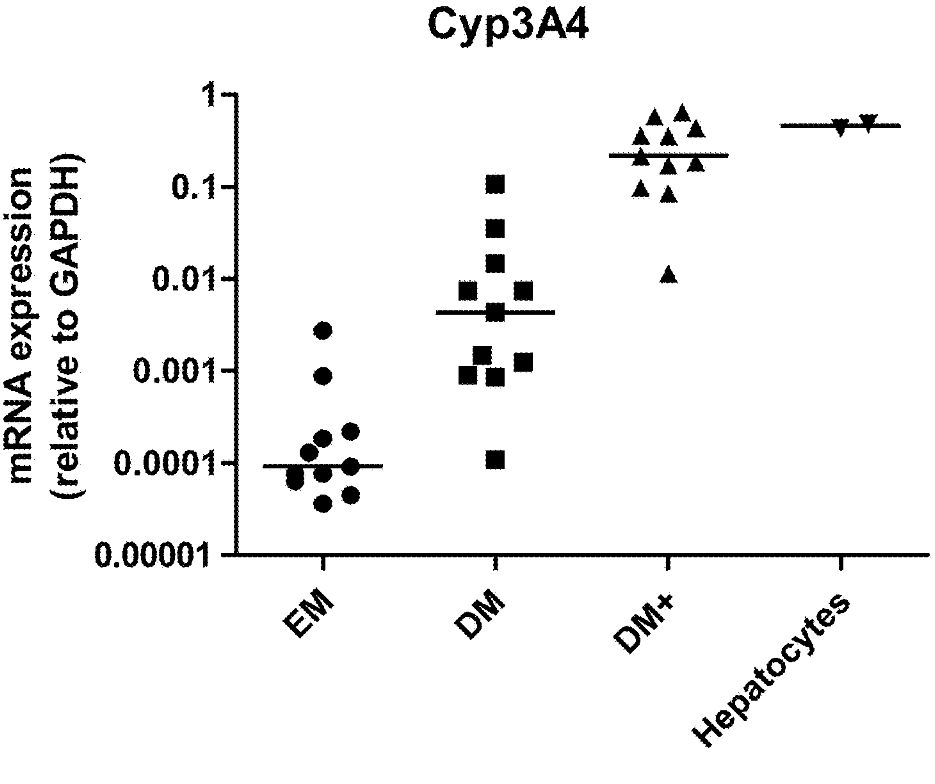
Figure 3G:
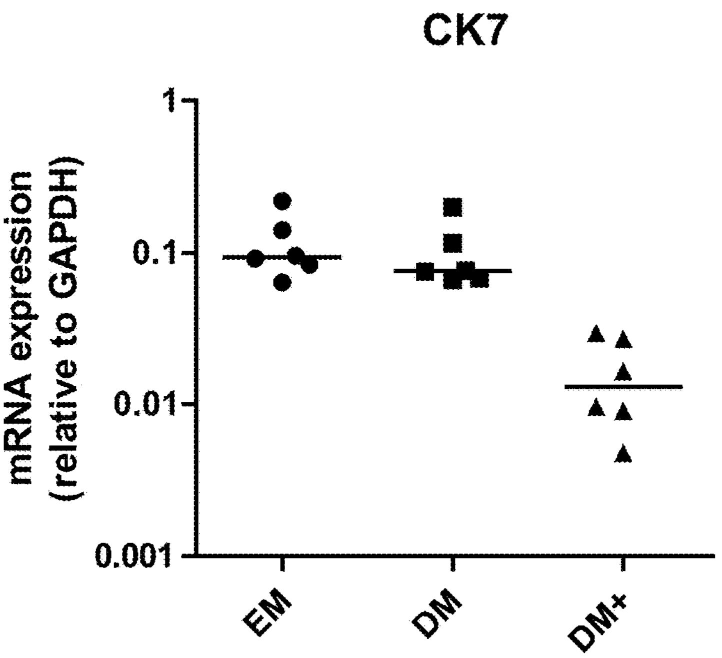
Figure 3H:
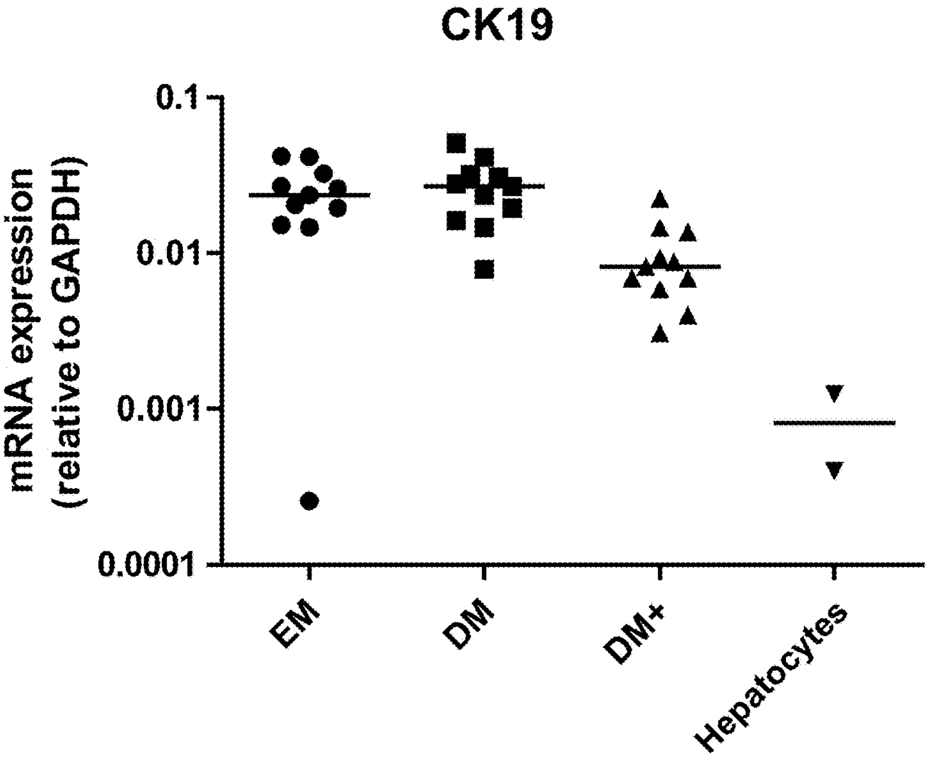

We tested, whether the differentiation improvement by Carbachol, IWP-2, CHIR99021+iCRT3 and the new splitting procedure were additive and indeed this turned out to be the case. Thus, we defined our new differentiation protocol DM+ as a combination of the above (FIG. 1A and FIG. 1B). DM+ leads to an even higher improvement in expression of hepatocyte markers such as Albumin (FIG. 3A), HNFa (FIG. 3B), SerpinA1 (FIG. 3C) and ASGPR (FIG. 3D). Most notably, however, the expression of Cytochromes such as Cyp1A2 and Cyp3A4 is strongly increased (FIG. 3E and FIG. 3F). The expression of Cyp3A4 is on average 50× higher in comparison to the old DM protocol and reaches the level of primary hepatocytes. The expression of biliary marker such as CK7 and CK19 is clearly reduced in the new DM+ protocol (FIG. 3G and FIG. 3H), which corroborates the increased differentiation to the hepatocyte lineage.

Figure 4A:
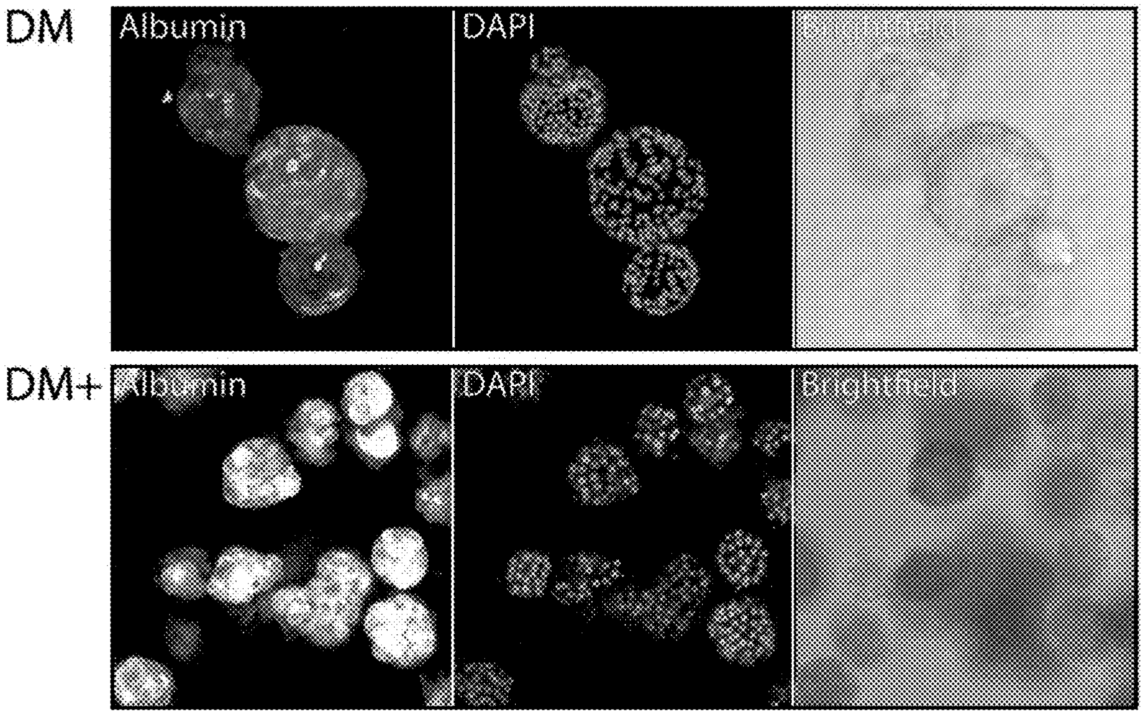
FIGS. 4A-4D. Improved hepatocyte functions in human liver organoids after DM+ differentiation.
Figure 4B:
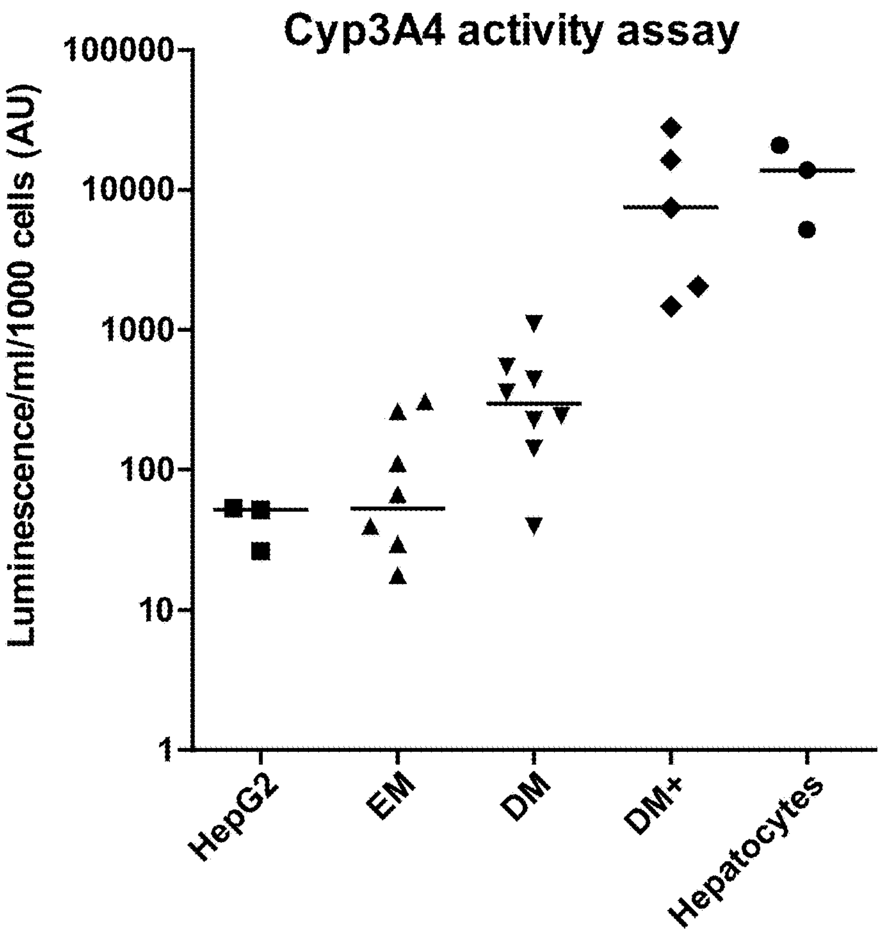
Figure 4D:
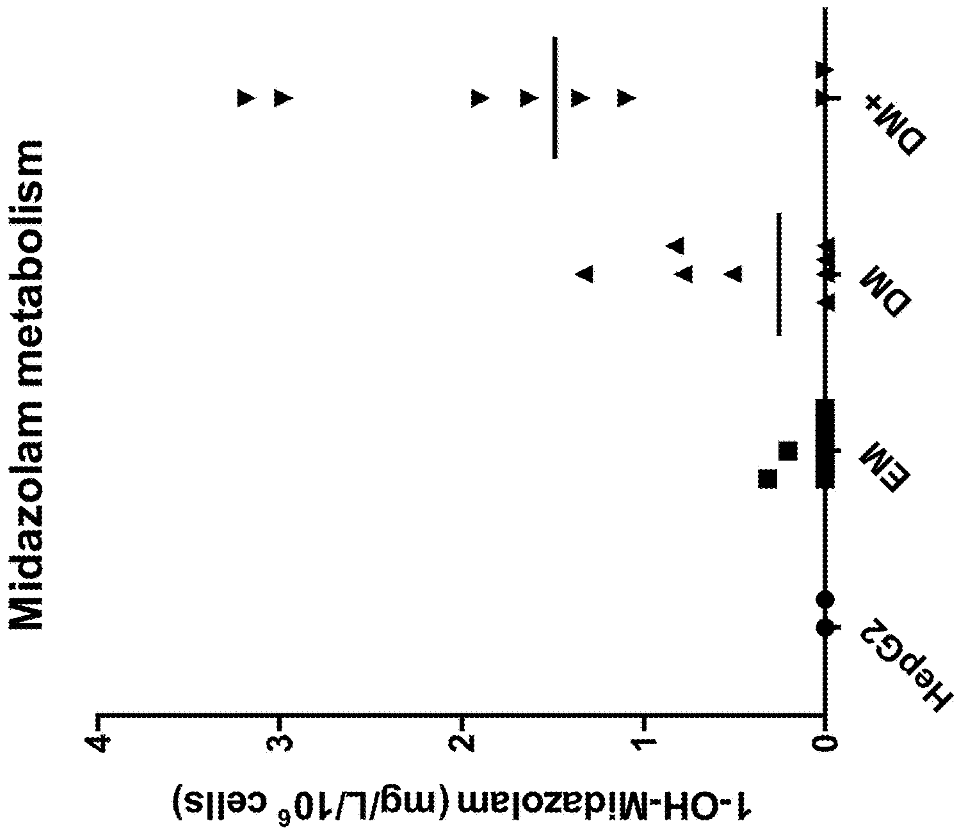
Figure 4C:
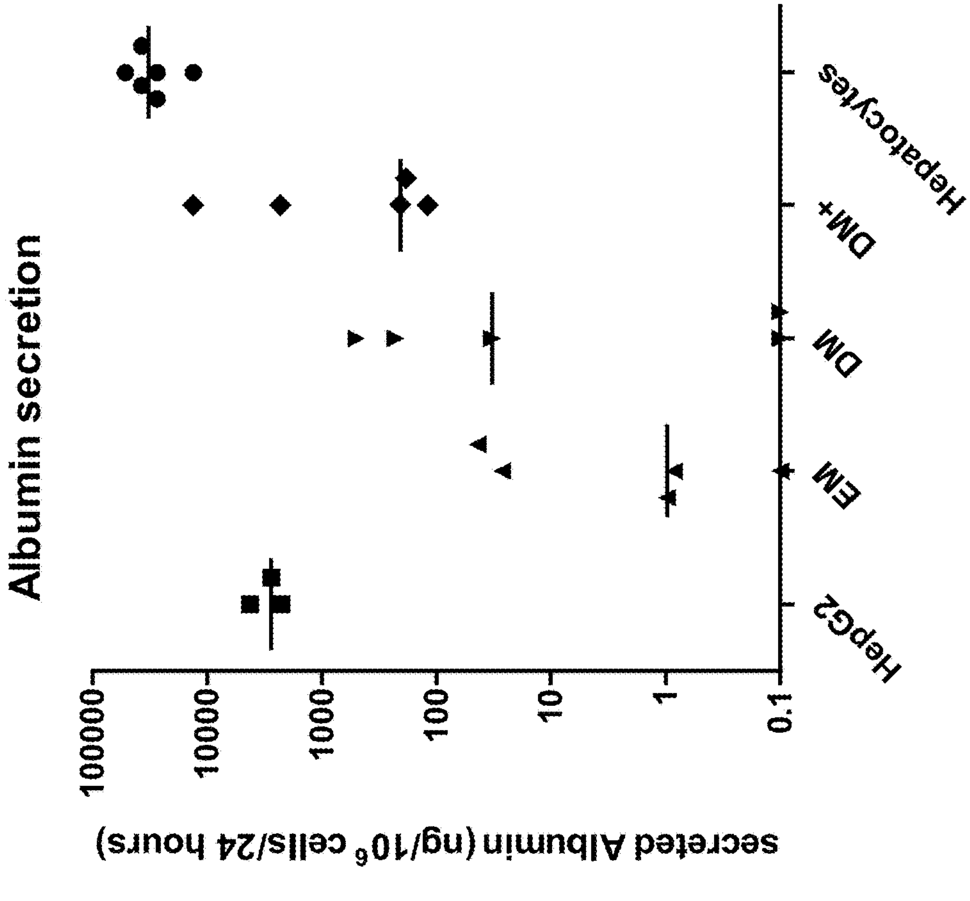

Generally, the DM+ protocol significantly increases the number of cells that differentiate to the hepatocyte fate (FIG. 4A). This is also evident in functional assays such as a Cyp3A4 activity assay and Albumin secretion (FIG. 4B and FIG. 4C). Cyp3A4 activity of cells differentiated according to the DM+ protocol is at the level of primary hepatocytes and surpasses levels achieved by HepG2 cells or the old DM condition by far. This is also reflected by improved drug processing activity, such as the processing of Midazolam to 1-OH-Midazolam (FIG. 4D). In summary, DM+ is an important step forward in differentiation of human liver organoids to the hepatocyte fate and improves their performance in various drug metabolism and toxicology assays. Beyond these applications, the improved differentiation profile may also indicate a better performance in disease modeling and transplantation.

Improved differentiation medium (DM+)

| Concentration | Component |
|---|---|
| | Gibco Advanced DMEM/F12 |
| 10 mM | HEPES |
| 1 x | B27 wo VitA |
| 1 x | N2 |
| 1.25 mM | n-Acetylcysteine |
| 50 ng/ml | hEGF |
| 10 nM | Gastrin |
| 25 ng/ml | HGF |
| 0.5 uM | A83.01 |
| 25 ng/ml | BMP7 |
| 100 ng/ml | FGF19 |
| 10 uM | DAPT |
| 3 uM | Dexamethasone |
| 3 uM | IWP-2 |
| 3 uM | Chir |
| 50 uM | iCRT3 |
| 100 uM | Carbachol |

Old differentiation medium (DM)

| Concentration | Component |
|---|---|
| | Gibco Advanced DMEM/F12 |
| 10 mM | HEPES |
| 1 x | B27 wo VitA |
| 1 x | N2 |
| 1.25 mM | n-Acetylcysteine |
| 50 ng/ml | hEGF |
| 10 nM | Gastrin |
| 25 ng/ml | HGF |
| 0.5 uM | A83.01 |
| 25 ng/ml | BMP7 |
| 100 ng/ml | FGF19 |
| 10 uM | DAPT |
| 3 uM | Dexamethasone |

Expansion medium (EM)

| Concentration | Component |
|---|---|
| | Gibco Advanced DMEM/F12 |
| 10 mM | HEPES |
| 1 x | B27 wo VitA |

-continued

| Expansion medium (EM) | |
| --- | --- |
| Concentration | Component |
| 1 x | N2 |
| 1.25 mM | n-Acetylcysteine |
| 50 ng/ml | hEGF |
| 10 nM | Gastrin |
| 25 ng/ml | HGF |
| 10 % | Rspondin conditioned medium |
| 0.01 M | Nicotinamide |
| 100 ng/ml | FGF10 |
| 5 uM | A83.01 |
| 10 uM | FSK |

The invention claimed is:

1. A composition comprising a differentiated organoid and a differentiation medium, wherein the differentiation medium comprises a basal medium, one or more receptor tyrosine kinase ligands, a Notch inhibitor, a glucocorticoid, a TGF-beta inhibitor, one or more Wnt inhibitors, and a Wnt agonist, wherein the Wnt agonist is a GSK-3 inhibitor, and wherein the one or more Wnt inhibitors comprises an inhibitor that acts downstream of the β-catenin destruction complex.

2. The composition of claim 1, wherein the differentiation medium further comprises one or more additional Wnt inhibitors is selected from: (1) an inhibitor of Wnt secretion, (2) a competitive or non-competitive inhibitor of the interaction between Wnt or Rspondin and the Wnt receptor complex, (3) an inhibitor that promotes the degradation of components of the Wnt receptor complex, (4) an inhibitor of Dishevelled family proteins, (5) an activator that promotes destruction complex activity, (6) an inhibitor of the deoligomerisation of the destruction complex, and/or (7) an inhibitor of β-catenin target gene expression.

3. The composition of claim 2, wherein the inhibitor of Wnt secretion is a Porc inhibitor selected from IWP-2, LGK974, and/or IWP-1.

4. The composition of claim 1, wherein the GSK-3 inhibitor is selected from CHIR99021, 6-BIO, Dibromocantharelline, Hymenialdesine, Indirubins, Meridianins, CT98014, CT98023, CT99021, TWS119, SB-216763, SB-41528, AR-A014418, AZD-1080, Alsterpaullone, Cazpaullone, Kenpaullone, Aloisines, Manzamine A, Palinurine, Tricantine, TDZD-8, NP00111, NP031115, Tideglusib, HMK-32, and L803-mts.

5. The composition of claim 1, wherein the inhibitor that acts downstream of the β catenin destruction complex is an inhibitor of β catenin target gene expression, optionally wherein the inhibitor of β-catenin target gene expression is selected from iCRT3, CGP049090, PKF118310, PKF115 584, ZTM000990, PNU 74654, BC21, iCRT5, iCRT14, and FH535.

6. The composition of claim 1, wherein the differentiation medium further comprises an AP 1 stimulant, optionally wherein the AP 1 stimulant is a muscarinic acetylcholine receptor agonist, optionally selected from acetylcholine, bethanechol, carbachol, oxotremorine, or pilocarpine.

7. The composition of claim 1, wherein:

(a) the one or more receptor tyrosine kinase ligands comprises one or more, or all, of a ligand for RTK class I (EGF receptor family or ErbB family), a ligand for RTK class IV (FGF receptor family), and a ligand for RTK class VI (HGF receptor family), optionally wherein the one or more receptor tyrosine kinase ligands are selected from epidermal growth factor (EGF), fibroblast growth factor (FGF), and hepatocyte growth factor (HGF);

(b) the Notch inhibitor is a gamma secretase inhibitor, optionally DAPT, dibenzazepine (DBZ), benzodiazepine (BZ), or LY-411575;

(c) the glucocorticoid is selected from: dexamethasone, prednisone, prednisolone, methylprednisolone, betamethasone, triamcinolone, beclomethasone, and fludrocortisone acetate; and/or (d) the TGF beta inhibitor is an inhibitor of ALK4, ALK5 or ALK7, optionally selected from: A83-01, SB-431542, SB-505124, SB-525334, LY 364947, SD-208, and SJN 2511.

8. The composition according to claim 1, wherein the differentiation medium comprises EGF, FGF19 and HGF as receptor tyrosine kinase ligands,
DAPT as a notch inhibitor,
IWP2 and iCRT3 as Wnt inhibitor,
dexamethasone as glucocorticoid,
CHIR99021 as GSK-3 inhibitor, and
carbachol as AP-1 inhibitor.

9. The composition according to claim 1, wherein:

(a) the differentiation medium further comprises a BMP pathway activator, optionally selected from one or more of BMP7, BMP4, and BMP2;

(b) the differentiation medium further comprises gastrin; and/or (c) the differentiation medium further comprises one or more components selected from: B27, B27 without retinoic acid, and N2.

* * * * *